US007410766B2

(12) United States Patent
Pompejus et al.

(10) Patent No.: US 7,410,766 B2
(45) Date of Patent: Aug. 12, 2008

(54) CORYNEBACTERIUM GLUTAMICUM GENES ENCODING PHOSPHOENOLPYRUVATE: SUGAR PHOSPHOTRANSFERASE SYSTEM PROTEINS

(75) Inventors: Markus Pompejus, Freinsheim (DE); Burkhard Kröger, Limburgerhof (DE); Hartwig Schröder, Nußloch (DE); Oskar Zelder, Speyer (DE); Gregor Haberhauer, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/506,167

(22) Filed: Aug. 17, 2006

(65) Prior Publication Data

US 2007/0111290 A1   May 17, 2007

Related U.S. Application Data

(60) Division of application No. 11/061,298, filed on Feb. 17, 2005, which is a continuation of application No. 09/604,231, filed on Jun. 27, 2000, now Pat. No. 6,884,614.

(60) Provisional application No. 60/150,310, filed on Aug. 23, 1999, provisional application No. 60/142,691, filed on Jul. 1, 1999.

(30) Foreign Application Priority Data

| Sep. 3, 1999 | (DE) | ................... 199 42 095 |
|---|---|---|
| Sep. 3, 1999 | (DE) | ................... 199 42 097 |

(51) Int. Cl.
| C12N 15/00 | (2006.01) |
|---|---|
| C12N 1/20 | (2006.01) |
| C12P 21/06 | (2006.01) |
| C07H 21/04 | (2006.01) |

(52) U.S. Cl. ..................... 435/6; 435/252.3; 435/320.1; 536/23.1

(58) Field of Classification Search ................ 536/23.1; 435/69.1, 6, 252.3, 320.1
See application file for complete search history.

(56) References Cited

U.S. PATENT DOCUMENTS 6,699,703 B1 * 3/2004 Doucette-Stamm et al. ...... 435/252.3

FOREIGN PATENT DOCUMENTS

| EP | 0204326 A2 | 12/1986 |
|---|---|---|
| EP | 0358940 B1 | 3/1990 |
| EP | 1118666 A3 | 8/2001 |
| JP | 62232392 | 10/1987 |
| JP | 62244382 | 10/1987 |
| JP | 04278088 | 10/1992 |
| JP | 04330284 | 11/1992 |
| JP | 05030977 | 2/1993 |
| JP | 05056782 | 3/1993 |
| JP | 05076352 | 3/1993 |
| JP | 05184366 | 7/1993 |
| JP | 05184371 | 7/1993 |
| JP | 05284970 | 11/1993 |
| JP | 05284972 | 11/1993 |
| JP | 05344881 | 12/1993 |
| JP | 05344893 | 12/1993 |
| JP | 06062866 | 3/1994 |
| JP | 06169780 | 6/1994 |
| JP | 06261766 | 9/1994 |
| JP | 06277067 | 10/1994 |
| JP | 06277073 | 10/1994 |
| JP | 07031476 | 2/1995 |
| JP | 07031478 | 2/1995 |
| JP | 07075578 | 3/1995 |
| JP | 07075579 | 3/1995 |
| JP | 09028391 | 2/1997 |
| JP | 09070291 | 3/1997 |
| JP | 09224661 | 9/1997 |
| WO | WO-9519442 A1 | 7/1995 |
| WO | WO-9818931 A2 | 5/1998 |

OTHER PUBLICATIONS

Ankri, Serge, et al., "Mutations in the *Corynebacterium glutamicum* Proline Biosynthetic Pathway: a Natural Bypass of the *proA* Step," *Journal of Bacteriology*, vol. 178(15):4412-4419 (1996).

Billman-Jacobe, H., "Nucleotide sequence of a *recA* gene from *Cornybacterium glutamicum*, *The Journal of Sequencing and Mapping*," vol. 4:403-404 (1994).

Bonamy, Celine, et al., "Identification of IS 1206, a *Corynebacterium glutamicum* IS3-related insertion sequence and phylogenetic analysis," *Molecular Microbiology*, vol. 14(3):571-581 (1994).

Bonnassie, S., et al., "Nucleotide sequence of the *dapA* gene from *Corynebacterium glutamicum*," *Nucleic Acids Research*, vol. 18(21):6421 (1990).

Börmann, E.R., et al., "Molecular analysis of the *Corynebacterium glutamicum gdh* gene encoding glutamate dehydrogenase," *Molecular Microbiology*, vol. 6(3):317-326 (1992).

Chen, Chian-Chi, et al., "The cloning and nucleotide sequence of a *Corynebacterium glutamicum* 3-deoxy-D-arabinoheptulosonate-7-phosphate synthase gene," *FEMS Micrkobiology Letters*, vol. 107:223-230 (1993).

Chen, Qing et al, "Bg1F, the Sensor of the *bgl* System and the β-Glucosides Permease of *Escherichia coli*: Evidence for Dimerization and Intersubunit Phosphotransfer," *Biochemistry*, vol. 37:8714-8723 (1998).

(Continued)

*Primary Examiner*—Maryam Monshipouri
(74) *Attorney, Agent, or Firm*—Lahive & Cockfield LLP; Maria Laccotripe Zacharakis; Maneesh Gulati

(57) ABSTRACT

Isolated nucleic acid molecules, designated PTS nucleic acid molecules, which encode novel PTS proteins from *Corynebacterium glutamicum* are described. The invention also provides antisense nucleic acid molecules, recombinant expression vectors containing PTS nucleic acid molecules, and host cells into which the expression vectors have been introduced. The invention still further provides isolated PTS proteins, mutated PTS proteins, fusion proteins, antigenic peptides and methods for the improvement of production of a desired compound from *C. glutamicum* based on genetic engineering of PTS genes in this organism.

22 Claims, No Drawings

OTHER PUBLICATIONS

Cianciotto, Nicholas, et al., "DNA sequence homology between attB-related sites of *Corynebacterium diphtheriae, Corynebacterium ulcerans, Corynebacterium glutamicum,* and the *att*P site of γ-Corynephage," *FEMS Microbiology Letters,* vol. 66:299-302 (1990).

Correia, Antonio, et al., "Cloning and characterization of an IS-like element present in the genome of *Brevibacterium lactofermentum* ATCC 13869," *Gene,* vol. 170:91-94 (1996).

Dominguez, et al., "Complete sucrose metabolism requires fructose phosphotransferase activity in *Corynebacterium glutamicum* to ensure phosphorylation of liberated fructose," Applied and Environmental Microbiology, vol. 62(10):3878-3880 (1996).

Eikmanns, Bernhard J., et al., "Nucleotide sequence, expression and transcriptional analysis of the *Corynebacterium glutamicum gltA* gene encoding citrate synthase," *Microbiology,* vol. 140:1817-1828 (1994).

Eikmanns, Bernhard J., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase," *Journal of Bacteriology,* vol. 174(19):6076-6086 (1992).

Eikmanns, Bernhard J., et al., "Cloning, Sequence Analysis, Expression, and Inactivation of the *Corynebacterium glutamicum icd* Gene Encoding Isocitrate Dehydrogenase and Biochemical Characterization of the Enzyme," *Journal of Bacteriology,* vol. 177(3):774-782 (1995).

Eikmanns, Bernhard J., et al., "The phosphoenolpyruvate carboxylase gene of *Corynebacterium glutamicum:* Molecular cloning, nucleotide sequence, and expression," *Mol. Gen. Genet.,* vol. 218:330-339 (1989).

Fitzpatrick, R., et al., "Construction and characterization of *recA* mutant strains of *Corynebacterium glutamicum* and *Brevibacterium lactofermentum,*" *Appl. Microbiol. Biotechnol.,* vol. 42:575-580 (1994).

Follettie, Max T., et al., "Molecular Cloning and Nucleotide Sequence of the *Corynebacterium glutamicum pheA* Gene," *Journal of Bacteriology,* vol. 167(2):695-702 (1986).

Fouet, Agnes, et al., "*Bacillus subtilis* sucrose-specific enzyme II of the phosphotransferase system: Expression in *Escherichia coli* and homology to enzymes II from enteric bacteria," *Proc. Natl. Acad. Sci.,* vol. 84:8773-8777 (1987).

Han, K.-S., et al., "The molecular structure of the *Corynebacterium glutamicum* threonine synthase gene," *Molecular Microbiology,* vol. 4(10):1693-1702 (1990).

Heery, D.M., et al., "Nucleotide sequence of the *Corynebacterium glutamicum trpE* gene," *Nucleic Acids Research,* vol. 18(23):7138 (1990).

Heery, D.M., et al., "Cloning of the trp Gene Cluster from a Tryptophan-Hyperproducing Strain of *Corynebacterium glutamicum:* Identification of a Mutation in the trp Leader Sequence," *Applied and Environment Microbiology,* vol. 59(3):791-799 (1993).

Heery, David M., et al., "A Sequence from a Tryptophan-Hyperproducing Strain of *Corynebacterium glutamicum* Encoding Resistance to 5-Methyltryptophan," *Biochemical and Biophysical Research Communications,* vol. 201(3):1255-1262 (1994).

Honrubia, M.P., et al., "Identification, characterization, and chromosomal organization of the *ftsZ* gene from *Brevibacterium lactofermentum,*" *Mol. Gen. Genet.,* vol. 259:97-104 (1998).

Ishino, Shuichi, et al., "Nucleotide sequence of the meso-diaminopimelate D-dehydrogenase gene from *Corynebacterium glutamicum,*" *Nucleic Acids Research,* vol. 15(9):3917 (1987).

Jäger, Wolfgang, et al., "A *Corynebacterium glutamicum* Gene Conferring Multidrug Resistance in the Heterologous Host *Eschericha coli,*" *Journal of Bacteriology,* vol. 179(7):2449-2451 (1997).

Jäger, Wolfgang, et al., "A *Corynebacterium glutamicum* gene encoding a two-domain protein similar to biotin carboxylases and biotin-carboxyl-carrier proteins," *Arch. Microbiol.,* vol. 166:76-82 (1996).

Jakoby, Marc, et al., "Isolation of the *Corynebacterium glutamicum glnA* gene encoding glutamine synthetase I," *FEMS Microbiology Letters,* vol. 154:81-88 (1997).

Jakoby, Marc, et al., "Nitrogen regulation in *Corynebacterium glutamicum:* isolation of genes involved and biochemical characterization of corresponding proteins," *FEMS Microbiology Letters,* vol. 173:303-310 (1999).

Jetten, Mike S., et al., "Structural and Functional Analysis of Pyruvate Kinase from *Corynebacterium glutamicum,*" *Applied and Environmental Microbiology,* vol. 60(7):2501-2507 (1994).

Joliff, G., et al., "Cloning and nucleotide sequence of the *csp1* gene encoding PS1, one of the two major secreted proteins of *Corynebacterium glutamicum:* the deduced N-terminal region of PS1 is similar to the *Mycobacterium* antigen 85 complex," *Molecular Microbiology,* vol. 6(16):2349-2362 (1992).

Kalinowski, J., et al., "Genetic and biochemical analysis of the aspartokinase from *Corynebacterium glutamicum,*" *Molecular Microbiology,* vol. 5(5):1197-1204 (1991).

Kalinowski, Jörn, et al., "Aspartokinase gene $lysC_\alpha$ and $lysC\beta$ overlap and are adjacent to the aspartate β-semialdehyde dehydrogenase gene *asd* in *Corynebacterium glutamicum,*" *Mol. Gen. Genet.,* vol. 224:317-324 (1990).

Keilhauer, Carmen, et al., "Isoleucine Synthesis in *Corynebacterium glutamicum:* Molecular Analysis of the *ilvB-ilvN-ilvC* Operon," *Journal of Bacteriology,* vol. 175(17):5595-5603 (1993).

Kimura, Eiichiro, et al., "Molecular Cloning of a Novel Gene, *dtsR,* Which Rescues the Detergent Sensitivity of a Mutant Derived from *Brevibacterium lactofermentum,*" *Biosci. Biotech. Biochem.,* vol. 60(10):1565-1570 (1996).

Kobayashi, Miki, et al., "Cloning, Sequencing, and Characterization of the *ftsZ* Gene from Coryneform Bacteria," *Biochemical and Biophysical Research Communications,* vol. 236:383-388 (1997).

Kronemeyer, Wolfgang, et al., "Structure of the *gluABCD* Cluster Encoding the Glutamate Uptake System of *Corynebacterium glutamicum,*" *Journal of Bacteriology,* vol. 177(5):1152-1158 (1995).

Lee, Heung-Shick, et al., "Molecular Characterization of AceB, a Gene Encoding Malate Synthase in *Corynebacterium glutamicum,*" *Journal of Microbiology and Biotechnology,* vol. 4(4):256-263 (1994).

Le Marrec, Claire, et al., "Genetic Characterization of Site-Specific Integration Functions of ΦAAU2 Infecting '*Arthrobacter aureus*' C70," *Journal of Bacteriology,* vol. 178(7):1996-2004 (1996).

Lepiniec, Loïc, et al., "*Sorghum* phosphoenolpyruvate carboxylase gene family: structure, function and molecular evolution," *Plant Molecular Biology,* vol. 21:487-502 (1993).

Lichtinger, Thomas, et al., "Biochemical and Biophysical Characterization of the Cell Wall Porin of *Corynebacterium glutamicum:* The Channel Is Formed by a Low Molecular Mass Polypeptide," *Biochemistry,* vol. 37:15024-15032 (1998).

Ludwig, W., et al., "Phylogenetic relationships of *Bacteria* based on comparative sequence analysis of elongation factor Tu and ATP-synthase β-subunit genes," *Antonie van Leeuwenhoek,* vol. 64:285-305 (1993).

Malubres, Marcos, et al., "Analysis said Expression of the *thrC* Gene of *Brevibacterium lactofermentum* and Characterization of the Encoded Threonine Synthase," *Applied and Environmental Microbiology,* vol. 60(7):2209-2219 (1994).

Marcel, T., et al., "Nucleotide sequence and organization of the upstream region of the *Corynebacterium glutamicum lysA* gene," *Molecular Microbiology,* vol. 4(11):1819-1830 (1990).

Mateos, Luis M., et al., "Nucleotide sequence of the homoserine kinase (*thr* B) gene of *Brevibacterium lactofermentum,*" *Nucleic Acids Research,* vol. 15(9):3922 (1987).

Mateos, Luis M., et al., "Nucleotide sequence of the homoserine dehydrogenase (*thr* A) gene of *Brevibacterium lactofermentum,*" *Nucleic Acids Research,* vol. 15(24):10598 (1987).

Matsui, Kazuhiko, et al., "Complete nucleotide and deduced amino acid sequences of the *Brevibacterium lactofermentum* tryptophan operon," *Nucleic Acids Research,* vol. 14(24):10113-10114 (1986).

Möckel, Bettina, et al., "Functional and Structural Analyses of Threonine Dehydratase from *Corynebacterium glutamicum,*" *Journal of Bacteriology,* vol. 174(24):8065-8072 (1992).

Moreau, Sylvia, et al., "Site-specific integration of corynephage Φ16: construction of an integration vector," *Microbiology*, vol. 145:539-548 (1999).

Moreau, Sylvie, et al., "Analysis of the Integration Functions of Φ304L: An Integrase Module among Corynephages," *Virology*, vol. 255:150-159 (1999).

O'Gara, James P., et al., "Mutations in the *trpD* Gene of *Corynebacterium glutamicum* Confer 5-Methyltryptophan Resistance by Encoding a Feedback-Resistant Anthranilate Phosphoribosyltransferase," *Applied and Environmental Microbiology*, vol. 61(12):4477-4479 (1995).

Oguiza, José A., et al., "A Gene Encoding Arginyl-tRNA Synthetase is Located in the Upstream Region of the lysA Gene in *Brevibacterium lactofermentum*: Regulation of *argS-lysA* Cluster Expression by Arginine," *Journal of Bacteriology*, vol. 175(22):7356-7362 (1993).

Oguiza, José A., et al., "Molecular Cloning, DNA Sequence Analysis, and Characterization of the *Corynebacterium diphtheriae dtxR* Homology from *Brevibacterium lactofermentum*," *Journal of Bacteriology*, vol. 177(2):465-467 (1995).

Oguiza, José A., et al., "Multiple Sigma Factor Genes in *Brevibacterium lactofermentum*: Characterization of *sigA* and *sigB*," *Journal of Bacteriology*, vol. 178(2):550-553 (1996).

Oguiza, José A., et al., "The galE gene encoding the UDP-galactose 4-epimerase of *Brevibacterium lactofermentum* is coupled transcriptionally to the *dmdR* gene," *Gene*, vol. 177:103-107 (1996).

O'Regan, Michael, et al., "Cloning and nucleotide sequence of the phosphoenolpyruvate carboxylase-coding gene of *Corynebacterium glutamicum* ATCC13032," *Gene*, vol. 77:237-251 (1989).

Park, Soo-Dong, et al., "Isolation and Analysis of *metA*, a Methionine Biosynthetic Gene Encoding Homoserine Acetyltransferase in *Corynebacterium glutamicum*," *Mol. Cells*, vol. 8(3):286-294 (1998).

Park, Yong-Ha, et al., "Phylogenetic Analysis of the Coryneform Bacteria by 5S rRNA Sequences," *Journal of Bacteriology*, vol. 169(5):1801-1806 (1987).

Pascual, Cristina, et al., "Phylogenetic Analysis of the Genus *Corynebacterium* Based on 16S rRNA Gene Sequences," *International Journal of Systematic Bacteriology*, vol. 45(4):724-728 (1995).

Pátek, M., et al., "Analysis of the *leuB* gene from *Corynebacterium glutamicum*," *Appl Microbiol Biotechnol*, vol. 50:42-47 (1998).

Pátek, Miroslav, et al., "Leucine Synthesis in *Corynebacterium glutamicum*: Enzyme Activities, Structure of *leuA*, and Effect of *leuA* Inactivation on Lysine Synthesis," *Applied and Environmental Microbiology*, vol. 60(1):133-140 (1994).

Pátek, Miroslav, et al., "Promoters from *Corynebacterium glutamicum*: cloning, molecular analysis and search for a consensus motif," *Microbiology*, vol. 142:1297-1309 (1996).

Pátěk, M., et al., "Identification and transcriptional analysis of the *dapB*-ORF2-*dapA*-ORF4 operon of *Corynebacterium glutamicum*, encoding two enzymes involved in L-lysine synthesis," *Biotechnology Letters*, vol. 19(11):1113-1117 (1997).

Peoples, O.P., et al., "Nucleotide sequence and fine structural analysis of the *Corynebacterium glutamicum hom-thrB* operon," *Molecular Microbiology*, vol. 2(1):63-72 (1988).

Peter, Heidi, et al., "*Corynebacterium glutamicum* is Equpped with Four Secondary Carriers for Compatible Solutes: Identification, Sequencing, and Characterization of the Proline-Ectoine Uptake System, ProP, and the Ectoine/Proline/Glycine Betaine Carrier, EctP," *Journal of Bacteriology*, vol. 180(22):6005-6012 (1998).

Peter, Heidi, et al., "Isolation of the *putP* gene of *Corynebacterium glutamicum* and characterization of a low-affinity uptake system for compatible solutes," *Arch Microbiol*, vol. 168:143-151 (1997).

Peter, Heidi, et al., "Isolation, Characterization, and Expression of the *Corynebacterium glutamicum betP* Gene, Encoding the Transport System for the Compatible Solute Glycine Betaine," *Journal of Bacteriolgy*, vol. 178(17):5229-5234 (1996).

Peters-Wendisch, Petra G., et al., "Pyruvate carboxylase from *Corynebacterium glutamicum*: characterization, expression and inactivation of the *pyc* gene," *Microbiology*, vol. 144:915-927 (1998).

Peyret, J.L., et al., "Characterization of the *cspB* gene encoding PS2, an ordered surface-layer protein in *Corynebacterium glutamicum*," *Molecular Biology*, vol. 9(1):97-109 (1993).

Pisabarro, Agustin, et al., "A Cluster of Three Genes (*dapA, orf2, and dapB*) of *Brevibacterium lactofermentum* Encodes Dihydrodipicolinate Synthase, Dihydrodipicolinate Reductase, and a Third Polypeptide of Unknown Function," *Journal of Bacteriology*, vol. 175(9):2743-2749 (1993).

Rainey, Frederick A., et al., "Phylogenetic analysis of the genera *Rhodococcus* and *Nocardia* and evidence for the evolutionary origin of the genus *Nocardia* from within the radiation of *Rhodococcus* species," *Microbiology*, vol. 141:523-528 (1995).

Ramos, Adoración, et al., "Cloning, sequencing and expression of the gene encoding elongation factor P in the amino-acid producer *Brevibacterium lactofermentum* (*Corynebacterium glutamicum* ATCC 13869)," *Gene*, vol. 198:217-222 (1997).

Reinscheid, Dieter, J., et al., "Cloning, sequence analysis, expression and inactivation of the *Corynebacterium glutamicum pta-ack* operon encoding phosphotransacetylase and acetate kinase," *Microbiology*, vol. 145:503-513 (1999).

Reinscheid, Dieter J., et al., "Characterization of the Isocitrate Lyase Gene from *Corynebacterium glutamicum* and Biochemical Analysis of the Enzyme," *Journal of Bacteriology*, vol. 176(12):3474-3483 (1994).

Reinscheid, Dieter J., et al., "Malate synthase from *Corynebacterium glutamicum*: sequence analysis of the gene and biochemical characterization of the enzyme," *Microbiology*, vol. 140:3099-3108 (1994).

Roller, Carsten, et al., "Gram-positive bacteria with a high DNA G+C content are characterized by a common insertion within their 23S rRNA genes," *Journal of General Microbiology*, vol. 138:1167-1175 (1992).

Rossol, Ingrid, et al., "The *Corynebacterium glutamicum* aecD Gene Encodes as C-S Lyase with $\alpha,\beta$-Elimination Activity That Degrades Aminoethylcysteine," *Journal of Bacteriology*, vol. 174(9):2968-2977 (1992).

Ruimy, Raymond, et al., "Phylogeny of the Genus *Corynebacterium* Deduced from Analyses of Small-Subunit Ribosomal DNA Sequences," *International Journal of Systematic Bacteriology*, vol. 45(4):740-746 (1995).

Sahm, Hermann, et al., "D-Pantothenate Synthesis in *Corynebacterium glutamicum* and Use of *panBC* and Genes Encoding L-Valine Synthesis for D-Pantothenate Overproduction," *Applied and Environmental Microbiology*, vol. 65(5):1973-1979 (1999).

Sakanyan, Vehary, et al., "Genes and enzymes of the acetly cycle of arginine biosynthesis in *Corynebacterium glutamicum*: enzyme evolution in the early steps of the arginine pathways," *Microbiology*, vol. 142:99-108 (1996).

Sano, Konosuke, et al., "Structure and function of the *trp* operon control regions of *Brevibacterium lactofermentum*, a glutamic-acid-producing bacterium," *Gene*, vol. 53:191-200 (1987).

Schäfer, Andreas, et al., "Cloning and Characterization of a DNA Region Encoding a Stress-Sensitive Restriction System from *Corynebacterium glutamicum* ATCC 13032 and Analysis of Its Role in Intergeneric Conjugation with *Escherichia coli*," *Journal of Bacteriology*, vol. 176(23):7309-7319 (1994).

Schäfer, Andreas, et al., "The *Corynebacterium glutamicum* cgIIM gene encoding a 5-cytosine methyltransferase enzyme confers a specific DNA methylation pattern in an McrBC-deficient *Escherichia coli* strain," *Gene*, vol. 203:95-101 (1997).

Seep-Feldhous, A.J., et al., "Molecular analysis of the *Corynebacterium glutamicum lysI* gene involved in lysine uptake," *Molecular Microbiology*, vol. 5(12):2995-3005 (1991).

Serebrijski, I, et al., "Multicopy Suppression by *asd* Gene and Osmotic Stress-Dependent Complementation by Heterologous *proA* in *proA* Mutants," *Journal of Bacteriology*, vol. 177(24):7255-7260 (1995).

Serebriiskii, Ilya G., et al., "Two new members of the BioB superfamily: cloning, sequencing and expression of *bioB* genes of *Methylobacillus flagellatum* and *Corynebacterium glutamicum*," *Gene*, vol. 175:15-22 (1996).

Siewe, Ruth M. et al, "Functional and Genetic Characterization of the (Methyl)ammonium Uptake Carrier of *Corynebacterium glutamicum*," *The Journal of Biological Chemistry*, vol. 271(10):5398-5403 (1996).

Usuda, Yoshihiro, et al., "Molecular cloning of the *Corynebacterium glutamicum* ('*Brevibacterium lactofermentum*' AJ12036) *odhA* gene encoding a novel type of 2-oxoglutarate dehydrogenase," *Microbiology*, vol. 142:3347-3354 (1996).

Vertès, Alain A., et al., "Isolation and characterization of IS31831, a transposable element from *Corynebacterium glutamicum*," *Molecular Microbiology*, vol. 11(4):739-746 (1994).

von der Osten, C.H., et al., "Molecular cloning, nucleotide sequence and fine-structural analysis of the *Corynebacterium glutamicum fda* gene: structural comparison of *C. glutamicum* fructose-1,6-biphosphate aldolase to class I and class II aldolases," *Molecular Microbiology*, vol. 33(11):1625-1637 (1989).

Vrljic, Marina, et al., "A new type of transporter with a new type of cellular function: L-lysine export from *Corynebacterium glutamicum*," *Molecular Microbiology*, vol. 22(5):815-826 (1996).

Wachi, M., et al., "A *murC* gene from coryneform bacteria," *Appl Microbiol Biotechnol*, vol. 51:223-228 (1999).

Wehmeier, Lutz, et al., "The role of the *Corynebacterium glutamicum rel* gene in (p)ppGpp metabolism," *Microbiology*, vol. 144:1853-1862 (1998).

Wehrmann, Axel, et al., "Different Modes of Diaminopimelate Synthesis and Their Role in Cell Wall Integrity: a Study with *Corynebacterium glutamicum*," *Journal of Bacteriology*, vol. 180(12):3159-3165 (1998).

Wehrmann, Axel, et al., "Analysis of different DNA fragments of *Corynebacterium glutamicum* complementing *dapE* of *Escherichia coli*," *Microbiology*, vol. 140:3349-3356 (1994).

Wehrmann, Axel, et al., "Functional Analysis of Sequences Adjacent to *dapE* of *Corynebacterium glutamicum* Reveals the Presence of *aroP*, Which Encodes the Aromatic Amino Acid Transporter," *Journal of Bacteriology*, vol. 177(20):5991-5993 (1995).

Yeh, Patrice, et al., "Nucleotide sequence of the *lysA* gene of *Corynebacterium glutamicum* and possible mechanisms for modulation of its expression," *Mol Gen Genet*, vol. 212:112-119 (1988).

GenBank Accession No. A09073 for DNA fragment coding for phosphoenolpyruvat corboxylase, recombinant DNA carrying said fragment, strains carrying the recombinant DNA and method for producing L-amino acids using said strains, Bachmann, B. et al, Apr. 14, 2005.

GenBank Accession No. A45579 for Production of L-isoleucine by means of recombinant micro-organisms with deregulated threonine dehydratase, Moeckel, B. et al, Mar. 7, 1997.

GenBank Accession No. A45581, Moeckel, B. et al, "Production of L-Isoleucine by Means of Recombinant Micro-Organisms with Deregulated Threonine Dehydratase." Mar. 7, 1997.

GenBank Accession No. A45583, Moeckel, B. et al, "Production of L-Isoleucine by Means of Recombinant Micro-Organisms with Deregulated Threonine Dehydratase." Mar. 7, 1997.

GenBank Accession No. A45585, Moeckel, B. et al, "Production of L-Isoleucine by Means of Recombinant Micro-Organisms with Deregulated Threonine Dehydratase." Mar. 7, 1997.

GenBank Accession No. A45587 for Production of L-isoleucine by means of recombinant micro-organisms with deregulated threonine dehydratase, Moecke, B. et al, Mar. 7, 1997.

GenBank Accession No. AA011641 for Generation and analysis of 280,000 human expressed sequence tags, Hillier, L. et al, May 9, 1997.

GenBank Accession No. AA655226 for The WashU-HHMI Mouse EST Project, Marra, M. et al, Nov. 4, 1997.

GenBank Accession No, AA704727 for WashU-NCI human EST Project, Hillier, L. et al, Dec. 24, 1997.

GenBank Accession No. AB003132 for Cloning, sequencing, and characterization of the *ftsZ* gene from coryneform bacteria, Kobayashi, M. et al, Aug. 4, 1997.

GenBank Accession No. AB004056, Saito, T., "Mammalian BarH homologue is a potential regulator of neural bHLH genes," Dev. Biol., vol. 199(2):216-225 (1998) Sep. 2, 1998.

GenBank Accession No. AB015023 for A *murC* gene from coryneform bacteria, Wachi, M. et al, Dec. 15, 2001.

GenBank Accession No. AB015853 for Expression in *Escherichia coli* of a new multidrug efflux pump, MexXY, from *Pseudomonas aeruginosa*, Mine, T. et al, Aug. 2, 2000.

GenBank Accession No. AB018530 for Molecular cloning of a novel gene, dtsR, which rescues the detergent sensitivity of a mutant derived from *Brevibacterium lactofermentum*, Kimura, E. et al, Oct. 16, 1998.

GenBank Accession No. AB018531 for The role of DtsR2 in the glutamate-production in coryneform bacteria, Kimura, E. et al, Oct. 16, 1998.

GenBank Accession No. AB020624 for Isolation of the *murI* gene from *Brevibacterium lactofermentum* ATCC 13869 encoding D-glutamate racemase, Malathi, K.C. et al, Jul. 24, 1999.

GenBank Accession No. AB023377 for Nucleotide sequence of the *Corynebacterium glutamicum* transketolase gene, Ikeda, M. et al, 02/20/9.

GenBank Accession No. AB024708 for *Corynebacterium glutamicum* gltBD gene, Kanno, S. et al, Mar. 13, 1999.

GenBank Accession No. AB025424 for *Brevibacterium lactofermentum* ATCC 13869 acn gene for Aconitase, Nakamura, J. et al, Apr. 3, 1999.

GenBank Accession No. AB027714 for Cryptic plasmid pCG1 of *Corynebacterium glutamicum*, Yonetani, Y. et al, Jun. 1, 1999.

GenBank Accession No. AB027715 for Plasmid pCG11 of *Corynebacterium glutamicum*, Yonetani, Y. et al, Jun. 1, 1999.

GenBank Accession No. AC004295 for Sequencing of *Drosophila* chromosome 2R, region 55C1-55C4, Celniker, S.E. et al, Jul. 29, 1998.

GenBank Accession No. AC005019 for Toward a complete human genome sequence, Sulston, J.E. et al, Oct. 15, 2003.

GenBank Accession No. AC006044 for Toward a complete human genome sequence, Sulston, J.E. et al, Oct. 8, 2003.

GenBank Accession No. AC006474 for the DNA sequence of human chromosome 7, Hillier, L.W. et al, Jan. 27, 2004.

GenBank Accession No. AC007084 for Sequencing of *Drosophila* chromosme 2R, region 43F-44A, Celniker, S.E. et al, Mar. 21, 2001.

GenBank Accession No. AC007739 for The sequence of *Homo sapiens* BAC clone RP11-91L3, Hou, S. et al, Apr. 16, 2005.

GenBank Accession No. AC008403, DOE Joint Genome Institute and Stanford Human Genome Center, for *Homo sapiens* chromosome 19 clone CTC-273B12, complete sequence, Mar. 22, 2003.

GenBank Accession No. AC009298 for The sequence of *Homo sapiens* BAC clone RP11-1716, Nguyen, C. et al, Apr. 15, 2005.

GenBank Accession No. AC010187 for *Homo sapiens* chromosome 12 clone RP11-38909, Working Draft Sequence, 40 unordered pieces, Muzny, D.M. et al, Jan. 8, 2003.

GenBank Accession No. AC011647 for *Homo sapiens* chromosome 11, clone RP11-15D18, Birren, B. et al, Jun. 18, 2002.

GenBank Accession No. AD000002 for *Mycobacterium tuberculosis*, Du, L., Dec. 10, 1996.

GenBank Accession No. AD000016 for *Mycobacterium tuberculosis*, Du, L., Dec. 3, 1996.

GenBank Accession No. AE000654 for The complete genome sequence of the gastric pathogen *Helicobacter pylori*, Tomb, J.-F. et al, Apr. 6, 1999.

GenBank Accession No. AF001552 for Genome duplications and other features in 12 Mb of DNA sequence from human chromosome 16p and 16q, Loftus, B.J. et al, Jan. 1, 2000.

GenBank Accession No. AF005242, Chun, J.Y. et al, "Molecular cloning and analysis of the *argC* gene from *Corynebacterium glutamicum*," *Biochem. Mol. Biol. Int.*, vol. 46(3):437-447 (1998), Jul. 23, 2001.

GenBank Accession No. AF005635 for *Corynebacterium glutamicum*, Reid, S.J. et al, Jun. 14, 1999.

GenBank Accession No. AF030405 for Molecular cloning of the histidine biosynthetic genes from *Corynebacterium glutamicum*, Jung, S.I. et al, Nov. 13, 1997.

GenBank Accession No. AF030520, Ko, S.Y. et al, "Molecular cloning of the *argG* gene from *Corynebacterium glutamicum*." Nov. 19, 1997.

GenBank Accession No. AF031518, Chun, J.Y. et al, "Cloning of the argF gene encoding the ornithine carbamoyltransferase from *Corynebacterium glutamicum*," *Mol. Cells*, vol. 9(3):333-337 (1999), Jun. 13, 2001.

GenBank Accession No. AF036932 for Molecular cloning of the aroD gene from *Corynebacterium glutamicum*, Park, K.-Y. et al, Dec. 13, 1997.

GenBank Accession No. AF038548 for Sequence of the *Corynebacterium glutamicum* pyruvate carboxylase gene, Koffas, M.A. et al, Aug. 25, 2000.

GenBank Accession No. AF038651 for The role of the *Corynebacterium glutamicum* rel gene in (p)ppGpp metabolism, Wehmeier, L. et al, Mar. 15, 2001.

GenBank Accession No. AF041436, Ko. S.-Y. et al, "The argR gene of *Corynebacterium glutamicum*." Jan. 5, 1999.

GenBank Accession No. AF045998 for Molecular cloning of the histidine biosynthetic genes from *Corynebacterium glutamicum*, Jund, S.I. et al, Feb. 19, 1998.

GenBank Accession No. AF048764, Park. M.Y. et al, "Molecular cloning of the argH gene encoding argininosuccinate lyase from *Corynebacterium glutamicum*." Jul. 1, 1998.

GenBank Accession No. AF049897, Park, M.Y. et al, "Molecular cloning of the Arginine Biosynthetic Gene from *Corynebacterium glutamicum*." Jul. 1, 1998.

GenBank Accession No. AF050109 for The function of the inhA gene in mycolic acid synthesis of *Corynebacterium glutamicum*, Sayyada-Hafeez, A. et al, Nov. 19, 2002.

GenBank Accession No. AF050166, Kwon, J.H. et al, "Cloning of the histidine biosynthetic genes from *Corynebacterium glutamicum*: organization and analysis of the hisG and hisE genes," *Can. J. Microbiol.*, vol. 46(9):848-855 (2000), Apr. 26, 2002.

GenBank Accession No. AF051846 for *Corynebacterium glutamicum*, Jung, S.I. et al, Mar. 12, 1998.

GenBank Accession No. AF052652 for Isolation and Analysis of metA, a Metionine Biosynthetic Gene Encoding Homoserine Acetyltransferase in *Corynebacterium glutamicum*, Park, S.-D. et al, Mar. 19, 1998.

GenBank Accession No. AF053071 for Cloning and analysis of the aroB gene encoding dehyddroquinate synthase from *Corynebacterium glutamicum*, Han, M.A. et al, Apr. 26, 2002.

GenBank Accession AF060558 for *Corynebacterium glutamicum*, Juns, S.I. et al, Apr. 29, 1998.

GenBank Accession No. AF086704 for *Corynebacterium glutamicum*, Kwon, J.H. et al, Feb. 8, 1999.

GenBank Accession No. AF114233 for Cloning and molecular analysis of the *Corynebacterium glutamicum* ASO19 and aroA gene, O'Donohue, M. et al, Feb. 7, 1999.

GenBank Accession No. AF116184, Dusch, N. et al, "Expression of the *Corynebacterium glutamicum* panD gene encoding L-aspartate-alpha-decarboxylase leads to pantothenate overproduction in *Escherichia coli*," *Appl. Environ. Microbiol.*, vol. 65(4):1530-1539 (1999), May 2, 1999.

GenBank Accession No. AF124518 for The cloning and phylogenetic analysis of the 3-dehydroquinase gene from *Corynebacterium glutamicum*, Joy, J. et al, May 18, 1999.

GenBank Accession No. AF124600 for Genetic aspects of the prechorismate pathway in *Corynebacterium glutamicum*, Burke, K.G. et al, May 4, 1999.

GenBank Accession No. AF145897 for Comparison of inhA gene of *Corynebacterium glutamicum* with its mutants and other related species, Hafeez, S. A. et al, Nov. 19, 2002.

GenBank Accession No. AF145898 for Comparison of inhA gene for *Corynebacterium glutamicum* with its mutants and other related species, Hafeez, S. A. et al, Nov. 19, 2002.

GenBank Accession No. AI190741, NCI-CGAP http://www.ncbi.nlm.nih.gov/ncicgap, for National Cancer Institute, Cancer Genome Ariatomy Project (CGAP), Tumor Gene Index, Oct. 28, 1998.

GenBank Accession No. AJ001436 for *Corynebacterium glutamicum* is equipped with four secondary carriers for compatible solutes: identification, sequencing, and characterization of the proline/ectoine uptake system, ProP, and the ectoine/proline/glycine betaine carrier, EctP, Peter, H. et al, Nov. 20, 1998.

GenBank Accession No. AJ004934, Wehrmann, A. et al, "Different modes of diaminopimelate synthesis and their role in cell wall integrity: a study with *Corynebacterium glutamicum*," *J. Bacteriol.*, vol. 180(12):3159-3165 (1998), Jun. 17, 1998.

GenBank Accession No. AJ007732, Jakoby, M.J. et al, "Ammonium uptake in *Corynebacterium glutamicum* is regulated on the level of expression and enzyme activity." Apr. 15, 2005.

GenBank Accession No. AJ010319 for Nitrogen regulation in *Corynebacterium glutamicum*: isolation of genes involved and biochemical characterization of corresponding proteins, Jakoby, M. et al, Apr. 15, 2005.

GenBank Accession No. AJ132968 for Construction and application of new *Corynebacterium glutamicum* vectors, Jakoby, M.J. et al, May 4, 1999.

GenBank Accession No. AJ224946 for Biochemical and genetic characterization of the membrane-associated malate dehydrogenase (acceptor) from *Corynebacterium glutamicum*, Molenaar, D. et al, Aug. 11, 1998.

GenBank Accession No. AJ238250 for Functions of the membrane-associated and cytoplasmic malate dehydrogenases in the citric acid cycle of *Corynebacterium glutamicum*, Molenaar, D. et al, Dec. 3, 2000.

GenBank Accession No. AJ238703 for Biochemical and biophysical characterization of the cell wall porin of *Corynebacterium glutamicum*: the channel is formed by a low molecular mass polypeptide, Lichtinger, T. et al, May 7, 1999.

GenBank Accession No. AL022075 for Deciphering the biology of *Mycobacterium tuberculosis* from the complete genome sequence, Cole, S.T. et al, Sep. 2, 2002.

GenBank Accession No. AL022268 for A set of ordered cosmids and a detailed genetic and physical map for the 8 Mb *Streptomyces coelicolor* A3 (2) chromosome, Redenbach, M. et al, May 12, 2002.

GenBank Accession No. AL023591 for Use of an ordered cosmid library to deduce the genomic organization of *Mycobacterium leprae*, Eiglmeier, K. et al, Apr. 16, 2005.

GenBank Accession No. AL035159 for Use of an ordered cosmid library to deduce the genomic organization of *Mycobacterium leprae*, Eiglmeier, K. et al, Apr. 16, 2005.

GenBank Accession No. AL081678 for *Arabidopsis thaliana*, Salanoubat, M. et al, Jun. 28, 1999.

GenBank Accession No. AL096814 for *Homo sapiens*, Sehra, H., May 18, 2005.

GenBank Accession No. AL101527 for *Drosophila melanogaster*, Genoscope, Jul. 26, 1999.

GenBank Accession No. AP000004 for Complete sequence and gene organization of the genome of a hyper-thermophilic archaebacterium, *Pyrococcus horikoshii* OT3, Kawarabayasi, Y. et al, May 27, 2004.

GenBank Accession No. AP000140 for *Homo sapiens* 911,949bp genomic DNA of 21q21.2 (Region: LL56-APP Clone Range: B2291C14-R44F3), Hattori, M. et al, Jan. 8, 2000.

GenBank Accession No. AP00028 for *Homo sapiens* 75,698bp genomic DNA of 21q21.2, Hattori, M. et al, Nov. 20, 1999.

GenBank Accession No. AQ128685 for Sequence-tagged connectors: A sequence approach to mapping and scanning the human genome, Mahairas, G.G. et al, Sep. 23, 1998.

GenBank Accession No. AQ364540 for A BAC End Sequencing Framework to Sequence the Rice Genome, Wing, R.A. et al, Dec. 16, 1999.

GenBank Accession No. AQ463737 for Sequence-tagged connectors: A sequence approach to mapping and scanning the human genome, Mahairas, G.G. et al, Apr. 23, 1999.

GenBank Accession No. AW047296, Bonaldo, M.F. et al, "Normalization and subtraction: two approaches to facilitate gene discovery," *Genome Res.*, vol. 6(9):791-806 (1996) Sep. 18, 1999.

GenBank Accession No. B10133 for BAC End Sequences at ATGC, Feng, J. et al, May 14, 1997.

GenBank Accession No. C97772 for Rice cDNA from callus, Sasaki, T. et al, Apr. 4, 2002.

GenBank Accession No. D17429 for Isolation and characterization of IS31831, a transposable element from *Corynebacterium glutamicum*, Vertes, A.A. et al, Feb. 4, 1999.

GenBank Accession No. D84102 for Molecular cloning of the *Corynebacterium glutamicum* ('*Brevibacterium lactofermentum*' AJ12036) odhA gene encoding a novel type of 2-oxoglutarate dehydrogenase, Usuda, Y. et al, Feb. 6, 1999.

GenBank Accession No. D84432 for Systematic sequencing of the 283 kb 210 degrees-232 degrees region of the *Bacillus subtilis* genome containing the skin element and many sporulation genes, Mizuno, M. et al, Feb. 6, 1999.

GenBank Accession No. D87915 for Molecular cloning and characterization of the obg gene of *Streptomyces griseus* in relation to the onset of morphological differentiation, Okamoto, S. et al, Feb. 7, 1999.

GenBank Accession No. E01358 for Production of L-Thereonine and L-Isoleucine, Katsumata, R. et al, Sep. 29, 1997.

GenBank Accession No. E01359 for Production of L-Thereonine and L-Isoleucine, Katsumata, R. et al, Sep. 29, 1997.

GenBank Accession No. E01375 for *Tryptophan operon*, peptide and protein coded thereby, utilization of *Tryptophan operon* gene expression and producation ot *Tryptophan*, Matsui, K. et al, Sep. 29, 1997.

GenBank Accession No. E01376 for *Tryptophan operon*, Peptide and Protein Coded Thereby, Utilization of *Tryptophan operon* Gene Expression and Production of *Tryptophan*, Matsui, K. et al, Sep. 29, 1997.

GenBank Accession No. E01377 for *Tryptophan operon*, Peptide and Protein Coded Thereby, Utilization of *Tryptophan operon* Gene Expression and Production of *Tryptophan*, Matsui, K. et al, Sep. 29, 1997.

GenBank Accession No. E03937 for DNA fragment containing gene capable of coding biotin synthetase and its utilization, Hatakeyama, K. et al, Sep. 29, 1997.

GenBank Accession No. E04040 for Gene Coding Diaminopelargonic Acid Aminotransferase and Desthiobiotin Synthetase and its Utilization, Kohama, K. et al, Sep. 29, 1997.

GenBank Accession No. E04041 for Gene coding Diaminopelargonic Acid Aminotransferase and Desthiobiotin Synthetase and its Utilization, Kohama, K. et al, Sep. 29, 1997.

GenBank Accession No. E04307, Kurusu, Y. et al, "Gene DNA coding aspartase and utilization there." Sep. 29, 1997.

GenBank Accession No. E04376 for Gene Manifestation Controlling DNA, Katsumata, R. et al, Sep. 29, 1997.

GenBank Accession No. E04377 for Gene Manifestation Controlling DNA, Katsumata, R. et al, Sep. 29, 1997.

GenBank Accession No. E04484 for Production of L-Phenylalanine by Fermentation, Sotouchi, N. et al, Sep. 29, 1997.

GenBank Accession No. E05108 for Gene DNA Coding Aspartokinase and its Use, Fugono, N. et al, Sep. 29, 1997.

GenBank Accession No. E05112 for Gene DNA Coding Dihydrodipicolinic Acid Synthetase and its Use, Hatakeyama, K. et al, Sep. 29, 1997.

GenBank Accession No. E05776 for Gene DNA Diaminopimelic Acid Dehydrogenase and its Use, Kobayashi, M. et al, Sep. 29, 1997.

GenBank Accession No. E05779 for Gene DNA Coding Threonine Synthase and its Use, Kohama, K. et al, Sep. 29, 1997.

GenBank Accession No. E06110 for Production of L-Phenylalanine by Fermentation Method, Kikuchi, T. et al, Sep. 29, 1997.

GenBank Accession No. E06111 for Production of L-Phenylalanine by Fermentation Method, Kikuchi, T. et al, Sep. 29, 1997.

GenBank Accession No. E06146 for Gene Capable of Coding Acetohydroxy Acid Synthase and its, Inui, M. et al, Sep. 29, 1997.

GenBank Accession No. E06825 for Mutant Aspartokinase Gene, Sugimoto, M. et al, Sep. 29, 1997.

GenBank Accession No. E06826 for Mutant Aspartokinase Gene, Sugimoto, M. et al, Sep. 29, 1997.

GenBank Accession No. E06827 for Mutant Aspartokinase Gene, Sugimoto, M. et al, Sep. 29, 1997.

GenBank Accession No. E08177 for Genetic DNA Capable of Coding Aspartokinase Released from Feedback Inhibition and its Utilization, Sato, Y. et al, Sep. 29, 1997.

GenBank Accession No. E08178 for Genetic DNA Capable of Coding Aspartokinase Released from Feedback Inhibition and its Utilization, Sato, Y. et al, Sep. 29, 1997.

GenBank Accession No. E08179 for Genetic DNA Capable of Coding Aspartokinase Released from Feedback Inhibition and its Utilization, Sato, Y. et al, Sep. 29, 1997.

GenBank Accession No. E08180 for Genetic DNA Capable of Coding Aspartokinase Released from Feedback Inhibition and its Utilization, Sato, Y. et al, Sep. 29, 1997.

GenBank Accession No. E08181 for Genetic DNA Capable of Coding Aspartokinase Released from Feedback Inhibition and its Utilization, Sato, Y. et al, Sep. 29, 1997.

GenBank Accession No. E08182 for Genetic DNA Capable of Coding Aspartokinase Released from Feedback Inhibition and its Utilization, Sato, Y. et al, Sep. 29, 1997.

GenBank Accession No. E08232 for Gene DNA Coding Acetohydroxy Acid Isomeroreductase, Inui, M. et al, Sep. 29, 1997.

GenBank Accession No. E08234 for Gene DNA Coding for Translocation Machinery of Protein, Asai, Y. et al, Sep. 29, 1997.

GenBank Accession No. E08643 for DNA Fragment Having Promoter Function in Coryneform Bacterium, Hatakeyama, K. et al. Sep. 29, 1997.

GenBank Accession No. E08646 for DNA Fragment Having Promoter Function in Coryneform Bacterium, Hatakeyama, K. et al. Sep. 29, 1997.

GenBank Accession No. E08649, Kohama, K. et al, "DNA fragment having promoter function in coryneform bacterium." Sep. 29, 1997.

GenBank Accession No. E08900 for DNA Fragment Containing Gene Coding Dihyrodipicolinic Acid Reductase and Utilization Thereof, Madori, M. et al, Sep. 29, 1997.

GenBank Accession No. E08901 for DNA Fragment Containing Gene Coding Dihyrodipicolinic Acid Decarboxylase and Utilization Thereof, Madori, M. et al, Sep. 29, 1997.

GenBank Accession No. E12594 for Production of L-Tryptophan, Hatakeyama, K. et al, Sep. 29, 1997.

GenBank Accession No. E12758 for Amplification of Gene Using Artificial Transposon, Moriya, M. et al, Sep. 29, 1997.

GenBank Accession No. E12759 for Amplification of Gene Using Artificial Transposon, Moriya, M. et al, Sep. 29, 1997.

GenBank Accession No. E12760 for Amplification of Gene Using Artificial Transposon, Moriya, M. et al, Sep. 29, 1997.

GenBank Accession No. E12764 for Amplification of Gene Using Artificial Transposon, Moriya, M. et al, Sep. 29, 1997.

GenBank Accession No. E12767 for Amplification of Gene Using Artificial Transposon, Moriya, M. et al, Sep. 29, 1997.

GenBank Accession No. E12770 for Amplification of Gene Using Artificial Transposon, Moriya, M. et al, Sep. 29, 1997.

GenBank Accession No. E12773 for Amplification of Gene Using Artificial Transposon, Moriya, M. et al, Sep. 29, 1997.

GenBank Accession No. E13655 for Glucose-6-Phosphate Dehydrogenase and DNA Capable of Coding the Same, Hatakeyama, K. et al, Apr. 27, 1998.

GenBank Accession No. L01508, Mockel, B. et al, "Functional and structural analyses of threonine dehydratase from *Corynebacterium glutamicum*," *J. Bacteriol.*, vol. 174(24):8065-8072 (1992), Apr. 26, 1993.

GenBank Accession No. L07603 for the cloning and nucleotide sequence of a *Corynebacterium glutamicum* 3-deoxy-D-arabinoheptulosonate-7-phosphate synthase gene, Chen, C.C. et al, Apr. 26, 1993.

GenBank Accession No. L09232 for Isoleucine synthesis in *Corynebacterium glutamicum*: molecular analysis of the ilvB-ilvN-ilvC operon, Keilhauer, C. et al, Feb. 23, 1995.

GenBank Accession No. L18874 for *Bacillus subtilis* sucrose-specific enzyme II of the phosphotransferase system: expression in *Escherichia coli* and homology to enzymes II from enteric bacteria, Fouet, A. et al, Nov. 24, 1994.

GenBank Accession No. L27123 for Molecular characterization of aceB, a gene encoding malate synthase in *Corynebacterium glutamicum*, Lee, H.-S. et al, Jun. 8, 1995.

GenBank Accession No. L27126, Jetten, M.S., "Structural and functional analysis of pyruvate kinase from *Corynebacterium glutamicum*," *Appl. Environ. Microbiol.*, vol. 60(7):2501-2507 (1994), Dec. 7, 1994.

GenBank Accession No. L28760 for Molecular characterisation of acea, a gene encoding isocitrate lyase in *Corynebacterium glutamicum*, Lee, H.-S et al, Feb. 10, 1995.
GenBank Accession N. L35906, Oguiza, J.A., "Molecular cloning, DNA sequence analysis, and characterization of the *Corynebacterium diphtheria* dtxR homolog from *Brevibacterium lactofermentum*," *J. Bacteriol.*, vol. 177(2):465-467 (1995) Mar. 6, 1996.
GenBank Accession No. L78820, Eiglmeier, K. et al, "Use of an ordered cosmid library to deduce the genomic organization of *Mycobacterium laprae*," *Mol. Microbiol.*, vol. 7(2):197-206 (1993) Dec. 17, 2001.
GenBank Accession No. M13774, Follettie, M. T. et al, "Molecular cloning and nucleotide sequence of the *Corynebacterium glutamicum* pheA gene," *J. Bacteriol.*, vol. 167(2):695-702 (1986), Apr. 26, 1993.
GenBank Accession No. M16175 for Phylogenetic analysis of the coryneform bacteria by 5S rRNA sequences, Park, Y.H. et al, Apr. 27, 1993.
GenBank Accession No. M16663 for Structure and function of the trp operon control regions of *Brevibacterium lactofermentum*, a glutamic-acid producing bacterium, Sano, K. et al, Jun. 11, 2001.
GenBank Accession No. M16664 for Structure and function of the trp operon control regions of *Brevibacterium lactofermentum*, a glutamic-acid-producing bacterium, Sano, K. et al, Jun. 11, 2001.
GenBank Accession No. M25819 for Cloning and nucleotide sequence of the phosphoenolpyruvate carboxylase-coding gene of *Corynebacterium glutamicum* ATCC 13032, O'Regan, M. et al, Dec. 15, 1995.
GenBank Accession No. M85106 for Gram-positive bacteria with a high DNA G+C content are characterized by a common insertion within their 23S rRNA genes, Roller, C. et al, Apr. 26, 1993.
GenBank Accession No. M85107 for Gram-positive bacteria with a high DNA G+C content are characterized by a common insertion within their 23S rRNA genes, Roller, C. et al, Apr. 26, 1993.
GenBank Accession No. M85108 for Gram-positive bacteria with a high DNA G+C content are characterized by a common insertion within their 23S rRNA genes, Roller, C. et al, Apr. 26, 1993.
GenBank Accession No. M89931, Rossol, I. et al, "The *Corynebacterium glutamicum* aecD gene encodes a C-S lyase with alpha, beta-elimination activity that degrades aminoethylcysteine," *J. Bacteriol.*, vol. 174(9):2968-2977 (1992), Feb. 8, 2002.
GenBank Accession No. S59299 for Cloning of the trp gene cluster from a tryptophan-hyperproducing strain of *Corynebacterium glutamicum*: identification of a mutation in the trp leader sequence, Herry, D.M. et al, Apr. 13, 2001.
GenBank Accession No. S76966 for Insertion sequence typing of *Mycobacterium tuberculosis*: characterization of a widespread subtype with a single copy of IS6110, Fomukong, N.G. et al, May 11, 2005.
GenBank Accession No. U00016 for *Mycobacterium leprae*, Smith, D.R. et al, Mar. 1, 2004.
GenBank Accession No. U00018 for Smith, D.R., *Mycobacterium leprae*, Smith, D.R. et al, Mar. 1, 2004.
GenBank Accession No. U11545 for Complete nucleotide sequence of the *Corynebacterium glutamicum* ATCC 21850 trpD gene, O'Gara, J.P. et al, Jul. 8, 1994.
GenBank Accession No. U13922 for Cloning and characterization of a DNA region encoding a stress-sensitive restriction system from *Corynebacterium glutamicum* ATCC 13032 and analysis of its role in intergeneric conjugation with *Escherichia coli*, Schafer, A. et al, Feb. 3, 1998.
GenBank Accession No. U14965 for Molecular cloning and characterization of the recA gene from *Corynebacterium glutamicum* ASO19, Kerins, S.M. et al, Feb. 5, 1999.
GenBank Accession No. U31224, Ankri, S. et al, "Mutations in the *Corynebacterium glutamicum* proline biosynthetic pathway: a natural bypass of the proA step," *J. Bacteriol.*, vol. 178(15):4412-4419 (1996), Aug. 2, 1996.
GenBank Accession No. U31225, Ankri, S. et al, "Mutations in the *Corynebacterium glutamicum* proline biosynthetic pathway: a natural bypass of th proA step," *J. Bacteriol.*, vol. 178(15):4412-4419 (1996), Aug. 2, 1996.
GenBank Accession No. U31230, Ankri, S. et al, "Mutations in the *Corynebacterium glutamicum* proline biosynthetic pathway: a natural bypass of th proA step," *J. Bacteriol.*, vol. 178(15):4412-4419 (1996), Aug. 2, 1996.
GenBank Accession No. U31281 for Two new members of the bio B superfamily: cloning, sequencing and expression of bio B genes of *Methylobacillus flagellatum* and *Corynebacterium glutamicum*, Serebriiskii, I.G. et al, Nov. 21, 1996.
GenBank Accession No. U35023 for A *Corynebacterium glutamicum* gene encoding a two-domain protein similar to biotin carboxylases and biotin-carboxyl-carrier proteins, Jager, W. et al, Jan. 16, 1997.
GenBank Accession No. U43535 for A *Corynebacterium glutamicum* gene conferring multidrug resistance in the heterologous host *Escherichia coli*, Jager, W. et al, Apr. 9, 1997.
GenBank Accession No. U43536 for *Corynebacterium glutamicum*, Jager, W. et al, Mar. 13, 1997.
GenBank Accession No. U53587 for Utilization of IS1207 for insertional mutagenesis in Corynebacteria, Bonamy, C. et al, May 6, 1996.
GenBank Accession No. U89648 for *Corynebacterium glutamicum*, Kim, S.Y. et al, Mar. 30, 1999.
GenBank Accession No. X04960 for complete nucleotide and deduced amino acid sequences of the *Brevibacterium lactofermentum* tryptophan operon, Matsui, K. et al, Apr. 18, 2005.
GenBank Accession No. X07563 for Nucleotide sequence of the lysA gene of *Corynebacterium glutamicum* and possible mechanisms for modulation of its expression, Yeh, P. et al, Apr. 18, 2005.
GenBank Accession No. X14234 for The phosphoenolpyruvate carboxylase gene of *Corynebacterium glutamicum*: molecular cloning, nucleotide sequence, and expression, Eikmanns, B.J. et al, Apr. 18, 2005.
GenBank Accession No. X17313 for Molecular cloning, nucleotide sequence and fine-structural analysis of the *Corynebacterium glutamicum* fda gene: structural comparison of *C. glutamicum* fructose-1, 6-biphosphate aldolase to class I and Class II aldolases, von der Osten, C.H. et al, Apr. 18, 2005.
GenBank Accession No. X53993 for Nucleotide sequence of the dapA gene from *Corynebacterium glutamicum*, Bonnassie, S. et al, Apr. 18, 2005.
GenBank Accession No. X54223 for DNA sequence homology between att B-related sites of *Corynebacterium diphtheriae*, *Corynebacterium ulcerans*, *Corynebacterium glutamicum*, and the attP site of lambda-corynephage, Cianciotto, N. et al, Dec. 17, 1992.
GenBank Accession No. X54740 for Nucleotide sequence and organization of the upstream region of the *Corynebacterium glutamicum* lysA gene, Marcel, T. et al, Apr. 18, 2005.
GenBank Accession No. X55994 for Nucleotide sequence of the *Corynebacterium glutamicum* trpE gene, Heery, D.M. et al, Apr. 18, 2005.
GenBank Accession No. X56037 for The molecular structure of the *Corynebacterium glutamicum* threonine synthase gene, Han, K.S. et al, Apr. 18, 2005.
GenBank Accession No. X56075 for DNA sequence homology between att B-related sites of *Corynebacterium diphtheriae*, *Corynebacterium ulcerans*, *Corynebacterium glutamicum*, and the attP site of lambda-corynephage, Cianciotto, N. et al, Dec. 17, 1992.
GenBank Accession No. X57226 for Aspartokinase genes lysC alpha and lysC beta overlap and are adjacent to the aspartate beta-semialdehyde dehydrogenase asd *Corynebacterium glutamicum*, Kalinowski, J. et al, Apr. 18, 2005.
GenBank Accession No. X59403 for Identification, sequence analysis, and expression of a *Corynebacterium glutamicum* gene cluster encoding the three glycolytic enzymes glyceraldehyde-3-phosphate dehydrogenase, 3-phosphoglycerate kinase, and triosephosphate isomerase, Eikmanns, B.J. et al, Apr. 18, 2005.
GenBank Accession No. X59404, Bormann, E.R. et al, "Molecular analysis of the *Corynebacterium glutamicum* gbh gene encoding glutamate dehydrogenase," *Mol. Microbiol.*, vol. 6(3):317-326 (1992), Apr. 18, 2005.
GenBank Accession No. X60312 for Molecular analysis of the *Corynebacterium glutamicum* lysI gene involved in lysine uptake, Seep-Feldhaus, A.H. et al, Jan. 30, 1992.

GenBank Accession No. X66078 for Cloning and nucleotide sequence of the csp1 gene encoding PS1, one of the two major secreted proteins of *Corynebacterium glutamicum:* the deduced N-terminal region of PS1 is similar to the *Mycobacterium* antigen 85 complex, Joliff, G. et al, Jun. 30, 1993.

GenBank Accession No. X66112, Eikmanns, B.J. et al, "Nucleotide sequence, expression and transcriptional analysis of the *Corynecbacterium glutamicum* gltA gene encoding citrate synthase," *Microbiology,* vol. 140(pt. 8):1817-1828 (1994), Apr. 18, 2005.

GenBank Accession No. X67737 for *Corynebacterium glutamicum,* Eikmanns, B.J. et al, Apr. 18, 2005.

GenBank Accession No. X69103 for Characterization of the cspB gene encoding PS2, an ordered surface-layer protein in *Corynebacterium glutamicum,* Peyret, J.L. et al, Sep. 9, 2004.

GenBank Accession No. X69104 for Identification of IS1206, a *Corynebacterium glutamicum* IS3-related insertion sequence and phylogenetic analysis, Bonamy, C. et al, Sep. 9, 2004.

GenBank Accession No. X70584 for In vivo comparison of zidovudine resistance mutations in blood and CSF of HIV-1-infected patients, Wildemann, B. et al, Aug. 6, 1995.

GenBank Accession No. X70959 for Leucine synthesis in *Corynebacterium glutamicum:* enzyme activities, structure of leuA, and effect of leuA inactivation on lysine synthesis, Patek, M. et al, Sep. 9, 2004.

GenBank Accession No. X71489 for Cloning, sequence analysis, expression, and inactivation of the *Corynebacterium glutamicum* icd gene encoding isocitrate dehydrogenase and biochemical characterization of the enzyme, Eikmanns, B.J. et al, Apr. 18, 2005.

GenBank Accession No. X72855, Guyonvarch, A. et al, "Glutamate dehydrogenase (gdhA) gene." Apr. 18, 2005.

GenBank Accession No. X75083 for A sequence from a tryptophan-hyperproducing strain of *Corynebacterium glutamicum* encoding resistance to 5-methyltryophan, Heery, D.M. et al, Aug. 18, 1994.

GenBank Accession No. X75085 for Construction and characterization of recA mutant strains of *Corynebacterium glutamicum* and *Brevibacterium lactofermentum,* Fitzpatrick, R. et al, Apr. 18, 2005.

GenBank Accession No. X75504 for Characterization of the isocitrate lyase gene from *Corynebacterium glutamicum* and biochemical analysis of the enzyme, Reinscheid, D.J. et al, Apr. 18, 2005.

GenBank Accession No. X76875 for Phylogenetic relationships of Bacteria based on comparative sequence analysis of elongation factor Tu and ATP-synthase beta-subunit genes, Ludwig, W. et al, Oct. 27, 1994.

GenBank Accession No. X77034 for Phylogenetic relationships of Bacteria based on comparative sequence analysis of elongation factor Tu and ATP-synthase beta-subunit genes, Ludwig, W. et al, Apr. 18, 1994.

GenBank Accession No. X77384 for Nucleotide sequence of a recA gene from *Corynebacterium glutamicum,* Billman-Jacobe, H. et al, Apr. 18, 2005.

GenBank Accession No. X78491 for Malate synthase from *Corynebacterium glutamicum:* sequence analysis of the gene and biochemical characterization of the enzyme, Reinscheid, D.J. et al, Apr. 18, 2005.

GenBank Accession No. X80629 for Phylogenetic analysis of the genera *Rhodococcus* and *Norcardia* and evidence for the evolutionary origin of the genus *Nocardia* from within the radiation of *Rhodococcus* species, Rainey, F.A. et al, Apr. 1, 2004.

GenBank Accession No. X81191 for Structure of the gluABCD cluster encoding the glutamate uptake system of *Corynebacterium glutamicum,* Kronemeyer, W. et al, Apr. 18, 2005.

GenBank Accession No. X81379, Wehrmann, A. et al, "Analysis of different DNA fragments of *Corynebacterium glutamicum* complementing dapE of *Escherichia coli,*" *Microbiology,* vol. 140(pt. 12):3349-3356 (1994), Feb. 25, 2003.

GenBank Accession No. X82061 for Phylogeny of the genus *Corynebacterium* deduced from analysis of small-subunit ribosomal DNA sequences, Ruimy, R. et al, Nov. 10, 1995.

GenBank Accession No. X82928 for Multicopy suppression by asd gene and osmotic stress-dependent complementation by heterologous proA in proA mutants, Serebrijski, I. et al, Apr. 18, 2005.

GenBank Accession No. X82929 for Multicopy suppression by asd gene and osmotic stress-dependent complementation by heterologous proA in proA mutants, Serebrijski, I. et al, Apr. 18, 2005.

GenBank Accession No. X84257 for Phylogenetic analysis of the genus *Corynebacterium* based on 16S rRNA gene sequences, Pascual, C. et al, Jan. 9, 2004.

GenBank Accession No. X85965, Wehrmann, A. et al, "Functional analysis of sequences adjacent to dapE of *Corynebacterium glutamicum* reveals the presence of aroP, which encodes the aromatic amino acid transporter," *J. Bacteriol.,* vol. 177(20):5991-5993 (1995).

GenBank Accession No. X86157, Sakanyan, V. et al, "Genes and enzymes of the acetyl cycle of arginine biosynthesis in *Corynebacterium glutamicum:* enzyme evolution in the early steps of the arginine pathway," *Microbiology,* vol. 142(Pt. 1):99-108 (1996), Apr. 18, 2005.

GenBank Accession No. X86780 for The biosynthetic gene cluster for the polyketide immunosuppressant rapamycin, Schwecke, T. et al, Apr. 18, 2005.

GenBank Accession No. X89084 for Cloning, sequence analysis, expression and inactivation of the *Corynebacterium glutamicum* pta-ack operon encoding phosphotransacetylase and acetate kinase, Reinscheid, D.J. et al, Apr. 18, 2005.

GenBank Accession No. X89850 for Genetic characterization of site-specific integration functions of phi AAU2 infecting '*Arthrobacter aureus*' C70, Le Marrec, C. et al, Aug. 8, 1996.

GenBank Accession No. X90356 for Promoters from *Corynebacterium glutamicum:* cloning, molecular analysis and search for a consensus motif, Patek, M. et al, Nov. 4, 1996.

GenBank Accession No. X90357 for Promoters from *Corynebacterium glutamicum:* cloning, molecular analysis and search for a consensus motif, Patek, M. et al, Nov. 4, 1996.

GenBank Accession No. X90358 for Promoters from *Corynebacterium glutamicum:* cloning, molecular analysis and search for a consensus motif, Patek, M. et al, Nov. 4, 1996.

GenBank Accession No. X90359 for Promoters from *Corynebacterium glutamicum:* cloning, molecular analysis and search for a consensus motif, Patek, M. et al, Nov. 4, 1996.

GenBank Accession No. X90360 for Promoters from *Corynebacterium glutamicum:* cloning, molecular analysis and search for a consensus motif, Patek, M. et al, Nov. 4, 1996.

GenBank Accession No. X90361 for Promoters from *Corynebacterium glutamicum:* cloning, molecular analysis and search for a consensus motif, Patek, M. et al, Nov. 4, 1996.

GenBank Accession No. X90362 for Promoters from *Corynebacterium glutamicum:* cloning, molecular analysis and search for a consensus motif, Patek, M. et al, Nov. 4, 1996.

GenBank Accession No. X90363 for Promoters from *Corynebacterium glutamicum:* cloning, molecular analysis and search for a consensus motif, Patek, M. et al, Nov. 4, 1996.

GenBank Accession No. X90364 for Promoters from *Corynebacterium glutamicum:* cloning, molecular analysis and search for a consensus motif, Patek, M. et al, Nov. 4, 1996.

GenBank Accession No. X90365 for Promoters from *Corynebacterium glutamicum:* cloning, molecular analysis and search for a consensus motif, Patek, M. et al, Nov. 4, 1996.

GenBank Accession No. X90366 for Promoters from *Corynebacterium glutamicum:* cloning, molecular analysis and search for a consensus motif, Patek, M. et al, Nov. 4, 1996.

GenBank Accession No. X90367 for Promoters from *Corynebacterium glutamicum:* cloning, molecular analysis and search for a consensus motif, Patek, M. et al, Nov. 4, 1996.

GenBank Accession No. X90368 for Promoters from *Corynebacterium glutamicum:* cloning, molecular analysis and search for a consensus motif, Patek, M. et al, Nov. 4, 1996.

GenBank Accession No. X93513, Siewe, R.M. et al, "Functional and genetic characterization of the (methyl)ammonium uptake carrier of *Corynebacterium glutamicum,*" *J. Biol. Chem.,* vol. 271(10):5398-5403 (1996), May 29, 1996.

GenBank Accesssion No. X93514 for Isolation, characterization, and expression of the *Corynebacterium glutamicum* betP gene, encoding the transport system for the compatible solute glycine, Peter, H. et al, Sep. 8, 1997.

GenBank Accession No. X95649 for Identification and transcriptional analysis of the dapB-ORF2-dapA-ORF4 operon of *Corynebacterium glutamicum,* encoding two enzymes involved in L-lysine synthesis, Patek, M. et al, Dec. 21, 2000.

GenBank Accession No. X96471 for A new type of transporter with a new type of cellular function: L-lysine export from *Corynebacterium glutamicum,* Vrljic, M. et al, Apr. 18, 2005.

GenBank Accession No. X96580, Sahm, H. et al, "D-Pantothenate synthesis in *Corynebacterium glutamicum* and use of panBC and genes encoding L-valine synthesis for D-pantothenate overproduction," *Appl. Environ. Microbiol.,* vol. 65(5):1973-1979 (1999), Apr. 18, 2005.

GenBank Accession No. X96962 for Utilisation of IS1207 for insertional mutagenesis in Corynbacteria, Bonamy, C. et al, Jul. 7, 2002.

GenBank Accession No. X99289 for Cloning, sequencing and expression of the gene encoding elongation factor P in the amino-acid producer *Brevibacterium lactofermentum (Corynebacterium glutamicum* ATCC 13869), Ramos, A. et al, Sep. 9, 2004.

GenBank Accession No. Y00140 for Nucleotide sequence of the homoserine kinase (thr B) gene of *Brevibacterium lactofermentum,* Mateos, L.M. et al, Sep. 12, 1993.

GenBank Accession No. Y00151 for Nucleotide sequence of the meso-diaminopimelate D-dehydrogenase gene from *Corynebacterium glutamicum,* Ishino, S. et al, Sep. 12, 1993.

GenBank Accession No. Y00476 for Nucleotide sequence of the homoserine dehydrogenase (thr A) gene of *Brevibacterium lactofermentum,* Mateos, L.M. et al, May 5, 1993.

GenBank Accession No. Y00546 for Nucleotide sequence and fine structural analysis of the *Corynebacterium glutamicum* hom-thrB operon, Peoples, O.P. et al, Sep. 12, 1993.

GenBank Accession No. Y08964 for Identification, characterization, and chromosomal organization of the ftsZ gene from *Brevibacterium lactofermentum,* Honrubia, M.P. et al, Apr. 18, 2005.

GenBank Accession No. Y09163 for Isolation of the putP gene of *Corynebacterium glutamicum* and characterization of a low-affinity uptake system for compatible solutes, Peter, H. et al, Sep. 8, 1997.

GenBank Accession No. Y09548 for Pyruvate carboxylase from *Corynebacterium glutamicum:* characterization, expression and inactivation of the pyc gene, Peters-Wendisch, P.G. et al, Apr. 18, 2005.

GenBank Accession No. Y09578 for Analysis of the leuB gene from *Corynebacterium glutamicum,* Patek, M. et al, Apr. 18, 2005.

GenBank Accession No. Y12472 for Site-specific integration of corynephage phi16: the construction of an integration vector, Moreau, S. et al, Mar. 5, 1999.

GenBank Accession No. Y12537 for *Corynebacterium glutamicum* is equipped with four secondary carriers for compatible solutes: identification, sequencing, and characterization of the proline/glycine betaine carrier, EctP, Peter, H. et al, Nov. 17, 1998.

GenBank Accession No. Y13221 for Isolation of the *Corynebacterium glutamicum* glnA gene encoding glutamine synthetase I, Jakoby, M. et al, Aug. 28, 1997.

GenBank Accession No. Y13627 for Identification of novel intergenic repetitive units in a mycobacterial two-component system operon, Supply, P. et al, Apr. 18, 2005.

GenBank Accession No. Y16642 for *Corynebacterium glutamicum,* Schwinde, J. et al, Apr. 18, 2005.

GenBank Accession No. Y18059 for Analysis of the integration functions of phi304L: an integrase module among corynephages, Moreau, S. et al, Sep. 29, 1999.

GenBank Accession No. Z21501 for A gene encoding arginly-tRNA synthetase is located in the upstream region of the lysA gene in *Brevibacterium lactofermentum:* regulation of argS-lysA cluster expression by arginine, Oguiza, J.A. et al, Apr. 18, 2005.

GenBank Accession No. Z21502 for A cluster of three genes (dapA, orf2, and dapB) *Brevibacterium lactofermentum* encodes dihydrodipicolinate synthase, dihydrodipicolinate reductase, and a third polypeptide of unknown function, Pisabarro, A. et al, Aug. 16, 1993.

GenBank Accession No. Z29563 for Analysis and expression of the thrC gene of *Brevibacterium lactofermentum* and characterization of the encoded threonine synthase, Malumbres, M. et al, Apr. 18, 2005.

GenBank Accession No. Z46753 for Phylogeny of *Corynebacterium glutamicum,* Chun, J. et al, Nov. 21, 1994.

GenBank Accession No. Z49822 for Multiple sigma factor genes in *Brevibacterium lactofermentum:* characterization of sigA and sigB, Oguiza, J.A. et al, Apr. 18, 2005.

GenBank Accession No. Z49823 for The galE gene encoding the UDP-galactose 4-epimerase of *Brevibacterium lactofermentum* is coupled transcriptionally to the dmdR gene, Oguiza, J.A. et al, Apr. 18, 2005.

GenBank Accession No. Z49824 for Multiple sigma factor genes in *Brevibacterium lactofermentum:* characterization of sigA and sigB, Oguiza, J.A. et al, Apr. 18, 2005.

GenBank Accession No. Z66534 for Cloning and characterization of an IS-like element present in the genome of *Brevibacterium lactofermentum* ATCC 13869, Correia, A. et al, Jul. 7, 2002.

GenBank Accession No. Z77162 for Deciphering the biology of *Mycobacterium tuberculosis* from the complete genome sequence, Cole, S.T. et al, Sep. 2, 2002.

GenBank Accession No. Z80226 for Deciphering the biology of *Mycobacterium tuberculosis* from the complete genome sequence, Cole, S.T. et al, Sep. 2, 2002.

GenBank Accession No. Z81368, Cole, S.T. et al, "Deciphering the biology of *Mycobacterium tuberculosis* from the complete genome sequence," *Nature,* vol. 393(6685):537-544 (1998) Sep. 2, 2002.

GenBank Accession No. I40899, Maley, F. et al., "Human deoxycytidylate deaminase gene," May 13, 1997.

GenBank Accession No. I40900, Maley, F. et al., "Human deoxycytidylate deaminase gene," May 13, 1997.

GenBank Accession No. L39874, Weiner, K.X. et al., "Chromosomal location and structural organization of the human deoxycytidylate deaminase gene," J. Biol. Chem., vol. 270(32):18727-18729 (1995) Aug. 11, 1995.

Erdmann, A. et al., "Lysine secretion by *Corynebacterium glutamicum* wild type: regulation of secretion carrier activity," *Appl. Microbiol. Biotechnol.,* vol. 42:604-610 (1994).

Jetten, Mike S.M. et al., "Metabolic Engineering of *Corynebacterium glutamicum,*" *Annals of the New York Academy of Sciences,* vol. 721:12-29 (1994).

Krämer, Reinhard, "Genetic and physiological approaches for the production of amino acids," *Journal of Biotechnology,* vol. 45:1-21 (1996).

Parche, Stephan et al., "*Corynebacterium glutamicum:* a Dissection of the PTS," *J. Mol. Microbiol. Biotechnol.,* vol. 3(3):423-428 (2001).

Postma, P.W. et al., "Phosphoenolpyruvate:Carbohydrate Phosphotransferase Systems of Bacteria," *Microbiological Reviews,* vol. 57(3):543-594 (1993).

* cited by examiner

SEQUENCE LISTING

<160> NUMBER OF SEQ ID NOS: 34

<210> SEQ ID NO 1
<211> LENGTH: 1527
<212> TYPE: DNA
<213> ORGANISM: Corynebacterium glutamicum
<220> FEATURE:
<221> NAME/KEY: CDS
<222> LOCATION: (101)..(1504)
<223> OTHER INFORMATION: RXS00315

<400> SEQUENCE: 1

```
ctcatggcat ctgcgccgtt cgcgttcttg ccagtgttgg ttggtttcac cgcaaccaag        60
cgtttcggcg caatgagtt  cctgggcgcc gcgtattggt atg gcg atg gtg ttc         115
                                            Met Ala Met Val Phe
                                              1               5 ccg agc ttg gtg aac ggc tac gac gtg gcc gcc acc atg gct gcg ggc         163
Pro Ser Leu Val Asn Gly Tyr Asp Val Ala Ala Thr Met Ala Ala Gly
         10                  15                  20 gaa atg cca atg tgg tcc ctg ttt ggt tta gat gtt gcc caa gcc ggt         211
Glu Met Pro Met Trp Ser Leu Phe Gly Leu Asp Val Ala Gln Ala Gly
     25                  30                  35 tac cag ggc acc gtg ctt cct gtg ctg gtg gtt tct tgg att ctg gca         259
Tyr Gln Gly Thr Val Leu Pro Val Leu Val Val Ser Trp Ile Leu Ala
 40                  45                  50 acg atc gag aag ttc ctg cac aag cga ctc aag ggc act gca gac ttc         307
Thr Ile Glu Lys Phe Leu His Lys Arg Leu Lys Gly Thr Ala Asp Phe
             55                  60                  65 ctg atc act cca gtg ctg acg ttg ctg ctc acc gga ttc ctt aca ttc         355
Leu Ile Thr Pro Val Leu Thr Leu Leu Leu Thr Gly Phe Leu Thr Phe
 70                  75                  80                  85 atc gcc att ggc cca gca atg cgc tgg gtg ggc gat gtg ctg gca cac         403
Ile Ala Ile Gly Pro Ala Met Arg Trp Val Gly Asp Val Leu Ala His
                 90                  95                 100 ggt cta cag gga ctt tat gat ttc ggt ggt cca gtc ggc ggt ctg ctc         451
Gly Leu Gln Gly Leu Tyr Asp Phe Gly Gly Pro Val Gly Gly Leu Leu
            105                 110                 115 ttc ggt ctg gtc tac tca cca atc gtc atc act ggt ctg cac cag tcc         499
Phe Gly Leu Val Tyr Ser Pro Ile Val Ile Thr Gly Leu His Gln Ser
        120                 125                 130 ttc ccg cca att gag ctg gag ctg ttt aac cag ggt gga tcc ttc atc         547
Phe Pro Pro Ile Glu Leu Glu Leu Phe Asn Gln Gly Gly Ser Phe Ile
    135                 140                 145 ttc gca acg gca tct atg gct aat atc gcc cag ggt gcg gca tgt ttg         595
Phe Ala Thr Ala Ser Met Ala Asn Ile Ala Gln Gly Ala Ala Cys Leu
150                 155                 160                 165 gca gtg ttc ttc ctg gcg aag agt gaa aag ctc aag ggc ctt gca ggt         643
Ala Val Phe Phe Leu Ala Lys Ser Glu Lys Leu Lys Gly Leu Ala Gly
                170                 175                 180 gct tca ggt gtc tcc gct gtt ctt ggt att acg gag cct gcg atc ttc         691
Ala Ser Gly Val Ser Ala Val Leu Gly Ile Thr Glu Pro Ala Ile Phe
            185                 190                 195 ggt gtg aac ctt cgc ctg cgc tgg ccg ttc ttc atc ggt atc ggt acc         739
Gly Val Asn Leu Arg Leu Arg Trp Pro Phe Phe Ile Gly Ile Gly Thr
        200                 205                 210 gca gct atc ggt ggc gct ttg att gca ctc ttt aat atc aag gca gtt         787
Ala Ala Ile Gly Gly Ala Leu Ile Ala Leu Phe Asn Ile Lys Ala Val
    215                 220                 225 gcg ttg ggc gct gca ggt ttc ttg ggt gtt gtt tct att gat gct cca         835
```

```
Ala Leu Gly Ala Ala Gly Phe Leu Gly Val Val Ser Ile Asp Ala Pro
230                 235                 240                 245 gat atg gtc atg ttc ttg gtg tgt gca gtt gtt acc ttc ttc atc gca    883
Asp Met Val Met Phe Leu Val Cys Ala Val Val Thr Phe Phe Ile Ala
                250                 255                 260 ttc ggc gca gcg att gct tat ggc ctt tac ttg gtt cgc cgc aac ggc    931
Phe Gly Ala Ala Ile Ala Tyr Gly Leu Tyr Leu Val Arg Arg Asn Gly
                265                 270                 275 agc att gat cca gat gca acc gct gct cca gtg cct gca gga acg acc    979
Ser Ile Asp Pro Asp Ala Thr Ala Ala Pro Val Pro Ala Gly Thr Thr
                280                 285                 290 aaa gcc gaa gca gaa gca ccc gca gaa ttt tca aac gat tcc acc atc   1027
Lys Ala Glu Ala Glu Ala Pro Ala Glu Phe Ser Asn Asp Ser Thr Ile
            295                 300                 305 atc cag gca cct ttg acc ggt gaa gct att gca ctg agc agc gtc agc   1075
Ile Gln Ala Pro Leu Thr Gly Glu Ala Ile Ala Leu Ser Ser Val Ser
310                 315                 320                 325 gat gcc atg ttt gcc agc gga aag ctt ggc tcg ggc gtt gcc atc gtc   1123
Asp Ala Met Phe Ala Ser Gly Lys Leu Gly Ser Gly Val Ala Ile Val
                330                 335                 340 cca acc aag ggg cag tta gtt tct ccg gtg agt gga aag att gtg gtg   1171
Pro Thr Lys Gly Gln Leu Val Ser Pro Val Ser Gly Lys Ile Val Val
                345                 350                 355 gca ttc cca tct ggc cat gct ttc gca gtt cgc acc aag gct gag gat   1219
Ala Phe Pro Ser Gly His Ala Phe Ala Val Arg Thr Lys Ala Glu Asp
                360                 365                 370 ggt tcc aat gtg gat atc ttg atg cac att ggt ttc gac aca gta aac   1267
Gly Ser Asn Val Asp Ile Leu Met His Ile Gly Phe Asp Thr Val Asn
375                 380                 385 ctc aac ggc acg cac ttt aac ccg ctg aag aag cag ggc gat gaa gtc   1315
Leu Asn Gly Thr His Phe Asn Pro Leu Lys Lys Gln Gly Asp Glu Val
390                 395                 400                 405 aaa gca ggg gag ctg ctg tgt gaa ttc gat att gat gcc att aag gct   1363
Lys Ala Gly Glu Leu Leu Cys Glu Phe Asp Ile Asp Ala Ile Lys Ala
                410                 415                 420 gca ggt tat gag gta acc acg ccg att gtt gtt tcg aat tac aag aaa   1411
Ala Gly Tyr Glu Val Thr Thr Pro Ile Val Val Ser Asn Tyr Lys Lys
                425                 430                 435 acc gga cct gta aac act tac ggt ttg ggc gaa att gaa gcg gga gcc   1459
Thr Gly Pro Val Asn Thr Tyr Gly Leu Gly Glu Ile Glu Ala Gly Ala
                440                 445                 450 aac ctg ctc aac gtc gca aag aaa gaa gcg gtg cca gca aca cca       1504
Asn Leu Leu Asn Val Ala Lys Lys Glu Ala Val Pro Ala Thr Pro
        455                 460                 465 taagttgaaa ccttgagtgt tcg                                         1527

<210> SEQ ID NO 2
<211> LENGTH: 468
<212> TYPE: PRT
<213> ORGANISM: Corynebacterium glutamicum

<400> SEQUENCE: 2

Met Ala Met Val Phe Pro Ser Leu Val Asn Gly Tyr Asp Val Ala Ala
1               5                   10                  15

Thr Met Ala Ala Gly Glu Met Pro Met Trp Ser Leu Phe Gly Leu Asp
            20                  25                  30

Val Ala Gln Ala Gly Tyr Gln Gly Thr Val Leu Pro Val Leu Val Val
        35                  40                  45

Ser Trp Ile Leu Ala Thr Ile Glu Lys Phe Leu His Lys Arg Leu Lys
```

```
              50                  55                  60
Gly Thr Ala Asp Phe Leu Ile Thr Pro Val Leu Thr Leu Leu Leu Thr
 65                  70                  75                  80

Gly Phe Leu Thr Phe Ile Ala Ile Gly Pro Ala Met Arg Trp Val Gly
                 85                  90                  95

Asp Val Leu Ala His Gly Leu Gln Gly Leu Tyr Asp Phe Gly Gly Pro
            100                 105                 110

Val Gly Gly Leu Leu Phe Gly Leu Val Tyr Ser Pro Ile Val Ile Thr
            115                 120                 125

Gly Leu His Gln Ser Phe Pro Pro Ile Glu Leu Glu Leu Phe Asn Gln
130                 135                 140

Gly Gly Ser Phe Ile Phe Ala Thr Ala Ser Met Ala Asn Ile Ala Gln
145                 150                 155                 160

Gly Ala Ala Cys Leu Ala Val Phe Phe Leu Ala Lys Ser Glu Lys Leu
                165                 170                 175

Lys Gly Leu Ala Gly Ala Ser Gly Val Ser Ala Val Leu Gly Ile Thr
            180                 185                 190

Glu Pro Ala Ile Phe Gly Val Asn Leu Arg Leu Arg Trp Pro Phe Phe
            195                 200                 205

Ile Gly Ile Gly Thr Ala Ala Ile Gly Gly Ala Leu Ile Ala Leu Phe
            210                 215                 220

Asn Ile Lys Ala Val Ala Leu Gly Ala Ala Gly Phe Leu Gly Val Val
225                 230                 235                 240

Ser Ile Asp Ala Pro Asp Met Val Met Phe Leu Val Cys Ala Val Val
                245                 250                 255

Thr Phe Phe Ile Ala Phe Gly Ala Ala Ile Ala Tyr Gly Leu Tyr Leu
                260                 265                 270

Val Arg Arg Asn Gly Ser Ile Asp Pro Asp Ala Thr Ala Ala Pro Val
            275                 280                 285

Pro Ala Gly Thr Thr Lys Ala Glu Ala Glu Ala Pro Ala Glu Phe Ser
290                 295                 300

Asn Asp Ser Thr Ile Ile Gln Ala Pro Leu Thr Gly Glu Ala Ile Ala
305                 310                 315                 320

Leu Ser Ser Val Ser Asp Ala Met Phe Ala Ser Gly Lys Leu Gly Ser
                325                 330                 335

Gly Val Ala Ile Val Pro Thr Lys Gly Gln Leu Val Ser Pro Val Ser
            340                 345                 350

Gly Lys Ile Val Val Ala Phe Pro Ser Gly His Ala Phe Ala Val Arg
            355                 360                 365

Thr Lys Ala Glu Asp Gly Ser Asn Val Asp Ile Leu Met His Ile Gly
370                 375                 380

Phe Asp Thr Val Asn Leu Asn Gly Thr His Phe Asn Pro Leu Lys Lys
385                 390                 395                 400

Gln Gly Asp Glu Val Lys Ala Gly Glu Leu Leu Cys Glu Phe Asp Ile
                405                 410                 415

Asp Ala Ile Lys Ala Ala Gly Tyr Glu Val Thr Thr Pro Ile Val Val
            420                 425                 430

Ser Asn Tyr Lys Lys Thr Gly Pro Val Asn Thr Tyr Gly Leu Gly Glu
            435                 440                 445

Ile Glu Ala Gly Ala Asn Leu Leu Asn Val Ala Lys Lys Glu Ala Val
        450                 455                 460

Pro Ala Thr Pro
465
```

<210> SEQ ID NO 3
<211> LENGTH: 1109
<212> TYPE: DNA
<213> ORGANISM: Corynebacterium glutamicum
<220> FEATURE:
<221> NAME/KEY: CDS
<222> LOCATION: (1)..(1086)
<223> OTHER INFORMATION: FRXA00315

<400> SEQUENCE: 3

| | | | | | | | | | | | | | | | | |
|---|---|---|---|---|---|---|---|---|---|---|---|---|---|---|---|---|
| tat | gat | ttc | ggc | ggt | cca | gtc | ggc | ggt | ctg | ctc | ttc | ggt | ctg | gtc | tac | 48 |
| Tyr | Asp | Phe | Gly | Gly | Pro | Val | Gly | Gly | Leu | Leu | Phe | Gly | Leu | Val | Tyr | |
| 1 | | | | 5 | | | | | 10 | | | | | 15 | | |
| tca | cca | atc | gtc | atc | act | ggt | ctg | cac | cag | tcc | ttc | ccg | cca | att | gag | 96 |
| Ser | Pro | Ile | Val | Ile | Thr | Gly | Leu | His | Gln | Ser | Phe | Pro | Pro | Ile | Glu | |
| | | | 20 | | | | | 25 | | | | | 30 | | | |
| ctg | gag | ctg | ttt | aac | cag | ggt | gga | tcc | ttc | atc | ttc | gca | acg | gca | tct | 144 |
| Leu | Glu | Leu | Phe | Asn | Gln | Gly | Gly | Ser | Phe | Ile | Phe | Ala | Thr | Ala | Ser | |
| | | 35 | | | | | 40 | | | | | 45 | | | | |
| atg | gct | aat | atc | gcc | cag | ggt | gcg | gca | tgt | ttg | gca | gtg | ttc | ttc | ctg | 192 |
| Met | Ala | Asn | Ile | Ala | Gln | Gly | Ala | Ala | Cys | Leu | Ala | Val | Phe | Phe | Leu | |
| 50 | | | | | 55 | | | | | 60 | | | | | | |
| gcg | aag | agt | gaa | aag | ctc | aag | ggc | ctt | gca | ggt | gct | tca | ggt | gtc | tcc | 240 |
| Ala | Lys | Ser | Glu | Lys | Leu | Lys | Gly | Leu | Ala | Gly | Ala | Ser | Gly | Val | Ser | |
| 65 | | | | 70 | | | | | 75 | | | | | 80 | | |
| gct | gtt | ctt | ggt | att | acg | gag | cct | gcg | atc | ttc | ggt | gtg | aac | ctt | cgc | 288 |
| Ala | Val | Leu | Gly | Ile | Thr | Glu | Pro | Ala | Ile | Phe | Gly | Val | Asn | Leu | Arg | |
| | | | | 85 | | | | | 90 | | | | | 95 | | |
| ctg | cgc | tgg | ccg | ttc | ttc | atc | ggt | atc | ggt | acc | gca | gct | atc | ggt | ggc | 336 |
| Leu | Arg | Trp | Pro | Phe | Phe | Ile | Gly | Ile | Gly | Thr | Ala | Ala | Ile | Gly | Gly | |
| | | | 100 | | | | | 105 | | | | | 110 | | | |
| gct | ttg | att | gca | ctc | ttt | aat | atc | aag | gca | gtt | gcg | ttg | ggc | gct | gca | 384 |
| Ala | Leu | Ile | Ala | Leu | Phe | Asn | Ile | Lys | Ala | Val | Ala | Leu | Gly | Ala | Ala | |
| | | 115 | | | | | 120 | | | | | 125 | | | | |
| ggt | ttc | ttg | ggt | gtt | gtt | tct | att | gat | gct | cca | gat | atg | gtc | atg | ttc | 432 |
| Gly | Phe | Leu | Gly | Val | Val | Ser | Ile | Asp | Ala | Pro | Asp | Met | Val | Met | Phe | |
| 130 | | | | | 135 | | | | | 140 | | | | | | |
| ttg | gtg | tgt | gca | gtt | gtt | acc | ttc | ttc | atc | gca | ttc | ggc | gca | gcg | att | 480 |
| Leu | Val | Cys | Ala | Val | Val | Thr | Phe | Phe | Ile | Ala | Phe | Gly | Ala | Ala | Ile | |
| 145 | | | | 150 | | | | | 155 | | | | | 160 | | |
| gct | tat | ggc | ctt | tac | ttg | gtt | cgc | cgc | aac | ggc | agc | att | gat | cca | gat | 528 |
| Ala | Tyr | Gly | Leu | Tyr | Leu | Val | Arg | Arg | Asn | Gly | Ser | Ile | Asp | Pro | Asp | |
| | | | | 165 | | | | | 170 | | | | | 175 | | |
| gca | acc | gct | gct | cca | gtg | cct | gca | gga | acg | acc | aaa | gcc | gaa | gca | gaa | 576 |
| Ala | Thr | Ala | Ala | Pro | Val | Pro | Ala | Gly | Thr | Thr | Lys | Ala | Glu | Ala | Glu | |
| | | | 180 | | | | | 185 | | | | | 190 | | | |
| gca | ccc | gca | gaa | ttt | tca | aac | gat | tcc | acc | atc | atc | cag | gca | cct | ttg | 624 |
| Ala | Pro | Ala | Glu | Phe | Ser | Asn | Asp | Ser | Thr | Ile | Ile | Gln | Ala | Pro | Leu | |
| | | 195 | | | | | 200 | | | | | 205 | | | | |
| acc | ggt | gaa | gct | att | gca | ctg | agc | agc | gtc | agc | gat | gcc | atg | ttt | gcc | 672 |
| Thr | Gly | Glu | Ala | Ile | Ala | Leu | Ser | Ser | Val | Ser | Asp | Ala | Met | Phe | Ala | |
| | | 210 | | | | | 215 | | | | | 220 | | | | |
| agc | gga | aag | ctt | ggc | tcg | ggc | gtt | gcc | atc | gtc | cca | acc | aag | ggg | cag | 720 |
| Ser | Gly | Lys | Leu | Gly | Ser | Gly | Val | Ala | Ile | Val | Pro | Thr | Lys | Gly | Gln | |
| 225 | | | | 230 | | | | | 235 | | | | | 240 | | |
| tta | gtt | tct | ccg | gtg | agt | gga | aag | att | gtg | gtg | gca | ttc | cca | tct | ggc | 768 |
| Leu | Val | Ser | Pro | Val | Ser | Gly | Lys | Ile | Val | Val | Ala | Phe | Pro | Ser | Gly | |
| | | | | 245 | | | | | 250 | | | | | 255 | | |
| cat | gct | ttc | gca | gtt | cgc | acc | aag | gct | gag | gat | ggt | tcc | aat | gtg | gat | 816 |
| His | Ala | Phe | Ala | Val | Arg | Thr | Lys | Ala | Glu | Asp | Gly | Ser | Asn | Val | Asp | |
| | | | 260 | | | | | 265 | | | | | 270 | | | |

```
atc ttg atg cac att ggt ttc gac aca gta aac ctc aac ggc acg cac    864
Ile Leu Met His Ile Gly Phe Asp Thr Val Asn Leu Asn Gly Thr His
    275                 280                 285 ttt aac ccg ctg aag aag cag ggc gat gaa gtc aaa gca ggg gag ctg    912
Phe Asn Pro Leu Lys Lys Gln Gly Asp Glu Val Lys Ala Gly Glu Leu
290                 295                 300 ctg tgt gaa ttc gat att gat gcc att aag gct gca ggt tat gag gta    960
Leu Cys Glu Phe Asp Ile Asp Ala Ile Lys Ala Ala Gly Tyr Glu Val
305                 310                 315                 320 acc acg ccg att gtt gtt tcg aat tac aag aaa acc gga cct gta aac   1008
Thr Thr Pro Ile Val Val Ser Asn Tyr Lys Lys Thr Gly Pro Val Asn
                325                 330                 335 act tac ggt ttg ggc gaa att gaa gcg gga gcc aac ctg ctc aac gtc   1056
Thr Tyr Gly Leu Gly Glu Ile Glu Ala Gly Ala Asn Leu Leu Asn Val
            340                 345                 350 gca aag aaa gaa gcg gtg cca gca aca cca taagttgaaa ccttgagtgt     1106
Ala Lys Lys Glu Ala Val Pro Ala Thr Pro
        355                 360 tcg                                                               1109

<210> SEQ ID NO 4
<211> LENGTH: 362
<212> TYPE: PRT
<213> ORGANISM: Corynebacterium glutamicum

<400> SEQUENCE: 4

Tyr Asp Phe Gly Gly Pro Val Gly Gly Leu Leu Phe Gly Leu Val Tyr
1               5                   10                  15

Ser Pro Ile Val Ile Thr Gly Leu His Gln Ser Phe Pro Pro Ile Glu
            20                  25                  30

Leu Glu Leu Phe Asn Gln Gly Gly Ser Phe Ile Phe Ala Thr Ala Ser
        35                  40                  45

Met Ala Asn Ile Ala Gln Gly Ala Ala Cys Leu Ala Val Phe Phe Leu
    50                  55                  60

Ala Lys Ser Glu Lys Leu Lys Gly Leu Ala Gly Ala Ser Gly Val Ser
65                  70                  75                  80

Ala Val Leu Gly Ile Thr Glu Pro Ala Ile Phe Gly Val Asn Leu Arg
                85                  90                  95

Leu Arg Trp Pro Phe Phe Ile Gly Ile Gly Thr Ala Ala Ile Gly Gly
            100                 105                 110

Ala Leu Ile Ala Leu Phe Asn Ile Lys Ala Val Ala Leu Gly Ala Ala
        115                 120                 125

Gly Phe Leu Gly Val Val Ser Ile Asp Ala Pro Asp Met Val Met Phe
    130                 135                 140

Leu Val Cys Ala Val Val Thr Phe Phe Ile Ala Phe Gly Ala Ala Ile
145                 150                 155                 160

Ala Tyr Gly Leu Tyr Leu Val Arg Arg Asn Gly Ser Ile Asp Pro Asp
                165                 170                 175

Ala Thr Ala Ala Pro Val Pro Ala Gly Thr Thr Lys Ala Glu Ala Glu
            180                 185                 190

Ala Pro Ala Glu Phe Ser Asn Asp Ser Thr Ile Ile Gln Ala Pro Leu
        195                 200                 205

Thr Gly Glu Ala Ile Ala Leu Ser Ser Val Ser Asp Ala Met Phe Ala
    210                 215                 220

Ser Gly Lys Leu Gly Ser Gly Val Ala Ile Val Pro Thr Lys Gly Gln
225                 230                 235                 240
```

```
Leu Val Ser Pro Val Ser Gly Lys Ile Val Ala Phe Pro Ser Gly
                245                 250                 255

His Ala Phe Ala Val Arg Thr Lys Ala Glu Asp Gly Ser Asn Val Asp
                260                 265                 270

Ile Leu Met His Ile Gly Phe Asp Thr Val Asn Leu Asn Gly Thr His
                275                 280                 285

Phe Asn Pro Leu Lys Lys Gln Gly Asp Glu Val Lys Ala Gly Glu Leu
                290                 295                 300

Leu Cys Glu Phe Asp Ile Asp Ala Ile Lys Ala Ala Gly Tyr Glu Val
305                 310                 315                 320

Thr Thr Pro Ile Val Val Ser Asn Tyr Lys Lys Thr Gly Pro Val Asn
                325                 330                 335

Thr Tyr Gly Leu Gly Glu Ile Glu Ala Gly Ala Asn Leu Leu Asn Val
                340                 345                 350

Ala Lys Lys Glu Ala Val Pro Ala Thr Pro
                355                 360

<210> SEQ ID NO 5
<211> LENGTH: 372
<212> TYPE: DNA
<213> ORGANISM: Corynebacterium glutamicum
<220> FEATURE:
<221> NAME/KEY: CDS
<222> LOCATION: (101)..(349)
<223> OTHER INFORMATION: RXA01503

<400> SEQUENCE: 5
gtatcctcaa aggccttcta gctgttgcag ctgcagcgca ctcggtggat acgacatcca      60
cgacctatca aattctttat gctgcaggcg atgccttttc atg ttc ttg gca gtc     115
                                              Met Phe Leu Ala Val
                                                1               5 att ttg gcg att act gcg gct cgt aaa ttc ggt gcc aat gtc ttt aca     163
Ile Leu Ala Ile Thr Ala Ala Arg Lys Phe Gly Ala Asn Val Phe Thr
            10                  15                  20 tca gtc gca ctc gct ggt gca ttg ctg cac aca cag ctt cag gca gta     211
Ser Val Ala Leu Ala Gly Ala Leu Leu His Thr Gln Leu Gln Ala Val
        25                  30                  35 acc gtg ttg gtt gac ggt gaa ctc cag tcg atg act ctg gtg gct ttc     259
Thr Val Leu Val Asp Gly Glu Leu Gln Ser Met Thr Leu Val Ala Phe
    40                  45                  50 caa aag gct ggt aat gac gtc acc ttc ctg ggc att cca gtg gtg ctg     307
Gln Lys Ala Gly Asn Asp Val Thr Phe Leu Gly Ile Pro Val Val Leu
55                  60                  65 cag ttg gcg ttg cat gta gcg agt ttg atg aag ttg tcg cga              349
Gln Leu Ala Leu His Val Ala Ser Leu Met Lys Leu Ser Arg
70                  75                  80 taagaggagg ggcgtgtcgg tct                                             372

<210> SEQ ID NO 6
<211> LENGTH: 83
<212> TYPE: PRT
<213> ORGANISM: Corynebacterium glutamicum

<400> SEQUENCE: 6

Met Phe Leu Ala Val Ile Leu Ala Ile Thr Ala Ala Arg Lys Phe Gly
 1               5                  10                  15

Ala Asn Val Phe Thr Ser Val Ala Leu Ala Gly Ala Leu Leu His Thr
                20                  25                  30
```

```
Gln Leu Gln Ala Val Thr Val Leu Val Asp Gly Glu Leu Gln Ser Met
         35                  40                  45

Thr Leu Val Ala Phe Gln Lys Ala Gly Asn Asp Val Thr Phe Leu Gly
 50                  55                  60

Ile Pro Val Val Leu Gln Leu Ala Leu His Val Ala Ser Leu Met Lys
 65                  70                  75                  80

Leu Ser Arg

<210> SEQ ID NO 7
<211> LENGTH: 2187
<212> TYPE: DNA
<213> ORGANISM: Corynebacterium glutamicum
<220> FEATURE:
<221> NAME/KEY: CDS
<222> LOCATION: (101)..(2164)
<223> OTHER INFORMATION: RXN01299

<400> SEQUENCE: 7
cgactgcggc gtctcttcct ggcactacca ttcctcgtcc tgaccaactc gccacagctg     60
gtgcaacggt cacccaagtc aaaggattga aagaatcagc atg aat agc gta aat    115
                                              Met Asn Ser Val Asn
                                                1               5 aat tcc tcg ctt gtc cgg ctg gat gtc gat ttc ggc gac tcc acc acg    163
Asn Ser Ser Leu Val Arg Leu Asp Val Asp Phe Gly Asp Ser Thr Thr
             10                  15                  20 gat gtc atc aac aac ctt gcc act gtt att ttc gac gct ggc cga gct    211
Asp Val Ile Asn Asn Leu Ala Thr Val Ile Phe Asp Ala Gly Arg Ala
         25                  30                  35 tcc tcc gcc gac gcc ctt gcc aaa gac gcg ctg gat cgt gaa gca aag    259
Ser Ser Ala Asp Ala Leu Ala Lys Asp Ala Leu Asp Arg Glu Ala Lys
     40                  45                  50 tcc ggc acc ggc gtt cct ggt caa gtt gct atc ccc cac tgc cgt tcc    307
Ser Gly Thr Gly Val Pro Gly Gln Val Ala Ile Pro His Cys Arg Ser
 55                  60                  65 gaa gcc gta tct gtc cct acc ttg ggc ttt gct cgc ctg agc aag ggt    355
Glu Ala Val Ser Val Pro Thr Leu Gly Phe Ala Arg Leu Ser Lys Gly
 70                  75                  80                  85 gtg gac ttc agc gga cct gat ggc gat gcc aac ttg gtg ttc ctc att    403
Val Asp Phe Ser Gly Pro Asp Gly Asp Ala Asn Leu Val Phe Leu Ile
             90                  95                 100 gca gca cct gct ggc ggc ggc aaa gag cac ctg aag atc ctg tcc aag    451
Ala Ala Pro Ala Gly Gly Gly Lys Glu His Leu Lys Ile Leu Ser Lys
         105                 110                 115 ctt gct cgc tcc ttg gtg aag aag gat ttc atc aag gct ctg cag gaa    499
Leu Ala Arg Ser Leu Val Lys Lys Asp Phe Ile Lys Ala Leu Gln Glu
     120                 125                 130 gcc acc acc gag cag gaa atc gtc gac gtt gtc gat gcc gtg ctc aac    547
Ala Thr Thr Glu Gln Glu Ile Val Asp Val Val Asp Ala Val Leu Asn
 135                 140                 145 cca gca cca aaa acc acc gag cca gct gca gct ccg gct gcg gcg gcg    595
Pro Ala Pro Lys Thr Thr Glu Pro Ala Ala Ala Pro Ala Ala Ala Ala
 150                 155                 160                 165 gtt gct gag agt ggg gcg gcg tcg aca agc gtt act cgt atc gtg gca    643
Val Ala Glu Ser Gly Ala Ala Ser Thr Ser Val Thr Arg Ile Val Ala
             170                 175                 180 atc acc gca tgc cca acc ggt atc gca cac acc tac atg gct gcg gat    691
Ile Thr Ala Cys Pro Thr Gly Ile Ala His Thr Tyr Met Ala Ala Asp
         185                 190                 195 tcc ctg acg caa aac gcg gaa ggc cgc gat gat gtg gaa ctc gtt gtg    739
Ser Leu Thr Gln Asn Ala Glu Gly Arg Asp Asp Val Glu Leu Val Val
```

```
                200                 205                 210
gag act cag ggc tct tcc gct gtc acc cca gtc gat ccg aag atc atc    787
Glu Thr Gln Gly Ser Ser Ala Val Thr Pro Val Asp Pro Lys Ile Ile
    215                 220                 225 gaa gct gcc gac gcc gtc atc ttc gcc acc gac gtg gga gtt aaa gac    835
Glu Ala Ala Asp Ala Val Ile Phe Ala Thr Asp Val Gly Val Lys Asp
230                 235                 240                 245 cgc gag cgt ttc gct ggc aag cca gtc att gaa tcc ggc gtc aag cgc    883
Arg Glu Arg Phe Ala Gly Lys Pro Val Ile Glu Ser Gly Val Lys Arg
            250                 255                 260 gcg atc aat gag cca gcc aag atg atc gac gag gcc atc gca gcc tcc    931
Ala Ile Asn Glu Pro Ala Lys Met Ile Asp Glu Ala Ile Ala Ala Ser
        265                 270                 275 aag aac cca aac gcc cgc aag gtt tcc ggt tcc ggt gtc gcg gca tct    979
Lys Asn Pro Asn Ala Arg Lys Val Ser Gly Ser Gly Val Ala Ala Ser
    280                 285                 290 gct gaa acc acc ggc gag aag ctc ggc tgg ggc aag cgc atc cag cag    1027
Ala Glu Thr Thr Gly Glu Lys Leu Gly Trp Gly Lys Arg Ile Gln Gln
295                 300                 305 gca gtc atg acc ggc gtg tcc tac atg gtt cca ttc gta gct gcc ggc    1075
Ala Val Met Thr Gly Val Ser Tyr Met Val Pro Phe Val Ala Ala Gly
310                 315                 320                 325 ggc ctc ctg ttg gct ctc ggc ttc gca ttc ggt gga tac gac atg gcg    1123
Gly Leu Leu Leu Ala Leu Gly Phe Ala Phe Gly Gly Tyr Asp Met Ala
            330                 335                 340 aac ggc tgg caa gca atc gcc acc cag ttc tct ctg acc aac ctg cca    1171
Asn Gly Trp Gln Ala Ile Ala Thr Gln Phe Ser Leu Thr Asn Leu Pro
        345                 350                 355 ggc aac acc gtc gat gtt gac ggc gtg gcc atg acc ttc gag cgt tca    1219
Gly Asn Thr Val Asp Val Asp Gly Val Ala Met Thr Phe Glu Arg Ser
    360                 365                 370 ggc ttc ctg ttg tac ttc ggc gca gtc ctg ttc gcc acc ggc caa gca    1267
Gly Phe Leu Leu Tyr Phe Gly Ala Val Leu Phe Ala Thr Gly Gln Ala
375                 380                 385 gcc atg ggc ttc atc gtg gca gcc ctg tct ggc tac acc gca tac gca    1315
Ala Met Gly Phe Ile Val Ala Ala Leu Ser Gly Tyr Thr Ala Tyr Ala
390                 395                 400                 405 ctt gct gga cgc cca ggc atc gcg ccg ggc ttc gtc ggt ggc gcc atc    1363
Leu Ala Gly Arg Pro Gly Ile Ala Pro Gly Phe Val Gly Gly Ala Ile
            410                 415                 420 tcc gtc acc atc ggc gct ggc ttc att ggt ggt ctg gtt acc ggt atc    1411
Ser Val Thr Ile Gly Ala Gly Phe Ile Gly Gly Leu Val Thr Gly Ile
        425                 430                 435 ttg gct ggt ctc att gcc ctg tgg att ggc tcc tgg aag gtg cca cgc    1459
Leu Ala Gly Leu Ile Ala Leu Trp Ile Gly Ser Trp Lys Val Pro Arg
    440                 445                 450 gtg gtg cag tca ctg atg cct gtg gtc atc atc ccg cta ctt acc tca    1507
Val Val Gln Ser Leu Met Pro Val Val Ile Ile Pro Leu Leu Thr Ser
455                 460                 465 gtg gtt gtt ggt ctc gtc atg tac ctc ctg ctg ggt cgc cca ctc gca    1555
Val Val Val Gly Leu Val Met Tyr Leu Leu Leu Gly Arg Pro Leu Ala
470                 475                 480                 485 tcc atc atg act ggt ttg cag gac tgg cta tcg tca atg tcc gga agc    1603
Ser Ile Met Thr Gly Leu Gln Asp Trp Leu Ser Ser Met Ser Gly Ser
            490                 495                 500 tcc gcc atc ttg ctg ggt atc atc ttg ggc ctc atg atg tgt ttc gac    1651
Ser Ala Ile Leu Leu Gly Ile Ile Leu Gly Leu Met Met Cys Phe Asp
        505                 510                 515 ctc ggc gga cca gta aac aag gca gcc tac ctc ttt ggt acc gca ggc    1699
Leu Gly Gly Pro Val Asn Lys Ala Ala Tyr Leu Phe Gly Thr Ala Gly
```

```
Leu Gly Gly Pro Val Asn Lys Ala Ala Tyr Leu Phe Gly Thr Ala Gly
        520                 525                 530 ctg tct acc ggc gac caa gct tcc atg gaa atc atg gcc gcg atc atg      1747
Leu Ser Thr Gly Asp Gln Ala Ser Met Glu Ile Met Ala Ala Ile Met
535                 540                 545 gca gct ggc atg gtc cca cca atc gcg ttg tcc att gct acc ctg ctg      1795
Ala Ala Gly Met Val Pro Pro Ile Ala Leu Ser Ile Ala Thr Leu Leu
550                 555                 560                 565 cgc aag aag ctg ttc acc cca gca gag caa gaa aac ggc aag tct tcc      1843
Arg Lys Lys Leu Phe Thr Pro Ala Glu Gln Glu Asn Gly Lys Ser Ser
                570                 575                 580 tgg ctg ctt ggc ctg gca ttc gtc tcc gaa ggt gcc atc cca ttc gcc      1891
Trp Leu Leu Gly Leu Ala Phe Val Ser Glu Gly Ala Ile Pro Phe Ala
            585                 590                 595 gca gct gac cca ttc cgt gtg atc cca gca atg atg gct ggc ggt gca      1939
Ala Ala Asp Pro Phe Arg Val Ile Pro Ala Met Met Ala Gly Gly Ala
        600                 605                 610 acc act ggt gca atc tcc atg gca ctg ggc gtc ggc tct cgg gct cca      1987
Thr Thr Gly Ala Ile Ser Met Ala Leu Gly Val Gly Ser Arg Ala Pro
615                 620                 625 cac ggc ggt atc ttc gtg gtc tgg gca atc gaa cca tgg tgg ggc tgg      2035
His Gly Gly Ile Phe Val Val Trp Ala Ile Glu Pro Trp Trp Gly Trp
630                 635                 640                 645 ctc atc gca ctt gca gca ggc acc atc gtg tcc acc atc gtt gtc atc      2083
Leu Ile Ala Leu Ala Ala Gly Thr Ile Val Ser Thr Ile Val Val Ile
                650                 655                 660 gca ctg aag cag ttc tgg cca aac aag gcc gtc gct gca gaa gtc gcg      2131
Ala Leu Lys Gln Phe Trp Pro Asn Lys Ala Val Ala Ala Glu Val Ala
            665                 670                 675 aag caa gaa gca caa caa gca gct gta aac gca taatcggacc ttgacccgat    2184
Lys Gln Glu Ala Gln Gln Ala Ala Val Asn Ala
        680                 685 gtc                                                                  2187

<210> SEQ ID NO 8
<211> LENGTH: 688
<212> TYPE: PRT
<213> ORGANISM: Corynebacterium glutamicum

<400> SEQUENCE: 8

Met Asn Ser Val Asn Ser Ser Leu Val Arg Leu Asp Val Asp Phe
1               5                   10                  15

Gly Asp Ser Thr Thr Asp Val Ile Asn Asn Leu Ala Thr Val Ile Phe
                20                  25                  30

Asp Ala Gly Arg Ala Ser Ser Ala Asp Ala Leu Ala Lys Asp Ala Leu
            35                  40                  45

Asp Arg Glu Ala Lys Ser Gly Thr Gly Val Pro Gly Gln Val Ala Ile
        50                  55                  60

Pro His Cys Arg Ser Glu Ala Val Ser Val Pro Thr Leu Gly Phe Ala
65                  70                  75                  80

Arg Leu Ser Lys Gly Val Asp Phe Ser Gly Pro Asp Gly Asp Ala Asn
                85                  90                  95

Leu Val Phe Leu Ile Ala Ala Pro Ala Gly Gly Lys Glu His Leu
            100                 105                 110

Lys Ile Leu Ser Lys Leu Ala Arg Ser Leu Val Lys Lys Asp Phe Ile
        115                 120                 125

Lys Ala Leu Gln Glu Ala Thr Thr Glu Gln Glu Ile Val Asp Val Val
    130                 135                 140
```

-continued

```
Asp Ala Val Leu Asn Pro Ala Pro Lys Thr Thr Glu Pro Ala Ala Ala
145                 150                 155                 160

Pro Ala Ala Ala Val Ala Glu Ser Gly Ala Ala Ser Thr Ser Val
            165                 170                 175

Thr Arg Ile Val Ala Ile Thr Ala Cys Pro Thr Gly Ile Ala His Thr
            180                 185                 190

Tyr Met Ala Ala Asp Ser Leu Thr Gln Asn Ala Glu Gly Arg Asp Asp
            195                 200                 205

Val Glu Leu Val Val Glu Thr Gln Gly Ser Ser Ala Val Thr Pro Val
        210                 215                 220

Asp Pro Lys Ile Ile Glu Ala Asp Ala Val Ile Phe Ala Thr Asp
225                 230                 235                 240

Val Gly Val Lys Asp Arg Glu Arg Phe Ala Gly Lys Pro Val Ile Glu
            245                 250                 255

Ser Gly Val Lys Arg Ala Ile Asn Glu Pro Ala Lys Met Ile Asp Glu
            260                 265                 270

Ala Ile Ala Ala Ser Lys Asn Pro Asn Ala Arg Lys Val Ser Gly Ser
        275                 280                 285

Gly Val Ala Ala Ser Ala Glu Thr Thr Gly Glu Lys Leu Gly Trp Gly
        290                 295                 300

Lys Arg Ile Gln Gln Ala Val Met Thr Gly Val Ser Tyr Met Val Pro
305                 310                 315                 320

Phe Val Ala Ala Gly Gly Leu Leu Ala Leu Gly Phe Ala Phe Gly
            325                 330                 335

Gly Tyr Asp Met Ala Asn Gly Trp Gln Ala Ile Ala Thr Gln Phe Ser
            340                 345                 350

Leu Thr Asn Leu Pro Gly Asn Thr Val Asp Val Asp Gly Val Ala Met
            355                 360                 365

Thr Phe Glu Arg Ser Gly Phe Leu Leu Tyr Phe Gly Ala Val Leu Phe
        370                 375                 380

Ala Thr Gly Gln Ala Ala Met Gly Phe Ile Val Ala Ala Leu Ser Gly
385                 390                 395                 400

Tyr Thr Ala Tyr Ala Leu Ala Gly Arg Pro Gly Ile Ala Pro Gly Phe
            405                 410                 415

Val Gly Gly Ala Ile Ser Val Thr Ile Gly Ala Gly Phe Ile Gly Gly
            420                 425                 430

Leu Val Thr Gly Ile Leu Ala Gly Leu Ile Ala Leu Trp Ile Gly Ser
            435                 440                 445

Trp Lys Val Pro Arg Val Val Gln Ser Leu Met Pro Val Val Ile Ile
    450                 455                 460

Pro Leu Leu Thr Ser Val Val Gly Leu Val Met Tyr Leu Leu Leu
465                 470                 475                 480

Gly Arg Pro Leu Ala Ser Ile Met Thr Gly Leu Gln Asp Trp Leu Ser
            485                 490                 495

Ser Met Ser Gly Ser Ser Ala Ile Leu Leu Gly Ile Ile Leu Gly Leu
        500                 505                 510

Met Met Cys Phe Asp Leu Gly Gly Pro Val Asn Lys Ala Ala Tyr Leu
        515                 520                 525

Phe Gly Thr Ala Gly Leu Ser Thr Gly Asp Gln Ala Ser Met Glu Ile
        530                 535                 540

Met Ala Ala Ile Met Ala Ala Gly Met Val Pro Pro Ile Ala Leu Ser
545                 550                 555                 560
```

-continued

```
Ile Ala Thr Leu Leu Arg Lys Lys Leu Phe Thr Pro Ala Glu Gln Glu
            565                 570                 575

Asn Gly Lys Ser Ser Trp Leu Leu Gly Leu Ala Phe Val Ser Glu Gly
        580                 585                 590

Ala Ile Pro Phe Ala Ala Ala Asp Pro Phe Arg Val Ile Pro Ala Met
    595                 600                 605

Met Ala Gly Gly Ala Thr Thr Gly Ala Ile Ser Met Ala Leu Gly Val
610                 615                 620

Gly Ser Arg Ala Pro His Gly Gly Ile Phe Val Val Trp Ala Ile Glu
625                 630                 635                 640

Pro Trp Trp Gly Trp Leu Ile Ala Leu Ala Ala Gly Thr Ile Val Ser
                645                 650                 655

Thr Ile Val Val Ile Ala Leu Lys Gln Phe Trp Pro Asn Lys Ala Val
            660                 665                 670

Ala Ala Glu Val Ala Lys Gln Glu Ala Gln Gln Ala Ala Val Asn Ala
        675                 680                 685
```

<210> SEQ ID NO 9
<211> LENGTH: 464
<212> TYPE: DNA
<213> ORGANISM: Corynebacterium glutamicum
<220> FEATURE:
<221> NAME/KEY: CDS
<222> LOCATION: (1)..(441)
<223> OTHER INFORMATION: FRXA01299

<400> SEQUENCE: 9

```
atg gaa atc atg gcc gcg atc atg gca gct ggc atg gtc cca cca atc       48
Met Glu Ile Met Ala Ala Ile Met Ala Ala Gly Met Val Pro Pro Ile
 1               5                  10                  15 gcg ttg tcc att gct acc ctg ctg cgc aag aag ctg ttc acc cca gca       96
Ala Leu Ser Ile Ala Thr Leu Leu Arg Lys Lys Leu Phe Thr Pro Ala
             20                  25                  30 gag caa gaa aac ggc aag tct tcc tgg ctg ctt ggc ctg gca ttc gtc      144
Glu Gln Glu Asn Gly Lys Ser Ser Trp Leu Leu Gly Leu Ala Phe Val
         35                  40                  45 tcc gaa ggt gcc atc cca ttc gcc gca gct gac cca ttc cgt gtg atc      192
Ser Glu Gly Ala Ile Pro Phe Ala Ala Ala Asp Pro Phe Arg Val Ile
     50                  55                  60 cca gca atg atg gct ggc ggt gca acc act ggt gca atc tcc atg gca      240
Pro Ala Met Met Ala Gly Gly Ala Thr Thr Gly Ala Ile Ser Met Ala
 65                  70                  75                  80 ctg ggc gtc ggc tct cgg gct cca cac ggc ggt atc ttc gtg gtc tgg      288
Leu Gly Val Gly Ser Arg Ala Pro His Gly Gly Ile Phe Val Val Trp
                 85                  90                  95 gca atc gaa cca tgg tgg ggc tgg ctc atc gca ctt gca gca ggc acc      336
Ala Ile Glu Pro Trp Trp Gly Trp Leu Ile Ala Leu Ala Ala Gly Thr
            100                 105                 110 atc gtg tcc acc atc gtt gtc atc gca ctg aag cag ttc tgg cca aac      384
Ile Val Ser Thr Ile Val Val Ile Ala Leu Lys Gln Phe Trp Pro Asn
        115                 120                 125 aag gcc gtc gct gca gaa gtc gcg aag caa gaa gca caa caa gca gct      432
Lys Ala Val Ala Ala Glu Val Ala Lys Gln Glu Ala Gln Gln Ala Ala
    130                 135                 140 gta aac gca taatcggacc ttgacccgat gtc                                 464
Val Asn Ala
145
```

<210> SEQ ID NO 10
<211> LENGTH: 147

<212> TYPE: PRT
<213> ORGANISM: Corynebacterium glutamicum

<400> SEQUENCE: 10

```
Met Glu Ile Met Ala Ala Ile Met Ala Ala Gly Met Val Pro Pro Ile
 1               5                  10                  15

Ala Leu Ser Ile Ala Thr Leu Leu Arg Lys Lys Leu Phe Thr Pro Ala
            20                  25                  30

Glu Gln Glu Asn Gly Lys Ser Ser Trp Leu Leu Gly Leu Ala Phe Val
        35                  40                  45

Ser Glu Gly Ala Ile Pro Phe Ala Ala Asp Pro Phe Arg Val Ile
    50                  55                  60

Pro Ala Met Met Ala Gly Gly Ala Thr Thr Gly Ala Ile Ser Met Ala
65                  70                  75                  80

Leu Gly Val Gly Ser Arg Ala Pro His Gly Gly Ile Phe Val Val Trp
                85                  90                  95

Ala Ile Glu Pro Trp Trp Gly Trp Leu Ile Ala Leu Ala Ala Gly Thr
            100                 105                 110

Ile Val Ser Thr Ile Val Val Ile Ala Leu Lys Gln Phe Trp Pro Asn
        115                 120                 125

Lys Ala Val Ala Ala Glu Val Ala Lys Gln Glu Ala Gln Gln Ala Ala
    130                 135                 140

Val Asn Ala
145
```

<210> SEQ ID NO 11
<211> LENGTH: 580
<212> TYPE: DNA
<213> ORGANISM: Corynebacterium glutamicum
<220> FEATURE:
<221> NAME/KEY: CDS
<222> LOCATION: (101)..(580)
<223> OTHER INFORMATION: FRXA01883

<400> SEQUENCE: 11

```
cgactgcggc gtctcttcct ggcactacca ttcctcgtcc tgaccaactc gccacagctg      60
gtgcaacggt cacccaagtc aaaggattga agaatcagc atg aat agc gta aat      115
                                            Met Asn Ser Val Asn
                                             1               5 aat tcc tcg ctt gtc cgg ctg gat gtc gat ttc ggc gac tcc acc acg      163
Asn Ser Ser Leu Val Arg Leu Asp Val Asp Phe Gly Asp Ser Thr Thr
            10                  15                  20 gat gtc atc aac aac ctt gcc act gtt att ttc gac gct ggc cga gct      211
Asp Val Ile Asn Asn Leu Ala Thr Val Ile Phe Asp Ala Gly Arg Ala
        25                  30                  35 tcc tcc gcc gac gcc ctt gcc aaa gac gcg ctg gat cgt gaa gca aag      259
Ser Ser Ala Asp Ala Leu Ala Lys Asp Ala Leu Asp Arg Glu Ala Lys
    40                  45                  50 tcc ggc acc ggc gtt cct ggt caa gtt gct atc ccc cac tgc cgt tcc      307
Ser Gly Thr Gly Val Pro Gly Gln Val Ala Ile Pro His Cys Arg Ser
55                  60                  65 gaa gcc gta tct gtc cct acc ttg ggc ttt gct cgc ctg agc aag ggt      355
Glu Ala Val Ser Val Pro Thr Leu Gly Phe Ala Arg Leu Ser Lys Gly
                70                  75                  80                  85 gtg gac ttc agc gga cct gat ggc gat gcc aac ttg gtg ttc ctc att      403
Val Asp Phe Ser Gly Pro Asp Gly Asp Ala Asn Leu Val Phe Leu Ile
            90                  95                  100 gca gca cct gct ggc ggc ggc aaa gag cac ctg aag atc ctg tcc aag      451
Ala Ala Pro Ala Gly Gly Gly Lys Glu His Leu Lys Ile Leu Ser Lys
```

```
ctt gct cgc tcc ttg gtg aag aag gat ttc atc aag gct ctg cag gaa    499
Leu Ala Arg Ser Leu Val Lys Lys Asp Phe Ile Lys Ala Leu Gln Glu
        120                 125                 130 gcc acc acc gag cag gaa atc gtc gac gtt gtc gat gcc gtc ctc aac    547
Ala Thr Thr Glu Gln Glu Ile Val Asp Val Val Asp Ala Val Leu Asn
    135                 140                 145 cca gca cca aaa aac cac cga gcc agc tgc agc                         580
Pro Ala Pro Lys Asn His Arg Ala Ser Cys Ser
150                 155                 160

<210> SEQ ID NO 12
<211> LENGTH: 160
<212> TYPE: PRT
<213> ORGANISM: Corynebacterium glutamicum

<400> SEQUENCE: 12

Met Asn Ser Val Asn Ser Ser Leu Val Arg Leu Asp Val Asp Phe
 1               5                  10                  15

Gly Asp Ser Thr Thr Asp Val Ile Asn Asn Leu Ala Thr Val Ile Phe
                20                  25                  30

Asp Ala Gly Arg Ala Ser Ser Ala Asp Ala Leu Ala Lys Asp Ala Leu
            35                  40                  45

Asp Arg Glu Ala Lys Ser Gly Thr Gly Val Pro Gly Gln Val Ala Ile
        50                  55                  60

Pro His Cys Arg Ser Glu Ala Val Ser Val Pro Thr Leu Gly Phe Ala
    65                  70                  75                  80

Arg Leu Ser Lys Gly Val Asp Phe Ser Gly Pro Asp Gly Asp Ala Asn
                85                  90                  95

Leu Val Phe Leu Ile Ala Ala Pro Ala Gly Gly Lys Glu His Leu
                100                 105                 110

Lys Ile Leu Ser Lys Leu Ala Arg Ser Leu Val Lys Lys Asp Phe Ile
            115                 120                 125

Lys Ala Leu Gln Glu Ala Thr Thr Glu Gln Glu Ile Val Asp Val Val
        130                 135                 140

Asp Ala Val Leu Asn Pro Ala Pro Lys Asn His Arg Ala Ser Cys Ser
145                 150                 155                 160

<210> SEQ ID NO 13
<211> LENGTH: 631
<212> TYPE: DNA
<213> ORGANISM: Corynebacterium glutamicum
<220> FEATURE:
<221> NAME/KEY: CDS
<222> LOCATION: (77)..(631)
<223> OTHER INFORMATION: FRXA01889

<400> SEQUENCE: 13
accgagccag ctgcagctcc ggctgcggcg gccggttgtt aagagtgggg cggcgtcgac    60
aagcgttact cgtatc gtg gca atc acc gca tgc cca acc ggt atc gca cac   112
                  Val Ala Ile Thr Ala Cys Pro Thr Gly Ile Ala His
                   1               5                  10 acc tac atg gct gcg gat tcc ctg acg caa aac gcg gaa ggc cgc gat   160
Thr Tyr Met Ala Ala Asp Ser Leu Thr Gln Asn Ala Glu Gly Arg Asp
            15                  20                  25 gat gtg gaa ctc gtt gtg gag act cag ggc tct tcc gct gtc acc cca   208
Asp Val Glu Leu Val Val Glu Thr Gln Gly Ser Ser Ala Val Thr Pro
        30                  35                  40 gtc gat ccg aag atc atc gaa gct gcc gac gcc gtc atc ttc gcc acc   256
```

```
                Val Asp Pro Lys Ile Ile Glu Ala Ala Asp Ala Val Ile Phe Ala Thr
                 45                  50                  55                  60 gac gtg gga gtt aaa gac cgc gag cgt ttc gct ggc aag cca gtc att           304
Asp Val Gly Val Lys Asp Arg Glu Arg Phe Ala Gly Lys Pro Val Ile
                 65                  70                  75 gaa tcc ggc gtc aag cgc gcg atc aat gag cca gcc aag atg atc gac           352
Glu Ser Gly Val Lys Arg Ala Ile Asn Glu Pro Ala Lys Met Ile Asp
         80                  85                  90 gag gcc atc gca gcc tcc aag aac cca aac gcc cgc aag gtt tcc ggt           400
Glu Ala Ile Ala Ala Ser Lys Asn Pro Asn Ala Arg Lys Val Ser Gly
     95                 100                 105 tcc ggt gtc gcg gca tct gct gaa acc acc ggc gag aag ctc ggc tgg           448
Ser Gly Val Ala Ala Ser Ala Glu Thr Thr Gly Glu Lys Leu Gly Trp
 110                 115                 120 ggc aag cgc atc cag cag gca gtc atg acc ggc gtg tcc tac atg gtt           496
Gly Lys Arg Ile Gln Gln Ala Val Met Thr Gly Val Ser Tyr Met Val
125             130                 135                 140 cca ttc gta gct gcc ggc ggc ctc ctg ttg gct ctc ggc ttc gca ttc           544
Pro Phe Val Ala Ala Gly Gly Leu Leu Leu Ala Leu Gly Phe Ala Phe
                145                 150                 155 ggt gga tac gac atg gcg aac ggc tgg caa gca atc gcc acc cag ttc           592
Gly Gly Tyr Asp Met Ala Asn Gly Trp Gln Ala Ile Ala Thr Gln Phe
            160                 165                 170 tct ctg acc aac ctg cca ggc aac acc gtc gat gtt gac                       631
Ser Leu Thr Asn Leu Pro Gly Asn Thr Val Asp Val Asp
        175                 180                 185

<210> SEQ ID NO 14
<211> LENGTH: 185
<212> TYPE: PRT
<213> ORGANISM: Corynebacterium glutamicum

<400> SEQUENCE: 14

Val Ala Ile Thr Ala Cys Pro Thr Gly Ile Ala His Thr Tyr Met Ala
 1               5                  10                  15

Ala Asp Ser Leu Thr Gln Asn Ala Glu Gly Arg Asp Asp Val Glu Leu
             20                  25                  30

Val Val Glu Thr Gln Gly Ser Ser Ala Val Thr Pro Val Asp Pro Lys
         35                  40                  45

Ile Ile Glu Ala Ala Asp Ala Val Ile Phe Ala Thr Asp Val Gly Val
     50                  55                  60

Lys Asp Arg Glu Arg Phe Ala Gly Lys Pro Val Ile Glu Ser Gly Val
 65                  70                  75                  80

Lys Arg Ala Ile Asn Glu Pro Ala Lys Met Ile Asp Glu Ala Ile Ala
                 85                  90                  95

Ala Ser Lys Asn Pro Asn Ala Arg Lys Val Ser Gly Ser Gly Val Ala
            100                 105                 110

Ala Ser Ala Glu Thr Thr Gly Glu Lys Leu Gly Trp Gly Lys Arg Ile
        115                 120                 125

Gln Gln Ala Val Met Thr Gly Val Ser Tyr Met Val Pro Phe Val Ala
    130                 135                 140

Ala Gly Gly Leu Leu Leu Ala Leu Gly Phe Ala Phe Gly Gly Tyr Asp
145                 150                 155                 160

Met Ala Asn Gly Trp Gln Ala Ile Ala Thr Gln Phe Ser Leu Thr Asn
                165                 170                 175

Leu Pro Gly Asn Thr Val Asp Val Asp
            180                 185
```

```
<210> SEQ ID NO 15
<211> LENGTH: 416
<212> TYPE: DNA
<213> ORGANISM: Corynebacterium glutamicum
<220> FEATURE:
<221> NAME/KEY: CDS
<222> LOCATION: (1)..(393)
<223> OTHER INFORMATION: RXA00951

<400> SEQUENCE: 15 atc caa gca atc tta gag aag gca gca gcg ccg gcg aag cag aag gct        48
Ile Gln Ala Ile Leu Glu Lys Ala Ala Ala Pro Ala Lys Gln Lys Ala
  1               5                  10                  15 cct gct gtg gct cct gct gta aca ccc act gac gct cct gca gcc tca        96
Pro Ala Val Ala Pro Ala Val Thr Pro Thr Asp Ala Pro Ala Ala Ser
             20                  25                  30 gtc caa tcc aaa acc cac gac aag atc ctc acc gtc tgt ggc aac ggc       144
Val Gln Ser Lys Thr His Asp Lys Ile Leu Thr Val Cys Gly Asn Gly
         35                  40                  45 ttg ggt acc tcc ctc ttc ctc aaa aac acc ctt gag caa gtt ttc gac       192
Leu Gly Thr Ser Leu Phe Leu Lys Asn Thr Leu Glu Gln Val Phe Asp
     50                  55                  60 acc tgg ggt tgg ggt cca tac atg acg gtg gag gca acc gac act atc       240
Thr Trp Gly Trp Gly Pro Tyr Met Thr Val Glu Ala Thr Asp Thr Ile
 65                  70                  75                  80 tcc gcc aag ggc aaa gcc aag gaa gct gat ctc atc atg acc tct ggt       288
Ser Ala Lys Gly Lys Ala Lys Glu Ala Asp Leu Ile Met Thr Ser Gly
                 85                  90                  95 gaa atc gcc cgc acg ttg ggt gat gtt gga atc ccg gtt cac gtg atc       336
Glu Ile Ala Arg Thr Leu Gly Asp Val Gly Ile Pro Val His Val Ile
            100                 105                 110 aat gac ttc acg agc acc gat gaa atc gat gct gcg ctt cgt gaa cgc       384
Asn Asp Phe Thr Ser Thr Asp Glu Ile Asp Ala Ala Leu Arg Glu Arg
        115                 120                 125 tac gac atc taactacttt aaaaggacga aaa                                 416
Tyr Asp Ile
    130

<210> SEQ ID NO 16
<211> LENGTH: 131
<212> TYPE: PRT
<213> ORGANISM: Corynebacterium glutamicum

<400> SEQUENCE: 16

Ile Gln Ala Ile Leu Glu Lys Ala Ala Ala Pro Ala Lys Gln Lys Ala
  1               5                  10                  15

Pro Ala Val Ala Pro Ala Val Thr Pro Thr Asp Ala Pro Ala Ala Ser
             20                  25                  30

Val Gln Ser Lys Thr His Asp Lys Ile Leu Thr Val Cys Gly Asn Gly
         35                  40                  45

Leu Gly Thr Ser Leu Phe Leu Lys Asn Thr Leu Glu Gln Val Phe Asp
     50                  55                  60

Thr Trp Gly Trp Gly Pro Tyr Met Thr Val Glu Ala Thr Asp Thr Ile
 65                  70                  75                  80

Ser Ala Lys Gly Lys Ala Lys Glu Ala Asp Leu Ile Met Thr Ser Gly
                 85                  90                  95

Glu Ile Ala Arg Thr Leu Gly Asp Val Gly Ile Pro Val His Val Ile
            100                 105                 110

Asn Asp Phe Thr Ser Thr Asp Glu Ile Asp Ala Ala Leu Arg Glu Arg
        115                 120                 125
```

Tyr Asp Ile
    130

<210> SEQ ID NO 17
<211> LENGTH: 1827
<212> TYPE: DNA
<213> ORGANISM: Corynebacterium glutamicum
<220> FEATURE:
<221> NAME/KEY: CDS
<222> LOCATION: (101)..(1804)
<223> OTHER INFORMATION: RXN01244

<400> SEQUENCE: 17

```
gatatgtgtt tgtttgtcaa tatccaaatg tttgaatagt tgcacaactg ttggttttgt      60
ggtgatcttg aggaaattaa ctcaatgatt gtgaggatgg gtg gct act gtg gct     115
                                             Val Ala Thr Val Ala
                                               1               5 gat gtg aat caa gac act gta ctg aag ggc acc ggc gtt gtc ggt gga     163
Asp Val Asn Gln Asp Thr Val Leu Lys Gly Thr Gly Val Val Gly Gly
             10                  15                  20 gtc cgt tat gca agc gcg gtg tgg att acc cca cgc ccc gaa cta ccc     211
Val Arg Tyr Ala Ser Ala Val Trp Ile Thr Pro Arg Pro Glu Leu Pro
         25                  30                  35 caa gca ggc gaa gtc gtc gcc gaa gaa aac cgt gaa gca gag cag gag     259
Gln Ala Gly Glu Val Val Ala Glu Glu Asn Arg Glu Ala Glu Gln Glu
     40                  45                  50 cgt ttc gac gcc gct gca gcc aca gtc tct tct cgt ttg ctt gag cgc     307
Arg Phe Asp Ala Ala Ala Ala Thr Val Ser Ser Arg Leu Leu Glu Arg
 55                  60                  65 tcc gaa gct gct gaa gga cca gca gct gag gtg ctt aaa gct act gct     355
Ser Glu Ala Ala Glu Gly Pro Ala Ala Glu Val Leu Lys Ala Thr Ala
 70                  75                  80                  85 ggc atg gtc aat gac cgt ggc tgg cgt aag gct gtc atc aag ggt gtc     403
Gly Met Val Asn Asp Arg Gly Trp Arg Lys Ala Val Ile Lys Gly Val
                 90                  95                 100 aag ggt ggt cac cct gcg gaa tac gcc gtg gtt gca gca aca acc aag     451
Lys Gly Gly His Pro Ala Glu Tyr Ala Val Val Ala Ala Thr Thr Lys
             105                 110                 115 ttc atc tcc atg ttc gaa gcc gca ggc ggc ctg atc gcg gag cgc acc     499
Phe Ile Ser Met Phe Glu Ala Ala Gly Gly Leu Ile Ala Glu Arg Thr
         120                 125                 130 aca gac ttg cgc gac atc cgc gac cgc gtc atc gca gaa ctt cgt ggc     547
Thr Asp Leu Arg Asp Ile Arg Asp Arg Val Ile Ala Glu Leu Arg Gly
     135                 140                 145 gat gaa gag cca ggt ctg cca gct gtt tcc gga cag gtc att ctc ttt     595
Asp Glu Glu Pro Gly Leu Pro Ala Val Ser Gly Gln Val Ile Leu Phe
150                 155                 160                 165 gca gat gac ctc tcc cca gca gac acc gcg gca cta gac aca gat ctc     643
Ala Asp Asp Leu Ser Pro Ala Asp Thr Ala Ala Leu Asp Thr Asp Leu
                 170                 175                 180 ttt gtg gga ctt gtc act gag ctg ggt ggc cca acg agc cac acc gcg     691
Phe Val Gly Leu Val Thr Glu Leu Gly Gly Pro Thr Ser His Thr Ala
             185                 190                 195 atc atc gca cgc cag ctc aac gtg cct tgc atc gtc gca tcc ggc gcc     739
Ile Ile Ala Arg Gln Leu Asn Val Pro Cys Ile Val Ala Ser Gly Ala
         200                 205                 210 ggc atc aag gac atc aag tcc ggc gaa aag gtg ctt atc gac ggc agc     787
Gly Ile Lys Asp Ile Lys Ser Gly Glu Lys Val Leu Ile Asp Gly Ser
     215                 220                 225 ctc ggc acc att gac cgc aac gcg gac gaa gct gaa gca acc aag ctc     835
```

```
Leu Gly Thr Ile Asp Arg Asn Ala Asp Glu Ala Glu Ala Thr Lys Leu
230                 235                 240                 245 gtc tcc gag tcc ctc gag cgc gct gct cgc atc gcc gag tgg aag ggt      883
Val Ser Glu Ser Leu Glu Arg Ala Ala Arg Ile Ala Glu Trp Lys Gly
                250                 255                 260 cct gca caa acc aag gac ggc tac cgc gtt cag ctg ttg gcc aac gtc      931
Pro Ala Gln Thr Lys Asp Gly Tyr Arg Val Gln Leu Leu Ala Asn Val
            265                 270                 275 caa gac ggc aac tct gca cag cag gct gca cag acc gaa gca gaa ggc      979
Gln Asp Gly Asn Ser Ala Gln Gln Ala Ala Gln Thr Glu Ala Glu Gly
        280                 285                 290 atc ggc ctg ttc cgc acc gaa ctg tgc ttc ctt tcc gcc acc gaa gag     1027
Ile Gly Leu Phe Arg Thr Glu Leu Cys Phe Leu Ser Ala Thr Glu Glu
    295                 300                 305 cca agc gtt gat gag cag gct gcg gtc tac tca aag gtg ctt gaa gca     1075
Pro Ser Val Asp Glu Gln Ala Ala Val Tyr Ser Lys Val Leu Glu Ala
310                 315                 320                 325 ttc cca gag tcc aag gtc gtt gtc cgc tcc ctc gac gca ggt tct gac     1123
Phe Pro Glu Ser Lys Val Val Val Arg Ser Leu Asp Ala Gly Ser Asp
                330                 335                 340 aag cca gtt cca ttc gca tcg atg gct gat gag atg aac cca gca ctg     1171
Lys Pro Val Pro Phe Ala Ser Met Ala Asp Glu Met Asn Pro Ala Leu
            345                 350                 355 ggt gtt cgt ggc ctg cgt atc gca cgt gga cag gtt gat ctg ctg act     1219
Gly Val Arg Gly Leu Arg Ile Ala Arg Gly Gln Val Asp Leu Leu Thr
        360                 365                 370 cgc cag ctc gac gca att gcg aag gcc agc gaa gaa ctc ggc cgt ggc     1267
Arg Gln Leu Asp Ala Ile Ala Lys Ala Ser Glu Glu Leu Gly Arg Gly
    375                 380                 385 gac gac gcc cca acc tgg gtt atg gct cca atg gtg gct acc gct tat     1315
Asp Asp Ala Pro Thr Trp Val Met Ala Pro Met Val Ala Thr Ala Tyr
390                 395                 400                 405 gaa gca aag tgg ttt gct gac atg tgc cgt gag cgt ggc cta atc gcc     1363
Glu Ala Lys Trp Phe Ala Asp Met Cys Arg Glu Arg Gly Leu Ile Ala
                410                 415                 420 ggc gcc atg atc gaa gtt cca gca gca tcc ctg atg gca gac aag atc     1411
Gly Ala Met Ile Glu Val Pro Ala Ala Ser Leu Met Ala Asp Lys Ile
            425                 430                 435 atg cct cac ctg gac ttt gtt tcc atc ggt acc aac gac ctg acc cag     1459
Met Pro His Leu Asp Phe Val Ser Ile Gly Thr Asn Asp Leu Thr Gln
        440                 445                 450 tac acc atg gca gcg gac cgc atg tct cct gag ctt gcc tac ctg acc     1507
Tyr Thr Met Ala Ala Asp Arg Met Ser Pro Glu Leu Ala Tyr Leu Thr
    455                 460                 465 gat cct tgg cag cca gca gtc ctg cgc ctg atc aag cac acc tgt gac     1555
Asp Pro Trp Gln Pro Ala Val Leu Arg Leu Ile Lys His Thr Cys Asp
470                 475                 480                 485 gaa ggt gct cgc ttt aac acc ccg gtc ggt gtt tgt ggt gaa gca gca     1603
Glu Gly Ala Arg Phe Asn Thr Pro Val Gly Val Cys Gly Glu Ala Ala
                490                 495                 500 gca gac cca ctg ttg gca act gtc ctc acc ggt ctt ggc gtg aac tcc     1651
Ala Asp Pro Leu Leu Ala Thr Val Leu Thr Gly Leu Gly Val Asn Ser
            505                 510                 515 ctg tcc gca gca tcc act gct ctc gca gca gtc ggt gca aag ctg tca     1699
Leu Ser Ala Ala Ser Thr Ala Leu Ala Ala Val Gly Ala Lys Leu Ser
        520                 525                 530 gag gtc acc ctg gaa acc tgt aag aag gca gca gaa gca gca ctt gac     1747
Glu Val Thr Leu Glu Thr Cys Lys Lys Ala Ala Glu Ala Ala Leu Asp
    535                 540                 545
```

```
gct gaa ggt gca act gaa gca cgc gat gct gta cgc gca gtg atc gac    1795
Ala Glu Gly Ala Thr Glu Ala Arg Asp Ala Val Arg Ala Val Ile Asp
550             555                 560                 565 gca gca gtc taaaccactg ttgagctaaa aag                              1827
Ala Ala Val
```

<210> SEQ ID NO 18
<211> LENGTH: 568
<212> TYPE: PRT
<213> ORGANISM: Corynebacterium glutamicum

<400> SEQUENCE: 18

```
Val Ala Thr Val Ala Asp Val Asn Gln Asp Thr Val Leu Lys Gly Thr
 1               5                  10                  15

Gly Val Val Gly Gly Val Arg Tyr Ala Ser Ala Val Trp Ile Thr Pro
            20                  25                  30

Arg Pro Glu Leu Pro Gln Ala Gly Val Val Ala Glu Glu Asn Arg
         35                  40                  45

Glu Ala Glu Gln Glu Arg Phe Asp Ala Ala Ala Thr Val Ser Ser
     50                  55                  60

Arg Leu Leu Glu Arg Ser Glu Ala Ala Glu Gly Pro Ala Ala Glu Val
 65                  70                  75                  80

Leu Lys Ala Thr Ala Gly Met Val Asn Asp Arg Gly Trp Arg Lys Ala
                 85                  90                  95

Val Ile Lys Gly Val Lys Gly Gly His Pro Ala Glu Tyr Ala Val Val
            100                 105                 110

Ala Ala Thr Thr Lys Phe Ile Ser Met Phe Glu Ala Ala Gly Gly Leu
        115                 120                 125

Ile Ala Glu Arg Thr Thr Asp Leu Arg Asp Ile Arg Asp Arg Val Ile
    130                 135                 140

Ala Glu Leu Arg Gly Asp Glu Glu Pro Gly Leu Pro Ala Val Ser Gly
145                 150                 155                 160

Gln Val Ile Leu Phe Ala Asp Asp Leu Ser Pro Ala Asp Thr Ala Ala
                165                 170                 175

Leu Asp Thr Asp Leu Phe Val Gly Leu Val Thr Glu Leu Gly Gly Pro
            180                 185                 190

Thr Ser His Thr Ala Ile Ile Ala Arg Gln Leu Asn Val Pro Cys Ile
        195                 200                 205

Val Ala Ser Gly Ala Gly Ile Lys Asp Ile Lys Ser Gly Glu Lys Val
    210                 215                 220

Leu Ile Asp Gly Ser Leu Gly Thr Ile Asp Arg Asn Ala Asp Glu Ala
225                 230                 235                 240

Glu Ala Thr Lys Leu Val Ser Glu Ser Leu Glu Arg Ala Ala Arg Ile
                245                 250                 255

Ala Glu Trp Lys Gly Pro Ala Gln Thr Lys Asp Gly Tyr Arg Val Gln
            260                 265                 270

Leu Leu Ala Asn Val Gln Asp Gly Asn Ser Ala Gln Gln Ala Ala Gln
        275                 280                 285

Thr Glu Ala Glu Gly Ile Gly Leu Phe Arg Thr Glu Leu Cys Phe Leu
    290                 295                 300

Ser Ala Thr Glu Glu Pro Ser Val Asp Glu Gln Ala Ala Val Tyr Ser
305                 310                 315                 320

Lys Val Leu Glu Ala Phe Pro Glu Ser Lys Val Val Arg Ser Leu
                325                 330                 335

Asp Ala Gly Ser Asp Lys Pro Val Pro Phe Ala Ser Met Ala Asp Glu
```

```
                     340                 345                 350
Met Asn Pro Ala Leu Gly Val Arg Gly Leu Arg Ile Ala Arg Gly Gln
                355                 360                 365

Val Asp Leu Leu Thr Arg Gln Leu Asp Ala Ile Ala Lys Ala Ser Glu
        370                 375                 380

Glu Leu Gly Arg Gly Asp Asp Ala Pro Thr Trp Val Met Ala Pro Met
385                 390                 395                 400

Val Ala Thr Ala Tyr Glu Ala Lys Trp Phe Ala Asp Met Cys Arg Glu
                405                 410                 415

Arg Gly Leu Ile Ala Gly Ala Met Ile Glu Val Pro Ala Ala Ser Leu
            420                 425                 430

Met Ala Asp Lys Ile Met Pro His Leu Asp Phe Val Ser Ile Gly Thr
        435                 440                 445

Asn Asp Leu Thr Gln Tyr Thr Met Ala Ala Asp Arg Met Ser Pro Glu
    450                 455                 460

Leu Ala Tyr Leu Thr Asp Pro Trp Gln Pro Ala Val Leu Arg Leu Ile
465                 470                 475                 480

Lys His Thr Cys Asp Glu Gly Ala Arg Phe Asn Thr Pro Val Gly Val
                485                 490                 495

Cys Gly Glu Ala Ala Ala Asp Pro Leu Leu Ala Thr Val Leu Thr Gly
            500                 505                 510

Leu Gly Val Asn Ser Leu Ser Ala Ala Ser Thr Ala Leu Ala Ala Val
        515                 520                 525

Gly Ala Lys Leu Ser Glu Val Thr Leu Glu Thr Cys Lys Lys Ala Ala
    530                 535                 540

Glu Ala Ala Leu Asp Ala Glu Gly Ala Thr Glu Ala Arg Asp Ala Val
545                 550                 555                 560

Arg Ala Val Ile Asp Ala Ala Val
                565

<210> SEQ ID NO 19
<211> LENGTH: 1629
<212> TYPE: DNA
<213> ORGANISM: Corynebacterium glutamicum
<220> FEATURE:
<221> NAME/KEY: CDS
<222> LOCATION: (98)..(1606)
<223> OTHER INFORMATION: FRXA01244

<400> SEQUENCE: 19
agatgtcgat ttctcgagga agaagttaac gccgaagaaa accgtgaatc agagcaggag      60
cgcttcgacg ccgctgcagc cacagtctct tcttcgt ttg ctt gag cgc tcc gaa     115
                                         Leu Leu Glu Arg Ser Glu
                                           1               5 gct gct gaa gga cca gca gct gag gtg ctt aaa gct act gct ggc atg     163
Ala Ala Glu Gly Pro Ala Ala Glu Val Leu Lys Ala Thr Ala Gly Met
         10                  15                  20 gtc aat gac cgt ggc tgg cgt aag gct gtc atc aag ggt gtc aag ggt     211
Val Asn Asp Arg Gly Trp Arg Lys Ala Val Ile Lys Gly Val Lys Gly
     25                  30                  35 ggt cac cct gcg gaa tac gcc gtg gtt gca gca aca acc aag ttc atc     259
Gly His Pro Ala Glu Tyr Ala Val Val Ala Ala Thr Thr Lys Phe Ile
 40                  45                  50 tcc atg ttc gaa gcc gca ggc ggc ctg atc gcg gag cgc acc aca gac     307
Ser Met Phe Glu Ala Ala Gly Gly Leu Ile Ala Glu Arg Thr Thr Asp
 55                  60                  65                  70 ttg cgc gac atc cgc gac cgc gtc atc gca gaa ctt cgt ggc gat gaa     355
Leu Arg Asp Ile Arg Asp Arg Val Ile Ala Glu Leu Arg Gly Asp Glu
```

```
Leu Arg Asp Ile Arg Asp Arg Val Ile Ala Glu Leu Arg Gly Asp Glu
                 75                  80                  85 gag cca ggt ctg cca gct gtt tcc gga cag gtc att ctc ttt gca gat       403
Glu Pro Gly Leu Pro Ala Val Ser Gly Gln Val Ile Leu Phe Ala Asp
             90                  95                 100 gac ctc tcc cca gca gac acc gcg gca cta gac aca gat ctc ttt gtg       451
Asp Leu Ser Pro Ala Asp Thr Ala Ala Leu Asp Thr Asp Leu Phe Val
            105                 110                 115 gga ctt gtc act gag ctg ggt ggc cca acg agc cac acc gcg atc atc       499
Gly Leu Val Thr Glu Leu Gly Gly Pro Thr Ser His Thr Ala Ile Ile
        120                 125                 130 gca cgc cag ctc aac gtg cct tgc atc gtc gca tcc ggc gcc ggc atc       547
Ala Arg Gln Leu Asn Val Pro Cys Ile Val Ala Ser Gly Ala Gly Ile
135                 140                 145                 150 aag gac atc aag tcc ggc gaa aag gtg ctt atc gac ggc agc ctc ggc       595
Lys Asp Ile Lys Ser Gly Glu Lys Val Leu Ile Asp Gly Ser Leu Gly
                155                 160                 165 acc att gac cgc aac gcg gac gaa gct gaa gca acc aag ctc gtc tcc       643
Thr Ile Asp Arg Asn Ala Asp Glu Ala Glu Ala Thr Lys Leu Val Ser
            170                 175                 180 gag tcc ctc gag cgc gct gct cgc atc gcc gag tgg aag ggt cct gca       691
Glu Ser Leu Glu Arg Ala Ala Arg Ile Ala Glu Trp Lys Gly Pro Ala
        185                 190                 195 caa acc aag gac ggc tac cgc gtt cag ctg ttg gcc aac gtc caa gac       739
Gln Thr Lys Asp Gly Tyr Arg Val Gln Leu Leu Ala Asn Val Gln Asp
        200                 205                 210 ggc aac tct gca cag cag gct gca cag acc gaa gca gaa ggc atc ggc       787
Gly Asn Ser Ala Gln Gln Ala Ala Gln Thr Glu Ala Glu Gly Ile Gly
215                 220                 225                 230 ctg ttc cgc acc gaa ctg tgc ttc ctt tcc gcc acc gaa gag cca agc       835
Leu Phe Arg Thr Glu Leu Cys Phe Leu Ser Ala Thr Glu Glu Pro Ser
                235                 240                 245 gtt gat gag cag gct gcg gtc tac tca aag gtg ctt gaa gca ttc cca       883
Val Asp Glu Gln Ala Ala Val Tyr Ser Lys Val Leu Glu Ala Phe Pro
            250                 255                 260 gag tcc aag gtc gtt gtc cgc tcc ctc gac gca ggt tct gac aag cca       931
Glu Ser Lys Val Val Val Arg Ser Leu Asp Ala Gly Ser Asp Lys Pro
        265                 270                 275 gtt cca ttc gca tcg atg gct gat gag atg aac cca gca ctg ggt gtt       979
Val Pro Phe Ala Ser Met Ala Asp Glu Met Asn Pro Ala Leu Gly Val
        280                 285                 290 cgt ggc ctg cgt atc gca cgt gga cag gtt gat ctg ctg act cgc cag       1027
Arg Gly Leu Arg Ile Ala Arg Gly Gln Val Asp Leu Leu Thr Arg Gln
295                 300                 305                 310 ctc gac gca att gcg aag gcc agc gaa gaa ctc ggc cgt ggc gac gac       1075
Leu Asp Ala Ile Ala Lys Ala Ser Glu Glu Leu Gly Arg Gly Asp Asp
                315                 320                 325 gcc cca acc tgg gtt atg gct cca atg gtg gct acc gct tat gaa gca       1123
Ala Pro Thr Trp Val Met Ala Pro Met Val Ala Thr Ala Tyr Glu Ala
            330                 335                 340 aag tgg ttt gct gac atg tgc cgt gag cgt ggc cta atc gcc ggc gcc       1171
Lys Trp Phe Ala Asp Met Cys Arg Glu Arg Gly Leu Ile Ala Gly Ala
        345                 350                 355 atg atc gaa gtt cca gca gca tcc ctg atg gca gac aag atc atg cct       1219
Met Ile Glu Val Pro Ala Ala Ser Leu Met Ala Asp Lys Ile Met Pro
360                 365                 370 cac ctg gac ttt gtt tcc atc ggt acc aac gac ctg acc cag tac acc       1267
His Leu Asp Phe Val Ser Ile Gly Thr Asn Asp Leu Thr Gln Tyr Thr
                375                 380                 385                 390
```

```
atg gca gcg gac cgc atg tct cct gag ctt gcc tac ctg acc gat cct      1315
Met Ala Ala Asp Arg Met Ser Pro Glu Leu Ala Tyr Leu Thr Asp Pro
            395                 400                 405 tgg cag cca gca gtc ctg cgc ctg atc aag cac acc tgt gac gaa ggt      1363
Trp Gln Pro Ala Val Leu Arg Leu Ile Lys His Thr Cys Asp Glu Gly
        410                 415                 420 gct cgc ttt aac acc ccg gtc ggt gtt tgt ggt gaa gca gca gca gac      1411
Ala Arg Phe Asn Thr Pro Val Gly Val Cys Gly Glu Ala Ala Ala Asp
    425                 430                 435 cca ctg ttg gca act gtc ctc acc ggt ctt ggc gtg aac tcc ctg tcc      1459
Pro Leu Leu Ala Thr Val Leu Thr Gly Leu Gly Val Asn Ser Leu Ser
440                 445                 450 gca gca tcc act gct ctc gca gca gtc ggt gca aag ctg tca gag gtc      1507
Ala Ala Ser Thr Ala Leu Ala Ala Val Gly Ala Lys Leu Ser Glu Val
    455                 460                 465                 470 acc ctg gaa acc tgt aag aag gca gca gaa gca gca ctt gac gct gaa      1555
Thr Leu Glu Thr Cys Lys Lys Ala Ala Glu Ala Ala Leu Asp Ala Glu
                475                 480                 485 ggt gca act gaa gca cgc gat gct gta cgc gca gtg atc gac gca gca      1603
Gly Ala Thr Glu Ala Arg Asp Ala Val Arg Ala Val Ile Asp Ala Ala
            490                 495                 500 gtc taaaccactg ttgagctaaa aag                                         1629
Val

<210> SEQ ID NO 20
<211> LENGTH: 503
<212> TYPE: PRT
<213> ORGANISM: Corynebacterium glutamicum

<400> SEQUENCE: 20

Leu Leu Glu Arg Ser Glu Ala Ala Glu Gly Pro Ala Ala Glu Val Leu
 1               5                  10                  15

Lys Ala Thr Ala Gly Met Val Asn Asp Arg Gly Trp Arg Lys Ala Val
            20                  25                  30

Ile Lys Gly Val Lys Gly Gly His Pro Ala Glu Tyr Ala Val Val Ala
        35                  40                  45

Ala Thr Thr Lys Phe Ile Ser Met Phe Glu Ala Ala Gly Gly Leu Ile
    50                  55                  60

Ala Glu Arg Thr Thr Asp Leu Arg Asp Ile Arg Asp Arg Val Ile Ala
65                  70                  75                  80

Glu Leu Arg Gly Asp Glu Glu Pro Gly Leu Pro Ala Val Ser Gly Gln
                85                  90                  95

Val Ile Leu Phe Ala Asp Asp Leu Ser Pro Ala Asp Thr Ala Ala Leu
            100                 105                 110

Asp Thr Asp Leu Phe Val Gly Leu Val Thr Glu Leu Gly Gly Pro Thr
        115                 120                 125

Ser His Thr Ala Ile Ile Ala Arg Gln Leu Asn Val Pro Cys Ile Val
    130                 135                 140

Ala Ser Gly Ala Gly Ile Lys Asp Ile Lys Ser Gly Glu Lys Val Leu
145                 150                 155                 160

Ile Asp Gly Ser Leu Gly Thr Ile Asp Arg Asn Ala Asp Glu Ala Glu
                165                 170                 175

Ala Thr Lys Leu Val Ser Glu Ser Leu Glu Arg Ala Ala Arg Ile Ala
            180                 185                 190

Glu Trp Lys Gly Pro Ala Gln Thr Lys Asp Gly Tyr Arg Val Gln Leu
        195                 200                 205

Leu Ala Asn Val Gln Asp Gly Asn Ser Ala Gln Gln Ala Ala Gln Thr
```

-continued

```
                    210                 215                 220
Glu Ala Glu Gly Ile Gly Leu Phe Arg Thr Glu Leu Cys Phe Leu Ser
225                 230                 235                 240

Ala Thr Glu Glu Pro Ser Val Asp Gln Ala Ala Val Tyr Ser Lys
                245                 250                 255

Val Leu Glu Ala Phe Pro Glu Ser Lys Val Val Arg Ser Leu Asp
                260                 265                 270

Ala Gly Ser Asp Lys Pro Val Pro Phe Ala Ser Met Ala Asp Glu Met
                275                 280                 285

Asn Pro Ala Leu Gly Val Arg Gly Leu Arg Ile Ala Arg Gly Gln Val
290                 295                 300

Asp Leu Leu Thr Arg Gln Leu Asp Ala Ile Ala Lys Ala Ser Glu Glu
305                 310                 315                 320

Leu Gly Arg Gly Asp Asp Ala Pro Thr Trp Val Met Ala Pro Met Val
                325                 330                 335

Ala Thr Ala Tyr Glu Ala Lys Trp Phe Ala Asp Met Cys Arg Glu Arg
                340                 345                 350

Gly Leu Ile Ala Gly Ala Met Ile Glu Val Pro Ala Ala Ser Leu Met
                355                 360                 365

Ala Asp Lys Ile Met Pro His Leu Asp Phe Val Ser Ile Gly Thr Asn
370                 375                 380

Asp Leu Thr Gln Tyr Thr Met Ala Ala Asp Arg Met Ser Pro Glu Leu
385                 390                 395                 400

Ala Tyr Leu Thr Asp Pro Trp Gln Pro Ala Val Leu Arg Leu Ile Lys
                405                 410                 415

His Thr Cys Asp Glu Gly Ala Arg Phe Asn Thr Pro Val Gly Val Cys
                420                 425                 430

Gly Glu Ala Ala Ala Asp Pro Leu Leu Ala Thr Val Leu Thr Gly Leu
                435                 440                 445

Gly Val Asn Ser Leu Ser Ala Ala Ser Thr Ala Leu Ala Ala Val Gly
                450                 455                 460

Ala Lys Leu Ser Glu Val Thr Leu Glu Thr Cys Lys Lys Ala Ala Glu
465                 470                 475                 480

Ala Ala Leu Asp Ala Glu Gly Ala Thr Glu Ala Arg Asp Ala Val Arg
                485                 490                 495

Ala Val Ile Asp Ala Ala Val
                500

<210> SEQ ID NO 21
<211> LENGTH: 390
<212> TYPE: DNA
<213> ORGANISM: Corynebacterium glutamicum
<220> FEATURE:
<221> NAME/KEY: CDS
<222> LOCATION: (101)..(367)
<223> OTHER INFORMATION: RXA01300

<400> SEQUENCE: 21
gatcgacatt aaatcccctc ccttgggggg tttaactaac aaatcgctgc gccctaatcc      60
gttcggatta acgcgtagc aacacgaaag gacactttcc atg gct tcc aag act       115
                                            Met Ala Ser Lys Thr
                                              1               5 gta acc gtc ggt tcc tcc gtt ggc ctg cac gca cgt cca gca tcc atc      163
Val Thr Val Gly Ser Ser Val Gly Leu His Ala Arg Pro Ala Ser Ile
         10                  15                  20 atc gct gaa gcg gct gct gag tac gac gac gaa atc ttg ctg acc ctg      211
```

```
                Ile Ala Glu Ala Ala Glu Tyr Asp Asp Glu Ile Leu Leu Thr Leu
                             25                   30                  35 gtt ggc tcc gat gat gac gaa gag acc gac gcg tcc tct tcc ctc atg          259
Val Gly Ser Asp Asp Asp Glu Glu Thr Asp Ala Ser Ser Ser Leu Met
 40                  45                  50 atc atg gcg ctg ggc gca gag cac ggc aac gaa gtt acc gtc acc tcc          307
Ile Met Ala Leu Gly Ala Glu His Gly Asn Glu Val Thr Val Thr Ser
 55                  60                  65 gac aac gct gaa gct gtt gag aag atc gct gcg ctt atc gca cag gac          355
Asp Asn Ala Glu Ala Val Glu Lys Ile Ala Ala Leu Ile Ala Gln Asp
 70                  75                  80                  85 ctt gac gct gag taaacaacgc tctgcttgtt aaa                                390
Leu Asp Ala Glu <210> SEQ ID NO 22
<211> LENGTH: 89
<212> TYPE: PRT
<213> ORGANISM: Corynebacterium glutamicum

<400> SEQUENCE: 22

Met Ala Ser Lys Thr Val Thr Val Gly Ser Ser Val Gly Leu His Ala
 1               5                  10                  15

Arg Pro Ala Ser Ile Ile Ala Glu Ala Ala Glu Tyr Asp Asp Glu
             20                  25                  30

Ile Leu Leu Thr Leu Val Gly Ser Asp Asp Asp Glu Glu Thr Asp Ala
         35                  40                  45

Ser Ser Ser Leu Met Ile Met Ala Leu Gly Ala Glu His Gly Asn Glu
     50                  55                  60

Val Thr Val Thr Ser Asp Asn Ala Glu Ala Val Glu Lys Ile Ala Ala
 65                  70                  75                  80

Leu Ile Ala Gln Asp Leu Asp Ala Glu
                 85

<210> SEQ ID NO 23
<211> LENGTH: 508
<212> TYPE: DNA
<213> ORGANISM: Corynebacterium glutamicum
<220> FEATURE:
<221> NAME/KEY: CDS
<222> LOCATION: (101)..(508)
<223> OTHER INFORMATION: RXN03002

<400> SEQUENCE: 23
ggaacttcga ggtgtcttcg tgggcgtac ggagatctag caagtgtggc tttatgtttg           60
accctatccg aatcaacatg cagtgaatta acatctactt atg ttt gta ctc aaa          115
                                            Met Phe Val Leu Lys
                                             1               5 gat ctg cta aag gca gaa cgc ata gaa ctc gac cgc acg gtc acc gat          163
Asp Leu Leu Lys Ala Glu Arg Ile Glu Leu Asp Arg Thr Val Thr Asp
             10                  15                  20 tgg cgt gaa ggc atc cgc gcc gca ggt gta ctc cta gaa aag aca aac          211
Trp Arg Glu Gly Ile Arg Ala Ala Gly Val Leu Leu Glu Lys Thr Asn
         25                  30                  35 agc att gat tcc gcc tac acc gat gcc atg atc gcc agc gtg gaa gaa          259
Ser Ile Asp Ser Ala Tyr Thr Asp Ala Met Ile Ala Ser Val Glu Glu
     40                  45                  50 aaa ggc ccc tac att gtg gtc gct cca ggt ttc gct ttc gcg cac gcc          307
Lys Gly Pro Tyr Ile Val Val Ala Pro Gly Phe Ala Phe Ala His Ala
 55                  60                  65 cgc ccc agc aga gca gtc cgc gag acc gct atg tcg tgg gtg cgc ctg          355
```

```
Arg Pro Ser Arg Ala Val Arg Glu Thr Ala Met Ser Trp Val Arg Leu
 70                  75                  80                  85 gcc tcc cct gtt tcc ttc ggt cac agt aag aat gat ccc ctc aat ctc      403
Ala Ser Pro Val Ser Phe Gly His Ser Lys Asn Asp Pro Leu Asn Leu
                 90                  95                 100 atc gtt gct ctc gct gcc aaa gat gcc acc gca cat acc caa gcg atg      451
Ile Val Ala Leu Ala Ala Lys Asp Ala Thr Ala His Thr Gln Ala Met
            105                 110                 115 gcg gca ttg gct aaa gct tta gga aaa tac cga aag gat ctc gac gag      499
Ala Ala Leu Ala Lys Ala Leu Gly Lys Tyr Arg Lys Asp Leu Asp Glu
        120                 125                 130 gca caa agt                                                          508
Ala Gln Ser
    135

<210> SEQ ID NO 24
<211> LENGTH: 136
<212> TYPE: PRT
<213> ORGANISM: Corynebacterium glutamicum

<400> SEQUENCE: 24

Met Phe Val Leu Lys Asp Leu Leu Lys Ala Glu Arg Ile Glu Leu Asp
  1               5                  10                  15

Arg Thr Val Thr Asp Trp Arg Glu Gly Ile Arg Ala Ala Gly Val Leu
             20                  25                  30

Leu Glu Lys Thr Asn Ser Ile Asp Ser Ala Tyr Thr Asp Ala Met Ile
         35                  40                  45

Ala Ser Val Glu Glu Lys Gly Pro Tyr Ile Val Val Ala Pro Gly Phe
     50                  55                  60

Ala Phe Ala His Ala Arg Pro Ser Arg Ala Val Arg Glu Thr Ala Met
 65                  70                  75                  80

Ser Trp Val Arg Leu Ala Ser Pro Val Ser Phe Gly His Ser Lys Asn
                 85                  90                  95

Asp Pro Leu Asn Leu Ile Val Ala Leu Ala Ala Lys Asp Ala Thr Ala
            100                 105                 110

His Thr Gln Ala Met Ala Ala Leu Ala Lys Ala Leu Gly Lys Tyr Arg
        115                 120                 125

Lys Asp Leu Asp Glu Ala Gln Ser
    130                 135

<210> SEQ ID NO 25
<211> LENGTH: 789
<212> TYPE: DNA
<213> ORGANISM: Corynebacterium glutamicum
<220> FEATURE:
<221> NAME/KEY: CDS
<222> LOCATION: (14)..(766)
<223> OTHER INFORMATION: RXC00953

<400> SEQUENCE: 25
cttgcattcc cca atg gcg cca cca acg gta ggc aac tac atc atg cag tcc    52
            Met Ala Pro Pro Thr Val Gly Asn Tyr Ile Met Gln Ser
              1               5                  10 ttc act caa ggt ctg cag ttc ggc gtt gca gtt gcc gtg att ctc ttt      100
Phe Thr Gln Gly Leu Gln Phe Gly Val Ala Val Ala Val Ile Leu Phe
         15                  20                  25 ggt gtc cgc acc att ctt ggt gaa ctg gtc ccc gca ttc caa ggt att      148
Gly Val Arg Thr Ile Leu Gly Glu Leu Val Pro Ala Phe Gln Gly Ile
     30                  35                  40                  45 gct gcg aag gtt gtt ccc gga gct atc ccc gca ttg gat gca ccg atc      196
```

```
                                                                         244
gtg ttc ccc tac gcg cag aac gcc gtt ctc att ggt ttc ttg tct tcc
Val Phe Pro Tyr Ala Gln Asn Ala Val Leu Ile Gly Phe Leu Ser Ser
             65                  70                  75

292
ttc gtc ggt ggc ttg gtt ggc ctg act gtt ctt gca tcg tgg ctg aac
Phe Val Gly Gly Leu Val Gly Leu Thr Val Leu Ala Ser Trp Leu Asn
         80                  85                  90

340
cca gct ttt ggt gtc gcg ttg att ctg cct ggt ttg gtc ccc cac ttc
Pro Ala Phe Gly Val Ala Leu Ile Leu Pro Gly Leu Val Pro His Phe
     95                 100                 105

388
ttc act ggt ggc gcg gcg ggc gtt tac ggt aat gcc acg ggt ggt cgt
Phe Thr Gly Gly Ala Ala Gly Val Tyr Gly Asn Ala Thr Gly Gly Arg
110                 115                 120                 125

436
cga gga gca gta ttt ggc gcc ttt gcc aac ggt ctt ctg att acc ttc
Arg Gly Ala Val Phe Gly Ala Phe Ala Asn Gly Leu Leu Ile Thr Phe
                130                 135                 140

484
ctc cct gct ttc ctg ctt ggt gtg ctt ggt tcc ttc ggg tca gag aac
Leu Pro Ala Phe Leu Leu Gly Val Leu Gly Ser Phe Gly Ser Glu Asn
            145                 150                 155

532
acc act ttc ggt gat gcg gac ttt ggt tgg ttc gga atc gtt gtt ggt
Thr Thr Phe Gly Asp Ala Asp Phe Gly Trp Phe Gly Ile Val Val Gly
        160                 165                 170

580
tct gca gcc aag gtg gaa ggt gct ggc ggg ctc atc ttg ttg ctc atc
Ser Ala Ala Lys Val Glu Gly Ala Gly Gly Leu Ile Leu Leu Leu Ile
    175                 180                 185

628
atc gca gcg gtt ctt ctg ggt ggc gcg atg gtc ttc cag aag cgc gtc
Ile Ala Ala Val Leu Leu Gly Gly Ala Met Val Phe Gln Lys Arg Val
190                 195                 200                 205

676
gtg aat ggg cac tgg gat cca gct ccc aac cgt gag cgc gtg gag aag
Val Asn Gly His Trp Asp Pro Ala Pro Asn Arg Glu Arg Val Glu Lys
                210                 215                 220

724
gcg gaa gct gat gcc act cca acg gct ggg gct cgg acc tac cct aag
Ala Glu Ala Asp Ala Thr Pro Thr Ala Gly Ala Arg Thr Tyr Pro Lys
            225                 230                 235

766
att gct cct ccg gcg ggc gct cct acc cca ccg gct cga agc
Ile Ala Pro Pro Ala Gly Ala Pro Thr Pro Pro Ala Arg Ser
        240                 245                 250 taagatctcc aaaaccctga gat                                                789

<210> SEQ ID NO 26
<211> LENGTH: 251
<212> TYPE: PRT
<213> ORGANISM: Corynebacterium glutamicum

<400> SEQUENCE: 26

Met Ala Pro Pro Thr Val Gly Asn Tyr Ile Met Gln Ser Phe Thr Gln
1               5                   10                  15

Gly Leu Gln Phe Gly Val Ala Val Ala Val Ile Leu Phe Gly Val Arg
            20                  25                  30

Thr Ile Leu Gly Glu Leu Val Pro Ala Phe Gln Gly Ile Ala Ala Lys
        35                  40                  45

Val Val Pro Gly Ala Ile Pro Ala Leu Asp Ala Pro Ile Val Phe Pro
    50                  55                  60

Tyr Ala Gln Asn Ala Val Leu Ile Gly Phe Leu Ser Ser Phe Val Gly
65                  70                  75                  80

Gly Leu Val Gly Leu Thr Val Leu Ala Ser Trp Leu Asn Pro Ala Phe
                85                  90                  95
```

-continued

```
Gly Val Ala Leu Ile Leu Pro Gly Leu Val Pro His Phe Phe Thr Gly
                100                 105                 110
Gly Ala Ala Gly Val Tyr Gly Asn Ala Thr Gly Gly Arg Arg Gly Ala
            115                 120                 125
Val Phe Gly Ala Phe Ala Asn Gly Leu Leu Ile Thr Phe Leu Pro Ala
        130                 135                 140
Phe Leu Leu Gly Val Leu Gly Ser Phe Gly Ser Glu Asn Thr Thr Phe
145                 150                 155                 160
Gly Asp Ala Asp Phe Gly Trp Phe Gly Ile Val Val Gly Ser Ala Ala
                165                 170                 175
Lys Val Glu Gly Ala Gly Gly Leu Ile Leu Leu Leu Ile Ile Ala Ala
            180                 185                 190
Val Leu Leu Gly Gly Ala Met Val Phe Gln Lys Arg Val Val Asn Gly
        195                 200                 205
His Trp Asp Pro Ala Pro Asn Arg Glu Arg Val Glu Lys Ala Glu Ala
210                 215                 220
Asp Ala Thr Pro Thr Ala Gly Ala Arg Thr Tyr Pro Lys Ile Ala Pro
225                 230                 235                 240
Pro Ala Gly Ala Pro Thr Pro Pro Ala Arg Ser
                245                 250
```

<210> SEQ ID NO 27
<211> LENGTH: 553
<212> TYPE: DNA
<213> ORGANISM: Corynebacterium glutamicum
<220> FEATURE:
<221> NAME/KEY: CDS
<222> LOCATION: (101)..(553)
<223> OTHER INFORMATION: RXC03001

<400> SEQUENCE: 27

```
cccggttcac gtgatcaatg acttcacgag caccgatgaa atcgatgctg cgcttcgtga        60
acgctacgac atctaactac tttaaaagga cgaaaatatt atg gac tgg tta acc       115
                                             Met Asp Trp Leu Thr
                                               1               5 att cct ctt ttc ctc gtt aat gaa atc ctt gcg gtt ccg gct ttc ctc       163
Ile Pro Leu Phe Leu Val Asn Glu Ile Leu Ala Val Pro Ala Phe Leu
             10                  15                  20 atc ggt atc atc acc gcc gtg gga ttg ggt gcc atg ggg cgt tcc gtc       211
Ile Gly Ile Ile Thr Ala Val Gly Leu Gly Ala Met Gly Arg Ser Val
         25                  30                  35 ggt cag gtt atc ggt gga gca atc aaa gca acg ttg ggc ttt ttg ctc       259
Gly Gln Val Ile Gly Gly Ala Ile Lys Ala Thr Leu Gly Phe Leu Leu
     40                  45                  50 att ggt gcg ggt gcc acg ttg gtc act gcc tcc ctg gag cca ctg ggt       307
Ile Gly Ala Gly Ala Thr Leu Val Thr Ala Ser Leu Glu Pro Leu Gly
 55                  60                  65 gcg atg atc atg ggt gcc aca ggc atg cgt ggt gtt gtc cca acg aat       355
Ala Met Ile Met Gly Ala Thr Gly Met Arg Gly Val Val Pro Thr Asn
                 70                  75                  80                  85 gaa gcc atc gcc gga atc gca cag gct gaa tac ggc gcg cag gtg gcg       403
Glu Ala Ile Ala Gly Ile Ala Gln Ala Glu Tyr Gly Ala Gln Val Ala
                 90                  95                 100 tgg ctg atg att ctg ggc ttc gcc atc tct ttg gtg ttg gct cgt ttc       451
Trp Leu Met Ile Leu Gly Phe Ala Ile Ser Leu Val Leu Ala Arg Phe
            105                 110                 115 acc aac ctg cgt tat gtc ttg ctc aac gga cac cac gtg ctg ttg atg       499
Thr Asn Leu Arg Tyr Val Leu Leu Asn Gly His His Val Leu Leu Met
        120                 125                 130
```

```
tgc acc atg ctc acc atg gtc ttg gcc acc gga aga gtt gat gcg tgg      547
Cys Thr Met Leu Thr Met Val Leu Ala Thr Gly Arg Val Asp Ala Trp
135                 140                 145 atc ttc                                                              553
Ile Phe
150

<210> SEQ ID NO 28
<211> LENGTH: 151
<212> TYPE: PRT
<213> ORGANISM: Corynebacterium glutamicum

<400> SEQUENCE: 28

Met Asp Trp Leu Thr Ile Pro Leu Phe Leu Val Asn Glu Ile Leu Ala
 1               5                  10                  15

Val Pro Ala Phe Leu Ile Gly Ile Ile Thr Ala Val Gly Leu Gly Ala
                20                  25                  30

Met Gly Arg Ser Val Gly Gln Val Ile Gly Gly Ala Ile Lys Ala Thr
            35                  40                  45

Leu Gly Phe Leu Leu Ile Gly Ala Gly Ala Thr Leu Val Thr Ala Ser
        50                  55                  60

Leu Glu Pro Leu Gly Ala Met Ile Met Gly Ala Thr Gly Met Arg Gly
 65                  70                  75                  80

Val Val Pro Thr Asn Glu Ala Ile Ala Gly Ile Ala Gln Ala Glu Tyr
                85                  90                  95

Gly Ala Gln Val Ala Trp Leu Met Ile Leu Gly Phe Ala Ile Ser Leu
            100                 105                 110

Val Leu Ala Arg Phe Thr Asn Leu Arg Tyr Val Leu Leu Asn Gly His
        115                 120                 125

His Val Leu Leu Met Cys Thr Met Leu Thr Met Val Leu Ala Thr Gly
130                 135                 140

Arg Val Asp Ala Trp Ile Phe
145                 150

<210> SEQ ID NO 29
<211> LENGTH: 2172
<212> TYPE: DNA
<213> ORGANISM: Corynebacterium glutamicum
<220> FEATURE:
<221> NAME/KEY: CDS
<222> LOCATION: (101)..(2149)
<223> OTHER INFORMATION: RXN01943

<400> SEQUENCE: 29
ccgattcttt ttcggcccaa ttcgtaacgg cgatcctctt aagtggacaa gaaagtctct      60
tgcccgcggg agacagaccc tacgtttaga aaggtttgac atg gcg tcc aaa ctg       115
                                             Met Ala Ser Lys Leu
                                              1               5 acg acg aca tcg caa cat att ctg gaa aac ctt ggt gga cca gac aat      163
Thr Thr Thr Ser Gln His Ile Leu Glu Asn Leu Gly Gly Pro Asp Asn
                10                  15                  20 att act tcg atg act cac tgt gcg act cgc ctt cgc ttc caa gtg aag      211
Ile Thr Ser Met Thr His Cys Ala Thr Arg Leu Arg Phe Gln Val Lys
            25                  30                  35 gat caa tcc att gtt gat caa caa gaa att gac tcc gac cca tca gtt      259
Asp Gln Ser Ile Val Asp Gln Gln Glu Ile Asp Ser Asp Pro Ser Val
        40                  45                  50 ctt ggc gta gta ccc caa gga tcc acc ggt atg cag gtg gtg atg ggt      307
Leu Gly Val Val Pro Gln Gly Ser Thr Gly Met Gln Val Val Met Gly
```

|  |  |  |  |  |  |  |  |  |  |  |  |  |  |  |
|---|---|---|---|---|---|---|---|---|---|---|---|---|---|---|
|  |  | 55 |  |  |  |  | 60 |  |  |  |  | 65 |  |  |

```
gga tct gtt gca aac tat tac caa gaa atc ctc aaa ctt gat gga atg       355
Gly Ser Val Ala Asn Tyr Tyr Gln Glu Ile Leu Lys Leu Asp Gly Met
 70              75                  80                  85 aag cac ttc gcc gac ggt gaa gct aca gag agt tca tcc aag aag gaa       403
Lys His Phe Ala Asp Gly Glu Ala Thr Glu Ser Ser Ser Lys Lys Glu
                 90                  95                 100 tac ggc gga gtc cgt ggc aag tac tcg tgg att gac tac gcc ttc gag       451
Tyr Gly Gly Val Arg Gly Lys Tyr Ser Trp Ile Asp Tyr Ala Phe Glu
            105                 110                 115 ttc ttg tct gat act ttc cga cca atc ctg tgg gcc ctg ctt ggt gcc       499
Phe Leu Ser Asp Thr Phe Arg Pro Ile Leu Trp Ala Leu Leu Gly Ala
        120                 125                 130 tca ctg att att acc ttg ttg gtt ctt gcg gat act ttc ggt ttg caa       547
Ser Leu Ile Ile Thr Leu Leu Val Leu Ala Asp Thr Phe Gly Leu Gln
    135                 140                 145 gac ttc cgc gct cca atg gat gag cag cct gat act tat gta ttc ctg       595
Asp Phe Arg Ala Pro Met Asp Glu Gln Pro Asp Thr Tyr Val Phe Leu
150                 155                 160                 165 cac tcc atg tgg cgc tcg gtc ttc tac ttc ctg cca att atg gtt ggt       643
His Ser Met Trp Arg Ser Val Phe Tyr Phe Leu Pro Ile Met Val Gly
                170                 175                 180 gcc acc gca gct cga aag ctc ggc gca aac gag tgg att ggt gca gct       691
Ala Thr Ala Ala Arg Lys Leu Gly Ala Asn Glu Trp Ile Gly Ala Ala
            185                 190                 195 att cca gcc gca ctt ctt act cca gaa ttc ttg gca ctg ggt tct gcc       739
Ile Pro Ala Ala Leu Leu Thr Pro Glu Phe Leu Ala Leu Gly Ser Ala
        200                 205                 210 ggc gat acc gtc aca gtc ttt ggc ctg cca atg gtt ctg aat gac tac       787
Gly Asp Thr Val Thr Val Phe Gly Leu Pro Met Val Leu Asn Asp Tyr
215                 220                 225 tcc gga cag gta ttc cca ccg ctg att gca gca att ggt ctg tac tgg       835
Ser Gly Gln Val Phe Pro Pro Leu Ile Ala Ala Ile Gly Leu Tyr Trp
230                 235                 240                 245 gtg gaa aag gga ctg aag aag atc atc cct gaa gca gtc caa atg gtg       883
Val Glu Lys Gly Leu Lys Lys Ile Ile Pro Glu Ala Val Gln Met Val
                250                 255                 260 ttc gtc cca ttc ttc tcc ctg ctg att atg atc cca gcg acc gca ttc       931
Phe Val Pro Phe Phe Ser Leu Leu Ile Met Ile Pro Ala Thr Ala Phe
            265                 270                 275 ctg ctt gga cct ttc ggc atc ggt gtt ggt aac gga att tcc aac ctg       979
Leu Leu Gly Pro Phe Gly Ile Gly Val Gly Asn Gly Ile Ser Asn Leu
        280                 285                 290 ctt gaa gcg att aac aac ttc agc cca ttt att ctt tcc atc gtt atc      1027
Leu Glu Ala Ile Asn Asn Phe Ser Pro Phe Ile Leu Ser Ile Val Ile
295                 300                 305 cca ttg ctc tac cca ttc ttg gtt cca ctt gga ttg cac tgg cca cta      1075
Pro Leu Leu Tyr Pro Phe Leu Val Pro Leu Gly Leu His Trp Pro Leu
310                 315                 320                 325 aac gcc atc atg atc cag aac atc aac acc ctg ggt tac gac ttc att      1123
Asn Ala Ile Met Ile Gln Asn Ile Asn Thr Leu Gly Tyr Asp Phe Ile
                330                 335                 340 cag gga cca atg ggt gcc tgg aac ttc gcc tgc ttc ggc ctg gtc acc      1171
Gln Gly Pro Met Gly Ala Trp Asn Phe Ala Cys Phe Gly Leu Val Thr
            345                 350                 355 ggc gtg ttc ttg ctc tcc att aag gaa cga aac aag gcc atg cgt cag      1219
Gly Val Phe Leu Leu Ser Ile Lys Glu Arg Asn Lys Ala Met Arg Gln
        360                 365                 370 gtt tcc ctg ggt ggc atg ttg gct ggt ttg ctc ggc ggc att tcc gag      1267
Val Ser Leu Gly Gly Met Leu Ala Gly Leu Leu Gly Gly Ile Ser Glu
```

```
                Val Ser Leu Gly Gly Met Leu Ala Gly Leu Leu Gly Ile Ser Glu
                    375                 380                 385 cct tcc ctc tac ggt gtt ctg ctc cga ttc aag aag acc tac ttc cgc         1315
Pro Ser Leu Tyr Gly Val Leu Leu Arg Phe Lys Lys Thr Tyr Phe Arg
390                 395                 400                 405 ctc ctg ccg ggt tgt ttg gca ggc ggt atc gtg atg ggc atc ttc gac         1363
Leu Leu Pro Gly Cys Leu Ala Gly Gly Ile Val Met Gly Ile Phe Asp
                410                 415                 420 atc aag gcg tac gct ttc gtg ttc acc tcc ttg ctt acc atc cca gca         1411
Ile Lys Ala Tyr Ala Phe Val Phe Thr Ser Leu Leu Thr Ile Pro Ala
            425                 430                 435 atg gac cca tgg ttg ggc tac acc att ggt atc gca gtt gca ttc ttc         1459
Met Asp Pro Trp Leu Gly Tyr Thr Ile Gly Ile Ala Val Ala Phe Phe
        440                 445                 450 gtt tcc atg ttc ctt gtt ctc gca ctg gac tac cgt tcc aac gaa gag         1507
Val Ser Met Phe Leu Val Leu Ala Leu Asp Tyr Arg Ser Asn Glu Glu
    455                 460                 465 cgc gat gag gca cgt gca aag gtt gct gct gac aag cag gca gaa gaa         1555
Arg Asp Glu Ala Arg Ala Lys Val Ala Ala Asp Lys Gln Ala Glu Glu
470                 475                 480                 485 gat ctg aag gca gaa gct aat gca act cct gca gct cca gta gct gct         1603
Asp Leu Lys Ala Glu Ala Asn Ala Thr Pro Ala Ala Pro Val Ala Ala
                490                 495                 500 gca ggt gcg gga gcc ggt gca ggt gca gga gcc gct gct ggc gct gca         1651
Ala Gly Ala Gly Ala Gly Ala Gly Ala Gly Ala Ala Gly Ala Ala
                505                 510                 515 acc gcc gtg gca gct aag ccg aag ctg gcc gct ggg gaa gta gtg gac         1699
Thr Ala Val Ala Ala Lys Pro Lys Leu Ala Ala Gly Glu Val Val Asp
            520                 525                 530 att gtt tcc cca ctc gaa ggc aag gca att cca ctt tct gaa gta cct         1747
Ile Val Ser Pro Leu Glu Gly Lys Ala Ile Pro Leu Ser Glu Val Pro
        535                 540                 545 gac cca atc ttt gca gca ggc aag ctt gga cca ggc att gca atc caa         1795
Asp Pro Ile Phe Ala Ala Gly Lys Leu Gly Pro Gly Ile Ala Ile Gln
550                 555                 560                 565 cca act gga aac acc gtt gtt gct cca gca gac gct act gtc atc ctt         1843
Pro Thr Gly Asn Thr Val Val Ala Pro Ala Asp Ala Thr Val Ile Leu
                570                 575                 580 gtc cag aaa tct gga cac gca gtg gca ttg cgc tta gat agc gga gtt         1891
Val Gln Lys Ser Gly His Ala Val Ala Leu Arg Leu Asp Ser Gly Val
                585                 590                 595 gaa atc ctt gtc cac gtt gga ttg gac acc gtg caa ttg ggc ggc gaa         1939
Glu Ile Leu Val His Val Gly Leu Asp Thr Val Gln Leu Gly Gly Glu
            600                 605                 610 ggc ttc acc gtt cac gtt gag cgc agg cag caa gtc aag gcg ggg gat         1987
Gly Phe Thr Val His Val Glu Arg Arg Gln Gln Val Lys Ala Gly Asp
        615                 620                 625 cca ctg atc act ttt gac gct gac ttc att cga tcc aag gat cta cct         2035
Pro Leu Ile Thr Phe Asp Ala Asp Phe Ile Arg Ser Lys Asp Leu Pro
630                 635                 640                 645 ttg atc acc cca gtt gtg gtg tct aac gcc gcg aaa ttc ggt gaa att         2083
Leu Ile Thr Pro Val Val Val Ser Asn Ala Ala Lys Phe Gly Glu Ile
                650                 655                 660 gaa ggt att cct gca gat cag gca aat tct tcc acg act gtg atc aag         2131
Glu Gly Ile Pro Ala Asp Gln Ala Asn Ser Ser Thr Thr Val Ile Lys
                665                 670                 675 gtc aac ggc aag aac gag taacctggga tccatgttgc gca                       2172
Val Asn Gly Lys Asn Glu
            680
```

<210> SEQ ID NO 30
<211> LENGTH: 683
<212> TYPE: PRT
<213> ORGANISM: Corynebacterium glutamicum

<400> SEQUENCE: 30

```
Met Ala Ser Lys Leu Thr Thr Thr Ser Gln His Ile Leu Glu Asn Leu
 1               5                  10                  15

Gly Gly Pro Asp Asn Ile Thr Ser Met Thr His Cys Ala Thr Arg Leu
             20                  25                  30

Arg Phe Gln Val Lys Asp Gln Ser Ile Val Asp Gln Gln Glu Ile Asp
         35                  40                  45

Ser Asp Pro Ser Val Leu Gly Val Pro Gln Gly Ser Thr Gly Met
     50                  55                  60

Gln Val Val Met Gly Gly Ser Val Ala Asn Tyr Tyr Gln Glu Ile Leu
 65                  70                  75                  80

Lys Leu Asp Gly Met Lys His Phe Ala Asp Gly Glu Ala Thr Glu Ser
                 85                  90                  95

Ser Ser Lys Lys Glu Tyr Gly Gly Val Arg Gly Lys Tyr Ser Trp Ile
            100                 105                 110

Asp Tyr Ala Phe Glu Phe Leu Ser Asp Thr Phe Arg Pro Ile Leu Trp
        115                 120                 125

Ala Leu Leu Gly Ala Ser Leu Ile Ile Thr Leu Leu Val Leu Ala Asp
    130                 135                 140

Thr Phe Gly Leu Gln Asp Phe Arg Ala Pro Met Asp Glu Gln Pro Asp
145                 150                 155                 160

Thr Tyr Val Phe Leu His Ser Met Trp Arg Ser Val Phe Tyr Phe Leu
                165                 170                 175

Pro Ile Met Val Gly Ala Thr Ala Ala Arg Lys Leu Gly Ala Asn Glu
            180                 185                 190

Trp Ile Gly Ala Ala Ile Pro Ala Ala Leu Leu Thr Pro Glu Phe Leu
        195                 200                 205

Ala Leu Gly Ser Ala Gly Asp Thr Val Thr Val Phe Gly Leu Pro Met
    210                 215                 220

Val Leu Asn Asp Tyr Ser Gly Gln Val Phe Pro Pro Leu Ile Ala Ala
225                 230                 235                 240

Ile Gly Leu Tyr Trp Val Glu Lys Gly Leu Lys Ile Ile Pro Glu
                245                 250                 255

Ala Val Gln Met Val Phe Val Pro Phe Phe Ser Leu Leu Ile Met Ile
            260                 265                 270

Pro Ala Thr Ala Phe Leu Leu Gly Pro Phe Gly Ile Gly Val Gly Asn
        275                 280                 285

Gly Ile Ser Asn Leu Leu Glu Ala Ile Asn Asn Phe Ser Pro Phe Ile
    290                 295                 300

Leu Ser Ile Val Ile Pro Leu Leu Tyr Pro Phe Leu Val Pro Leu Gly
305                 310                 315                 320

Leu His Trp Pro Leu Asn Ala Ile Met Ile Gln Asn Ile Asn Thr Leu
                325                 330                 335

Gly Tyr Asp Phe Ile Gln Gly Pro Met Gly Ala Trp Asn Phe Ala Cys
            340                 345                 350

Phe Gly Leu Val Thr Gly Val Phe Leu Ser Ile Lys Glu Arg Asn
        355                 360                 365

Lys Ala Met Arg Gln Val Ser Leu Gly Gly Met Leu Ala Gly Leu Leu
    370                 375                 380
```

```
Gly Gly Ile Ser Glu Pro Ser Leu Tyr Gly Val Leu Arg Phe Lys
385                 390                 395                 400

Lys Thr Tyr Phe Arg Leu Leu Pro Gly Cys Leu Ala Gly Ile Val
            405                 410                 415

Met Gly Ile Phe Asp Ile Lys Ala Tyr Ala Phe Val Phe Thr Ser Leu
            420                 425                 430

Leu Thr Ile Pro Ala Met Asp Pro Trp Leu Gly Tyr Thr Ile Gly Ile
            435                 440                 445

Ala Val Ala Phe Phe Val Ser Met Phe Leu Val Leu Ala Leu Asp Tyr
450                 455                 460

Arg Ser Asn Glu Glu Arg Asp Glu Ala Arg Ala Lys Val Ala Ala Asp
465                 470                 475                 480

Lys Gln Ala Glu Glu Asp Leu Lys Ala Glu Ala Asn Ala Thr Pro Ala
                485                 490                 495

Ala Pro Val Ala Ala Gly Ala Gly Ala Gly Ala Gly Ala
            500                 505                 510

Ala Ala Gly Ala Ala Thr Ala Val Ala Ala Lys Pro Lys Leu Ala Ala
            515                 520                 525

Gly Glu Val Val Asp Ile Val Ser Pro Leu Glu Gly Lys Ala Ile Pro
530                 535                 540

Leu Ser Glu Val Pro Asp Pro Ile Phe Ala Ala Gly Lys Leu Gly Pro
545                 550                 555                 560

Gly Ile Ala Ile Gln Pro Thr Gly Asn Thr Val Val Ala Pro Ala Asp
            565                 570                 575

Ala Thr Val Ile Leu Val Gln Lys Ser Gly His Ala Val Ala Leu Arg
            580                 585                 590

Leu Asp Ser Gly Val Glu Ile Leu Val His Val Gly Leu Asp Thr Val
            595                 600                 605

Gln Leu Gly Gly Glu Gly Phe Thr Val His Val Glu Arg Arg Gln Gln
    610                 615                 620

Val Lys Ala Gly Asp Pro Leu Ile Thr Phe Asp Ala Asp Phe Ile Arg
625                 630                 635                 640

Ser Lys Asp Leu Pro Leu Ile Thr Pro Val Val Ser Asn Ala Ala
                645                 650                 655

Lys Phe Gly Glu Ile Glu Gly Ile Pro Ala Asp Gln Ala Asn Ser Ser
            660                 665                 670

Thr Thr Val Ile Lys Val Asn Gly Lys Asn Glu
            675                 680

<210> SEQ ID NO 31
<211> LENGTH: 1339
<212> TYPE: DNA
<213> ORGANISM: Corynebacterium glutamicum
<220> FEATURE:
<221> NAME/KEY: CDS
<222> LOCATION: (101)..(1339)
<223> OTHER INFORMATION: FRXA02191

<400> SEQUENCE: 31 ccgattctttt tcggcccaa ttcgtaacgg cgatcctctt aagtggacaa gaaagtctct      60
tgcccgcggg agacagaccc tacgtttaga aaggtttgac atg gcg tcc aaa ctg     115
                                              Met Ala Ser Lys Leu
                                                1               5 acg acg aca tcg caa cat att ctg gaa aac ctt ggt gga cca gac aat     163
Thr Thr Thr Ser Gln His Ile Leu Glu Asn Leu Gly Gly Pro Asp Asn
            10                  15                  20
```

-continued

| | |
|---|---|
| att act tcg atg act cac tgt gcg act cgc ctt cgc ttc caa gtg aag<br>Ile Thr Ser Met Thr His Cys Ala Thr Arg Leu Arg Phe Gln Val Lys<br>            25                    30                  35 | 211 |
| gat caa tcc att gtt gat caa caa gaa att gac tcc gac cca tca gtt<br>Asp Gln Ser Ile Val Asp Gln Gln Glu Ile Asp Ser Asp Pro Ser Val<br>        40                    45                    50 | 259 |
| ctt ggc gta gta ccc caa gga tcc acc ggt atg cag gtg gtg atg ggt<br>Leu Gly Val Val Pro Gln Gly Ser Thr Gly Met Gln Val Val Met Gly<br>55                    60                    65 | 307 |
| gga tct gtt gca aac tat tac caa gaa atc ctc aaa ctt gat gga atg<br>Gly Ser Val Ala Asn Tyr Tyr Gln Glu Ile Leu Lys Leu Asp Gly Met<br>70                    75                    80                    85 | 355 |
| aag cac ttc gcc gac ggt gaa gct aca gag agt tca tcc aag aag gaa<br>Lys His Phe Ala Asp Gly Glu Ala Thr Glu Ser Ser Ser Lys Lys Glu<br>                90                    95                  100 | 403 |
| tac ggc gga gtc cgt ggc aag tac tcg tgg att gac tac gcc ttc gag<br>Tyr Gly Gly Val Arg Gly Lys Tyr Ser Trp Ile Asp Tyr Ala Phe Glu<br>              105                    110                  115 | 451 |
| ttc ttg tct gat act ttc cga cca atc ctg tgg gcc ctg ctt ggt gcc<br>Phe Leu Ser Asp Thr Phe Arg Pro Ile Leu Trp Ala Leu Leu Gly Ala<br>            120                    125                  130 | 499 |
| tca ctg att att acc ttg ttg gtt ctt gcg gat act ttc ggt ttg caa<br>Ser Leu Ile Ile Thr Leu Leu Val Leu Ala Asp Thr Phe Gly Leu Gln<br>135                    140                    145 | 547 |
| gac ttc cgc gct cca atg gat gag cag cct gat act tat gta ttc ctg<br>Asp Phe Arg Ala Pro Met Asp Glu Gln Pro Asp Thr Tyr Val Phe Leu<br>150                    155                    160                  165 | 595 |
| cac tcc atg tgg cgc tcg gtc ttc tac ttc ctg cca att atg gtt ggt<br>His Ser Met Trp Arg Ser Val Phe Tyr Phe Leu Pro Ile Met Val Gly<br>            170                    175                  180 | 643 |
| gcc acc gca gct cga aag ctc ggc gca aac gag tgg att ggt gca gct<br>Ala Thr Ala Ala Arg Lys Leu Gly Ala Asn Glu Trp Ile Gly Ala Ala<br>            185                    190                  195 | 691 |
| att cca gcc gca ctt ctt act cca gaa ttc ttg gca ctg ggt tct gcc<br>Ile Pro Ala Ala Leu Leu Thr Pro Glu Phe Leu Ala Leu Gly Ser Ala<br>            200                    205                  210 | 739 |
| ggc gat acc gtc aca gtc ttt ggc ctg cca atg gtt ctg aat gac tac<br>Gly Asp Thr Val Thr Val Phe Gly Leu Pro Met Val Leu Asn Asp Tyr<br>215                    220                    225 | 787 |
| tcc gga cag gta ttc cca ccg ctg att gca gca att ggt ctg tac tgg<br>Ser Gly Gln Val Phe Pro Pro Leu Ile Ala Ala Ile Gly Leu Tyr Trp<br>230                    235                    240                  245 | 835 |
| gtg gaa aag gga ctg aag aag atc atc cct gaa gca gtc caa atg gtg<br>Val Glu Lys Gly Leu Lys Lys Ile Ile Pro Glu Ala Val Gln Met Val<br>                250                    255                  260 | 883 |
| ttc gtc cca ttc ttc tcc ctg ctg att atg atc cca gcg acc gca ttc<br>Phe Val Pro Phe Phe Ser Leu Leu Ile Met Ile Pro Ala Thr Ala Phe<br>            265                    270                  275 | 931 |
| ctg ctt gga cct ttc ggc atc ggt gtt ggt aac gga att tcc aac ctg<br>Leu Leu Gly Pro Phe Gly Ile Gly Val Gly Asn Gly Ile Ser Asn Leu<br>            280                    285                  290 | 979 |
| ctt gaa gcg att aac aac ttc agc cca ttt att ctt tcc atc gtt atc<br>Leu Glu Ala Ile Asn Asn Phe Ser Pro Phe Ile Leu Ser Ile Val Ile<br>295                    300                    305 | 1027 |
| cca ttg ctc tac cca ttc ttg gtt cca ctt gga ttg cac tgg cca cta<br>Pro Leu Leu Tyr Pro Phe Leu Val Pro Leu Gly Leu His Trp Pro Leu<br>310                    315                    320                  325 | 1075 |
| aac gcc atc atg atc cag aac atc aac acc ctg ggt tac gac ttc att<br>Asn Ala Ile Met Ile Gln Asn Ile Asn Thr Leu Gly Tyr Asp Phe Ile | 1123 |

```
                    330              335              340
cag gga cca atg ggt gcc tgg aac ttc gcc tgc ttc ggc ctg gtc acc      1171
Gln Gly Pro Met Gly Ala Trp Asn Phe Ala Cys Phe Gly Leu Val Thr
                345              350              355 ggc gtg ttc ttg ctc tcc att aag gaa cga aac aag gcc atg cgt cag      1219
Gly Val Phe Leu Leu Ser Ile Lys Glu Arg Asn Lys Ala Met Arg Gln
            360              365              370 gtt tcc ctg ggt ggc atg ttg gct ggt ttg ctc ggc ggc att tcc gag      1267
Val Ser Leu Gly Gly Met Leu Ala Gly Leu Leu Gly Gly Ile Ser Glu
        375              380              385 cct tcc ctc tac ggt gtt ctg ctc cga ttc aag aag acc tac ttc cgc      1315
Pro Ser Leu Tyr Gly Val Leu Leu Arg Phe Lys Lys Thr Tyr Phe Arg
390              395              400              405 ctc ctg ccg ggt tgt ttg gca gca                                       1339
Leu Leu Pro Gly Cys Leu Ala Ala
                410

<210> SEQ ID NO 32
<211> LENGTH: 413
<212> TYPE: PRT
<213> ORGANISM: Corynebacterium glutamicum

<400> SEQUENCE: 32

Met Ala Ser Lys Leu Thr Thr Thr Ser Gln His Ile Leu Glu Asn Leu
 1               5                   10                  15

Gly Gly Pro Asp Asn Ile Thr Ser Met Thr His Cys Ala Thr Arg Leu
            20                  25                  30

Arg Phe Gln Val Lys Asp Gln Ser Ile Val Asp Gln Glu Ile Asp
        35                  40                  45

Ser Asp Pro Ser Val Leu Gly Val Val Pro Gln Gly Ser Thr Gly Met
    50                  55                  60

Gln Val Val Met Gly Gly Ser Val Ala Asn Tyr Tyr Gln Glu Ile Leu
65                  70                  75                  80

Lys Leu Asp Gly Met Lys His Phe Ala Asp Gly Glu Ala Thr Glu Ser
                85                  90                  95

Ser Ser Lys Lys Glu Tyr Gly Gly Val Arg Gly Lys Tyr Ser Trp Ile
            100                 105                 110

Asp Tyr Ala Phe Glu Phe Leu Ser Asp Thr Phe Arg Pro Ile Leu Trp
        115                 120                 125

Ala Leu Leu Gly Ala Ser Leu Ile Ile Thr Leu Leu Val Leu Ala Asp
    130                 135                 140

Thr Phe Gly Leu Gln Asp Phe Arg Ala Pro Met Asp Glu Gln Pro Asp
145                 150                 155                 160

Thr Tyr Val Phe Leu His Ser Met Trp Arg Ser Val Phe Tyr Phe Leu
                165                 170                 175

Pro Ile Met Val Gly Ala Thr Ala Ala Arg Lys Leu Gly Ala Asn Glu
            180                 185                 190

Trp Ile Gly Ala Ala Ile Pro Ala Ala Leu Leu Thr Pro Glu Phe Leu
        195                 200                 205

Ala Leu Gly Ser Ala Gly Asp Thr Val Thr Val Phe Gly Leu Pro Met
    210                 215                 220

Val Leu Asn Asp Tyr Ser Gly Gln Val Phe Pro Pro Leu Ile Ala Ala
225                 230                 235                 240

Ile Gly Leu Tyr Trp Val Glu Lys Gly Leu Lys Lys Ile Ile Pro Glu
                245                 250                 255

Ala Val Gln Met Val Phe Val Pro Phe Phe Ser Leu Leu Ile Met Ile
```

-continued

```
                260                 265                 270
Pro Ala Thr Ala Phe Leu Leu Gly Pro Phe Gly Ile Gly Val Gly Asn
                275                 280                 285
Gly Ile Ser Asn Leu Leu Glu Ala Ile Asn Asn Phe Ser Pro Phe Ile
        290                 295                 300
Leu Ser Ile Val Ile Pro Leu Leu Tyr Pro Phe Leu Val Pro Leu Gly
305                 310                 315                 320
Leu His Trp Pro Leu Asn Ala Ile Met Ile Gln Asn Ile Asn Thr Leu
                325                 330                 335
Gly Tyr Asp Phe Ile Gln Gly Pro Met Gly Ala Trp Asn Phe Ala Cys
                340                 345                 350
Phe Gly Leu Val Thr Gly Val Phe Leu Leu Ser Ile Lys Glu Arg Asn
        355                 360                 365
Lys Ala Met Arg Gln Val Ser Leu Gly Gly Met Leu Ala Gly Leu Leu
    370                 375                 380
Gly Gly Ile Ser Glu Pro Ser Leu Tyr Gly Val Leu Leu Arg Phe Lys
385                 390                 395                 400
Lys Thr Tyr Phe Arg Leu Leu Pro Gly Cys Leu Ala Ala
                405                 410
```

<210> SEQ ID NO 33
<211> LENGTH: 428
<212> TYPE: DNA
<213> ORGANISM: Corynebacterium glutamicum
<220> FEATURE:
<221> NAME/KEY: CDS
<222> LOCATION: (1)..(405)
<223> OTHER INFORMATION: FRXA01943

<400> SEQUENCE: 33

```
cct gac cca atc ttt gca gca ggc aag ctt gga cca ggc att gca atc      48
Pro Asp Pro Ile Phe Ala Ala Gly Lys Leu Gly Pro Gly Ile Ala Ile
  1               5                  10                  15 caa cca act gga aac acc gtt gtt gct cca gca gac gct act gtc atc      96
Gln Pro Thr Gly Asn Thr Val Val Ala Pro Ala Asp Ala Thr Val Ile
             20                  25                  30 ctt gtc cag aaa tct gga cac gca gtg gca ttg cgc tta gat agc gga     144
Leu Val Gln Lys Ser Gly His Ala Val Ala Leu Arg Leu Asp Ser Gly
         35                  40                  45 gtt gaa atc ctt gtc cac gtt gga ttg gac acc gtg caa ttg ggc ggc     192
Val Glu Ile Leu Val His Val Gly Leu Asp Thr Val Gln Leu Gly Gly
     50                  55                  60 gaa ggc ttc acc gtt cac gtt gag cgc agg cag caa gtc aag gcg ggg     240
Glu Gly Phe Thr Val His Val Glu Arg Arg Gln Gln Val Lys Ala Gly
 65                  70                  75                  80 gat cca ctg atc act ttt gac gct gac ttc att cga tcc aag gat cta     288
Asp Pro Leu Ile Thr Phe Asp Ala Asp Phe Ile Arg Ser Lys Asp Leu
                 85                  90                  95 cct ttg atc acc cca gtt gtg gtg tct aac gcc gcg aaa ttc ggt gaa     336
Pro Leu Ile Thr Pro Val Val Val Ser Asn Ala Ala Lys Phe Gly Glu
            100                 105                 110 att gaa ggt att cct gca gat cag gca aat tct tcc acg act gtg atc     384
Ile Glu Gly Ile Pro Ala Asp Gln Ala Asn Ser Ser Thr Thr Val Ile
        115                 120                 125 aag gtc aac ggc aag aac gag taacctggga tccatgttgc gca               428
Lys Val Asn Gly Lys Asn Glu
    130                 135
```

<210> SEQ ID NO 34

-continued

```
<211> LENGTH: 135
<212> TYPE: PRT
<213> ORGANISM: Corynebacterium glutamicum

<400> SEQUENCE: 34

Pro Asp Pro Ile Phe Ala Ala Gly Lys Leu Gly Pro Gly Ile Ala Ile
1               5                   10                  15

Gln Pro Thr Gly Asn Thr Val Val Ala Pro Ala Asp Ala Thr Val Ile
            20                  25                  30

Leu Val Gln Lys Ser Gly His Ala Val Ala Leu Arg Leu Asp Ser Gly
        35                  40                  45

Val Glu Ile Leu Val His Val Gly Leu Asp Thr Val Gln Leu Gly Gly
    50                  55                  60

Glu Gly Phe Thr Val His Val Glu Arg Arg Gln Gln Val Lys Ala Gly
65                  70                  75                  80

Asp Pro Leu Ile Thr Phe Asp Ala Asp Phe Ile Arg Ser Lys Asp Leu
                85                  90                  95

Pro Leu Ile Thr Pro Val Val Val Ser Asn Ala Ala Lys Phe Gly Glu
            100                 105                 110

Ile Glu Gly Ile Pro Ala Asp Gln Ala Asn Ser Ser Thr Thr Val Ile
        115                 120                 125

Lys Val Asn Gly Lys Asn Glu
130                 135
```

CORYNEBACTERIUM GLUTAMICUM GENES ENCODING PHOSPHOENOLPYRUVATE: SUGAR PHOSPHOTRANSFERASE SYSTEM PROTEINS

RELATED APPLICATIONS

This application is a divisional application of U.S. patent application Ser. No.: 11/061,298, filed Feb. 17, 2005, pending which is a continuation application of U.S. patent application No.: 09/604,231, filed Jun. 27, 2000 (issued as U.S. Pat. No. 6,884,614 on Apr. 26, 2005), which claims priority to U.S. Provisional Patent Application No.: 60/142,691, filed on Jul. 1, 1999 (expired), and also to U.S. Provisional Patent Application No.: 60/150,310, filed on Aug. 23, 1999 (expired). This application also claims priority to German Patent Application No.: 19942095.5, filed on Sep. 3, 1999, and also to German Patent Application No.: 19942097.1, filed on Sep. 3, 1999. The entire contents of each of the foregoing U.S. and German patent applications are incorporated herein by this reference.

INCORPORATION OF MATERIAL SUBMITTED ON COMPACT DISCS

This application incorporates herein by reference the material contained on the compact discs submitted herewith as part of this application. Specifically, the file "seqlist" (114 KB) contained on each of Copy 1, Copy 2 and the CRF copy of the Sequence Listing is hereby incorporated herein by reference. This file was created on Jul. 29, 2006.

BACKGROUND OF THE INVENTION

Certain products and by-products of naturally-occurring metabolic processes in cells have utility in a wide array of industries, including the food, feed, cosmetics, and pharmaceutical industries. These molecules, collectively termed 'fine chemicals', include organic acids, both proteinogenic and non-proteinogenic amino acids, nucleotides and nucleosides, lipids and fatty acids, diols, carbohydrates, aromatic compounds, vitamins and cofactors, and enzymes. Their production is most conveniently performed through large-scale culture of bacteria developed to produce and secrete large quantities of a particular desired molecule. One particularly useful organism for this purpose is *Corynebacterium glutamicum*, a gram positive, nonpathogenic bacterium. Through strain selection, a number of mutant strains have been developed which produce an array of desirable compounds. However, selection of strains improved for the production of a particular molecule is a time-consuming and difficult process.

SUMMARY OF THE INVENTION

The invention provides novel bacterial nucleic acid molecules which have a variety of uses. These uses include the identification of microorganisms which can be used to produce fine chemicals, the modulation of fine chemical production in *C. glutamicum* or related bacteria, the typing or identification of *C. glutamicum* or related bacteria, as reference points for mapping the *C. glutamicum* genome, and as markers for transformation. These novel nucleic acid molecules encode proteins, referred to herein as phosphoenolpyruvate: sugar phosphotransferase system (PTS) proteins.

*C. glutamicum* is a gram positive, aerobic bacterium which is commonly used in industry for the large-scale production of a variety of fine chemicals, and also for the degradation of hydrocarbons (such as in petroleum spills) and for the oxidation of terpenoids. The PTS nucleic acid molecules of the invention, therefore, can be used to identify microorganisms which can be used to produce fine chemicals, e.g., by fermentation processes. Modulation of the expression of the PTS nucleic acids of the invention, or modification of the sequence of the PTS nucleic acid molecules of the invention, can be used to modulate the production of one or more fine chemicals from a microorganism (e.g., to improve the yield or production of one or more fine chemicals from a *Corynebacterium* or *Brevibacterium* species).

The PTS nucleic acids of the invention may also be used to identify an organism as being *Corynebacterium glutamicum* or a close relative thereof, or to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present. Although *Corynebacterium glutamicum* itself is nonpathogenic, it is related to species pathogenic in humans, such as *Corynebacterium diphtheriae* (the causative agent of diphtheria); the detection of such organisms is of significant clinical relevance.

The PTS nucleic acid molecules of the invention may also serve as reference points for mapping of the *C. glutamicum* genome, or of genomes of related organisms. Similarly, these molecules, or variants or portions thereof, may serve as markers for genetically engineered *Corynebacterium* or *Brevibacterium* species.

The PTS proteins encoded by the novel nucleic acid molecules of the invention are capable of, for example, transporting high-energy carbon-containing molecules such as glucose into *C. glutamicum*, or of participating in intracellular signal transduction in this microorganism. Given the availability of cloning vectors for use in *Corynebacterium glutamicum*, such as those disclosed in Sinskey et al., U.S. Pat. No. 4,649,119, and techniques for genetic manipulation of *C. glutamicum* and the related *Brevibacterium* species (e.g., *lactofermentum*) (Yoshihama et al, *J. Bacteriol.* 162: 591-597 (1985); Katsumata et al., *J. Bacteriol.* 159: 306-311 (1984); and Santamaria et al., *J. Gen. Microbiol.* 130: 2237-2246 (1984)), the nucleic acid molecules of the invention may be utilized in the genetic engineering of this organism to make it a better or more efficient producer of one or more fine chemicals.

The PTS molecules of the invention may be modified such that the yield, production, and/or efficiency of production of one or more fine chemicals is improved. For example, by modifying a PTS protein involved in the uptake of glucose such that it is optimized in activity, the quantity of glucose uptake or the rate at which glucose is translocated into the cell may be increased. The breakdown of glucose and other sugars within the cell provides energy that may be used to drive energetically unfavorable biochemical reactions, such as those involved in the biosynthesis of fine chemicals. This breakdown also provides intermediate and precursor molecules necessary for the biosynthesis of certain fine chemicals, such as amino acids, vitamins and cofactors. By increasing the amount of intracellular high-energy carbon molecules through modification of the PTS molecules of the invention, one may therefore increase both the energy available to perform metabolic pathways necessary for the production of one or more fine chemicals, and also the intracellular pools of metabolites necessary for such production.

Further, the PTS molecules of the invention may be involved in one or more intracellular signal transduction pathways which may affect the yields and/or rate of production of one or more fine chemical from *C. glutamicum*. For example, proteins necessary for the import of one or more sugars from the extracellular medium (e.g., HPr, Enzyme I, or a member of an Enzyme II complex) are frequently posttranslationally modified upon the presence of a sufficient quantity of the sugar in the cell, such that they are no longer able to import that sugar. While this quantity of sugar at which the transport system is shut off may be sufficient to sustain the normal functioning of the cell, it may be limiting for the overproduction of the desired fine chemical. Thus, it may be desirable to modify the PTS proteins of the invention such that they are no longer responsive to such negative regulation, thereby permitting greater intracellular concentrations of one or more sugars to be achieved, and, by extension, more efficient production or greater yields of one or more fine chemicals from organisms containing such mutant PTS proteins.

This invention provides novel nucleic acid molecules which encode proteins, referred to herein as phosphoenolpyruvate:sugar phosphotransferase system (PTS) proteins, which are capable of, for example, participating in the import of high-energy carbon molecules (e.g., glucose, fructose, or sucrose) into *C. glutamicum*, and/or of participating in one or more *C. glutamicum* intracellular signal transduction pathways. Nucleic acid molecules encoding a PTS protein are referred to herein as PTS nucleic acid molecules. In a preferred embodiment, the PTS protein participates in the import of high-energy carbon molecules (e.g., glucose, fructose, or sucrose) into *C. glutamicum*, and also may participate in one or more *C. glutamicum* intracellular signal transduction pathways. Examples of such proteins include those encoded by the genes set forth in Table 1.

Accordingly, one aspect of the invention pertains to isolated nucleic acid molecules (e.g., cDNAs, DNAs, or RNAs) comprising a nucleotide sequence encoding a PTS protein or biologically active portions thereof, as well as nucleic acid fragments suitable as primers or hybridization probes for the detection or amplification of PTS-encoding nucleic acid (e.g., DNA or mRNA). In particularly preferred embodiments, the isolated nucleic acid molecule comprises one of the nucleotide sequences set forth in Appendix A or the coding region or a complement thereof of one of these nucleotide sequences. In other particularly preferred embodiments, the isolated nucleic acid molecule of the invention comprises a nucleotide sequence which hybridizes to or is at least about 50%, preferably at least about 60%, more preferably at least about 70%, 80% or 90%, and even more preferably at least about 95%, 96%, 97%, 98%, 99% or more homologous to a nucleotide sequence set forth in Appendix A, or a portion thereof. In other preferred embodiments, the isolated nucleic acid molecule encodes one of the amino acid sequences set forth in Appendix B. The preferred PTS proteins of the present invention also preferably possess at least one of the PTS activities described herein.

In another embodiment, the isolated nucleic acid molecule encodes a protein or portion thereof wherein the protein or portion thereof includes an amino acid sequence which is sufficiently homologous to an amino acid sequence of Appendix B, e.g., sufficiently homologous to an amino acid sequence of Appendix B such that the protein or portion thereof maintains a PTS activity. Preferably, the protein or portion thereof encoded by the nucleic acid molecule maintains the ability to participate in the import of high-energy carbon molecules (e.g., glucose, fructose, or sucrose) into *C. glutamicum*, and/or to participate in one or more *C. glutamicum* intracellular signal transduction pathways. In one embodiment, the protein encoded by the nucleic acid molecule is at least about 50%, preferably at least about 60%, and more preferably at least about 70%, 80%, or 90% and most preferably at least about 95%, 96%, 97%, 98%, or 99% or more homologous to an amino acid sequence of Appendix B (e.g., an entire amino acid sequence selected from those sequences set forth in Appendix B). In another preferred embodiment, the protein is a full length *C. glutamicum* protein which is substantially homologous to an entire amino acid sequence of Appendix B (encoded by an open reading frame shown in Appendix A).

In another preferred embodiment, the isolated nucleic acid molecule is derived from *C. glutamicum* and encodes a protein (e.g., a PTS fusion protein) which includes a biologically active domain which is at least about 50% or more homologous to one of the amino acid sequences of Appendix B and is able to participate in the import of high-energy carbon molecules (e.g., glucose, fructose, or sucrose) into *C. glutamicum*, and/or to participate in one or more *C. glutamicum* intracellular signal transduction pathways, or possesses one or more of the activities set forth in Table 1, and which also includes heterologous nucleic acid sequences encoding a heterologous polypeptide or regulatory regions.

In another embodiment, the isolated nucleic acid molecule is at least 15 nucleotides in length and hybridizes under stringent conditions to a nucleic acid molecule comprising a nucleotide sequence of Appendix A. Preferably, the isolated nucleic acid molecule corresponds to a naturally-occurring nucleic acid molecule. More preferably, the isolated nucleic acid encodes a naturally-occurring *C. glutamicum* PTS protein, or a biologically active portion thereof.

Another aspect of the invention pertains to vectors, e.g., recombinant expression vectors, containing the nucleic acid molecules of the invention, and host cells into which such vectors have been introduced. In one embodiment, such a host cell is used to produce a PTS protein by culturing the host cell in a suitable medium. The PTS protein can be then isolated from the medium or the host cell.

Yet another aspect of the invention pertains to a genetically altered microorganism in which a PTS gene has been introduced or altered. In one embodiment, the genome of the microorganism has been altered by the introduction of a nucleic acid molecule of the invention encoding wild-type or mutated PTS sequence as a transgene. In another embodiment, an endogenous PTS gene within the genome of the microorganism has been altered, e.g., functionally disrupted, by homologous recombination with an altered PTS gene. In another embodiment, an endogenous or introduced PTS gene in a microorganism has been altered by one or more point mutations, deletions, or inversions, but still encodes a functional PTS protein. In still another embodiment, one or more of the regulatory regions (e.g., a promoter, repressor, or inducer) of a PTS gene in a microorganism has been altered (e.g., by deletion, truncation, inversion, or point mutation) such that the expression of the PTS gene is modulated. In a preferred embodiment, the microorganism belongs to the genus *Corynebacterium* or *Brevibacterium*, with *Corynebacterium glutamicum* being particularly preferred. In a preferred embodiment, the microorganism is also utilized for the production of a desired compound, such as an amino acid, with lysine being particularly preferred.

In another aspect, the invention provides a method of identifying the presence or activity of *Cornyebacterium diphtheriae* in a subject. This method includes detection of one or more of the nucleic acid or amino acid sequences of the invention (e.g., the sequences set forth in Appendix A or Appendix B) in a subject, thereby detecting the presence or activity of *Corynebacterium diphtheriae* in the subject.

Still another aspect of the invention pertains to an isolated PTS protein or a portion, e.g., a biologically active portion, thereof. In a preferred embodiment, the isolated PTS protein or portion thereof can participate in the import of high-energy carbon molecules (e.g., glucose, fructose, or sucrose) into *C. glutamicum*, and also may participate in one or more *C. glutamicum* intracellular signal transduction pathways. In another preferred embodiment, the isolated PTS protein or portion thereof is sufficiently homologous to an amino acid sequence of Appendix B such that the protein or portion thereof maintains the ability to participate in the import of high-energy carbon molecules (e.g., glucose, fructose, or sucrose) into *C. glutamicum*, and/or to participate in one or more *C. glutamicum* intracellular signal transduction pathways.

The invention also provides an isolated preparation of a PTS protein. In preferred embodiments, the PTS protein comprises an amino acid sequence of Appendix B. In another preferred embodiment, the invention pertains to an isolated full length protein which is substantially homologous to an entire amino acid sequence of Appendix B (encoded by an open reading frame set forth in Appendix A). In yet another embodiment, the protein is at least about 50%, preferably at least about 60%, and more preferably at least about 70%, 80%, or 90%, and most preferably at least about 95%, 96%, 97%, 98%, or 99% or more homologous to an entire amino acid sequence of Appendix B. In other embodiments, the isolated PTS protein comprises an amino acid sequence which is at least about 50% or more homologous to one of the amino acid sequences of Appendix B and is able to participate in the import of high-energy carbon molecules (e.g., glucose, fructose, or sucrose) into *C. glutamicum*, and/or to participate in one or more *C. glutamicum* intracellular signal transduction pathways, or has one or more of the activities set forth in Table 1.

Alternatively, the isolated PTS protein can comprise an amino acid sequence which is encoded by a nucleotide sequence which hybridizes, e.g., hybridizes under stringent conditions, or is at least about 50%, preferably at least about 60%, more preferably at least about 70%, 80%, or 90%, and even more preferably at least about 95%, 96%, 97%, 98,%, or 99% or more homologous, to a nucleotide sequence of Appendix B. It is also preferred that the preferred forms of PTS proteins also have one or more of the PTS bioactivities described herein.

The PTS polypeptide, or a biologically active portion thereof, can be operatively linked to a non-PTS polypeptide to form a fusion protein. In preferred embodiments, this fusion protein has an activity which differs from that of the PTS protein alone. In other preferred embodiments, this fusion protein results in increased yields, production, and/or efficiency of production of a desired fine chemical from *C. glutamicum*. In particularly preferred embodiments, integration of this fusion protein into a host cell modulates the production of a desired compound from the cell.

In another aspect, the invention provides methods for screening molecules which modulate the activity of a PTS protein, either by interacting with the protein itself or a substrate or binding partner of the PTS protein, or by modulating the transcription or translation of a PTS nucleic acid molecule of the invention.

Another aspect of the invention pertains to a method for producing a fine chemical. This method involves the culturing of a cell containing a vector directing the expression of a PTS nucleic acid molecule of the invention, such that a fine chemical is produced. In a preferred embodiment, this method further includes the step of obtaining a cell containing such a vector, in which a cell is transfected with a vector directing the expression of a PTS nucleic acid. In another preferred embodiment, this method further includes the step of recovering the fine chemical from the culture. In a particularly preferred embodiment, the cell is from the genus *Corynebacterium* or *Brevibacterium*, or is selected from those strains set forth in Table 3.

Another aspect of the invention pertains to methods for modulating production of a molecule from a microorganism. Such methods include contacting the cell with an agent which modulates PTS protein activity or PTS nucleic acid expression such that a cell associated activity is altered relative to this same activity in the absence of the agent. In a preferred embodiment, the cell is modulated for the uptake of one or more sugars, such that the yields or rate of production of a desired fine chemical by this microorganism is improved. The agent which modulates PTS protein activity can be an agent which stimulates PTS protein activity or PTS nucleic acid expression. Examples of agents which stimulate PTS protein activity or PTS nucleic acid expression include small molecules, active PTS proteins, and nucleic acids encoding PTS proteins that have been introduced into the cell. Examples of agents which inhibit PTS activity or expression include small molecules, and antisense PTS nucleic acid molecules.

Another aspect of the invention pertains to methods for modulating yields of a desired compound from a cell, involving the introduction of a wild-type or mutant PTS gene into a cell, either maintained on a separate plasmid or integrated into the genome of the host cell. If integrated into the genome, such integration can random, or it can take place by homologous recombination such that the native gene is replaced by the introduced copy, causing the production of the desired compound from the cell to be modulated. In a preferred embodiment, said yields are increased. In another preferred embodiment, said chemical is a fine chemical. In a particularly preferred embodiment, said fine chemical is an amino acid. In especially preferred embodiments, said amino acid is L-lysine.

DETAILED DESCRIPTION OF THE INVENTION

The present invention provides PTS nucleic acid and protein molecules which are involved in the uptake of high-energy carbon molecules (e.g., sucrose, fructose, or glucose) into *C. glutamicum*, and may also participate in intracellular signal transduction pathways in this microorganism. The molecules of the invention may be utilized in the modulation of production of fine chemicals from microorganisms. Such modulation may be due to increased intracellular levels of high-energy molecules needed to produce, e.g., ATP, GTP and other molecules utilized to drive energetically unfavorable biochemical reactions in the cell, such as the biosynthesis of a fine chemical. This modulation of fine chemical production may also be due to the fact that the breakdown products of many sugars serve as intermediates or precursors for other biosynthetic pathways, including those of certain fine chemicals. Further, PTS proteins are known to participate in certain intracellular signal transduction pathways which may have regulatory activity for one or more fine chemical metabolic pathways; by manipulating these PTS proteins, one may thereby activate a fine chemical biosynthetic pathways or repress a fine chemical degradation pathway. Aspects of the invention are further explicated below.

I. Fine Chemicals

The term 'fine chemical' is art-recognized and includes molecules produced by an organism which have applications in various industries, such as, but not limited to, the pharmaceutical, agriculture, and cosmetics industries. Such compounds include organic acids, such as tartaric acid, itaconic acid, and diaminopimelic acid, both proteinogenic and non-proteinogenic amino acids, purine and pyrimidine bases, nucleosides, and nucleotides (as described e.g. in Kuninaka, A. (1996) Nucleotides and related compounds, p. 561-612, in Biotechnology vol. 6, Rehm et al., eds. VCH: Weinheim, and references contained therein), lipids, both saturated and unsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, "Vitamins", p. 443-613 (1996) VCH: Weinheim and references therein; and Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press, (1995)), enzymes, polyketides (Cane et al. (1998) *Science* 282: 63-68), and all other chemicals described in Gutcho (1983) Chemicals by Fermentation, Noyes Data Corporation, ISBN: 0818805086 and references therein. The metabolism and uses of certain of these fine chemicals are further explicated below.

A. Amino Acid Metabolism and Uses

Amino acids comprise the basic structural units of all proteins, and as such are essential for normal cellular functioning in all organisms. The term "amino acid" is art-recognized. The proteinogenic amino acids, of which there are 20 species, serve as structural units for proteins, in which they are linked by peptide bonds, while the nonproteinogenic amino acids (hundreds of which are known) are not normally found in proteins (see Ulmann's Encyclopedia of Industrial Chemistry, vol. A2, p. 57-97 VCH: Weinheim (1985)). Amino acids may be in the D- or L-optical configuration, though L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, $3^{rd}$ edition, pages 578-590 (1988)). The 'essential' amino acids (histidine, isoleucine, leucine, lysine, methionine, phenylalanine, threonine, tryptophan, and valine), so named because they are generally a nutritional requirement due to the complexity of their biosyntheses, are readily converted by simple biosynthetic pathways to the remaining 11 'nonessential' amino acids (alanine, arginine, asparagine, aspartate, cysteine, glutamate, glutamine, glycine, proline, serine, and tyrosine). Higher animals do retain the ability to synthesize some of these amino acids, but the essential amino acids must be supplied from the diet in order for normal protein synthesis to occur.

Aside from their function in protein biosynthesis, these amino acids are interesting chemicals in their own right, and many have been found to have various applications in the food, feed, chemical, cosmetics, agriculture, and pharmaceutical industries. Lysine is an important amino acid in the nutrition not only of humans, but also of monogastric animals such as poultry and swine. Glutamate is most commonly used as a flavor additive (mono-sodium glutamate, MSG) and is widely used throughout the food industry, as are aspartate, phenylalanine, glycine, and cysteine. Glycine, L-methionine and tryptophan are all utilized in the pharmaceutical industry. Glutamine, valine, leucine, isoleucine, histidine, arginine, pro line, serine and alanine are of use in both the pharmaceutical and cosmetics industries. Threonine, tryptophan, and D/L-methionine are common feed additives. (Leuchtenberger, W. (1996) Amino aids—technical production and use, p. 466-502 in Rehm et al. (eds.) Biotechnology vol. 6, chapter 14a, VCH: Weinheim). Additionally, these amino acids have been found to be useful as precursors for the synthesis of synthetic amino acids and proteins, such as N-acetylcysteine, S-carboxymethyl-L-cysteine, (S)-5-hydroxytryptophan, and others described in Ulmann's Encyclopedia of Industrial Chemistry, vol. A2, p. 57-97, VCH: Weinheim, 1985.

The biosynthesis of these natural amino acids in organisms capable of producing them, such as bacteria, has been well characterized (for review of bacterial amino acid biosynthesis and regulation thereof, see Umbarger, H. E.(1978) *Ann. Rev. Biochem.* 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain β-carbon atom to tetrahydrofolate, in a reaction catalyzed by serine transhydroxymethylase. Phenylalanine, and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine. A complex 9-step pathway results in the production of histidine from 5-phosphoribosyl-1-pyrophosphate, an activated sugar.

Amino acids in excess of the protein synthesis needs of the cell cannot be stored, and are instead degraded to provide intermediates for the major metabolic pathways of the cell (for review see Stryer, L. Biochemistry $3^{rd}$ ed. Ch. 21 "Amino Acid Degradation and the Urea Cycle" p. 495-516 (1988)). Although the cell is able to convert unwanted amino acids into useful metabolic intermediates, amino acid production is costly in terms of energy, precursor molecules, and the enzymes necessary to synthesize them. Thus it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L. Biochemistry, $3^{rd}$ ed. Ch. 24: "Biosynthesis of Amino Acids and Heme" p. 575-600 (1988)). Thus, the output of any particular amino acid is limited by the amount of that amino acid present in the cell.

B. Vitamin, Cofactor, and Nutraceutical Metabolism and Uses

Vitamins, cofactors, and nutraceuticals comprise another group of molecules which the higher animals have lost the ability to synthesize and so must ingest, although they are readily synthesized by other organisms, such as bacteria. These molecules are either bioactive substances themselves, or are precursors of biologically active substances which may serve as electron carriers or intermediates in a variety of metabolic pathways. Aside from their nutritive value, these compounds also have significant industrial value as coloring agents, antioxidants, and catalysts or other processing aids. (For an overview of the structure, activity, and industrial applications of these compounds, see, for example, Ullman's Encyclopedia of Industrial Chemistry, "Vitamins" vol. A27, p. 443-613, VCH: Weinheim, 1996.) The term "vitamin" is art-recognized, and includes nutrients which are required by an organism for normal functioning, but which that organism cannot synthesize by itself. The group of vitamins may encompass cofactors and nutraceutical compounds. The language "cofactor" includes nonproteinaceous compounds required for a normal enzymatic activity to occur. Such compounds may be organic or inorganic; the cofactor molecules of the invention are preferably organic. The term "nutraceutical" includes dietary supplements having health benefits in plants and animals, particularly humans. Examples of such molecules are vitamins, antioxidants, and also certain lipids (e.g., polyunsaturated fatty acids).

The biosynthesis of these molecules in organisms capable of producing them, such as bacteria, has been largely characterized (Ullman's Encyclopedia of Industrial Chemistry, "Vitamins" vol. A27, p. 443-613, VCH: Weinheim, 1996; Michal, G. (1999) Biochemical Pathways: An Atlas of Biochemistry and Molecular Biology, John Wiley & Sons; Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press: Champaign, IL X, 374 S).

Thiamin (vitamin $B_1$) is produced by the chemical coupling of pyrimidine and thiazole moieties. Riboflavin (vitamin $B_2$) is synthesized from guanosine-5'-triphosphate (GTP) and ribose-5'-phosphate. Riboflavin, in turn, is utilized for the synthesis of flavin mononucleotide (FMN) and flavin adenine dinucleotide (FAD). The family of compounds collectively termed 'vitamin $B_6$' (e.g., pyridoxine, pyridoxamine, pyridoxa-5'-phosphate, and the commercially used pyridoxin hydrochloride) are all derivatives of the common structural unit, 5-hydroxy-6-methylpyridine. Pantothenate (pantothenic acid, (R)-(+)-N-(2,4-dihydroxy-3,3-dimethyl-1-oxobutyl)-β-alanine) can be produced either by chemical synthesis or by fermentation. The final steps in pantothenate biosynthesis consist of the ATP-driven condensation of β-alanine and pantoic acid. The enzymes responsible for the biosynthesis steps for the conversion to pantoic acid, to β-alanine and for the condensation to panthotenic acid are known. The metabolically active form of pantothenate is Coenzyme A, for which the biosynthesis proceeds in 5 enzymatic steps. Pantothenate, pyridoxal-5'-phosphate, cysteine and ATP are the precursors of Coenzyme A. These enzymes not only catalyze the formation of panthothante, but also the production of (R)-pantoic acid, (R)-pantolacton, (R)-panthenol (provitamin $B_5$), pantetheine (and its derivatives) and coenzyme A.

Biotin biosynthesis from the precursor molecule pimeloyl-CoA in microorganisms has been studied in detail and several of the genes involved have been identified. Many of the corresponding proteins have been found to also be involved in Fe-cluster synthesis and are members of the nifS class of proteins. Lipoic acid is derived from octanoic acid, and serves as a coenzyme in energy metabolism, where it becomes part of the pyruvate dehydrogenase complex and the α-ketoglutarate dehydrogenase complex. The folates are a group of substances which are all derivatives of folic acid, which is turn is derived from L-glutamic acid, p-amino-benzoic acid and 6-methylpterin. The biosynthesis of folic acid and its derivatives, starting from the metabolism intermediates guanosine-5'-triphosphate (GTP), L-glutamic acid and p-aminobenzoic acid has been studied in detail in certain microorganisms.

Corrinoids (such as the cobalamines and particularly vitamin $B_{12}$) and porphyrines belong to a group of chemicals characterized by a tetrapyrole ring system. The biosynthesis of vitamin $B_{12}$ is sufficiently complex that it has not yet been completely characterized, but many of the enzymes and substrates involved are now known. Nicotinic acid (nicotinate), and nicotinamide are pyridine derivatives which are also termed 'niacin'. Niacin is the precursor of the important coenzymes AND (nicotinamide adenine dinucleotide) and NADP (nicotinamide adenine dinucleotide phosphate) and their reduced forms.

The large-scale production of these compounds has largely relied on cell-free chemical syntheses, though some of these chemicals have also been produced by large-scale culture of microorganisms, such as riboflavin, Vitamin $B_6$, pantothenate, and biotin. Only Vitamin $B_{12}$ is produced solely by fermentation, due to the complexity of its synthesis. In vitro methodologies require significant inputs of materials and time, often at great cost.

C. Purine, Pyrimidine, Nucleoside and Nucleotide Metabolism and Uses

Purine and pyrimidine metabolism genes and their corresponding proteins are important targets for the therapy of tumor diseases and viral infections. The language "purine" or "pyrimidine" includes the nitrogenous bases which are constituents of nucleic acids, co-enzymes, and nucleotides. The term "nucleotide" includes the basic structural units of nucleic acid molecules, which are comprised of a nitrogenous base, a pentose sugar (in the case of RNA, the sugar is ribose; in the case of DNA, the sugar is D-deoxyribose), and phosphoric acid. The language "nucleoside" includes molecules which serve as precursors to nucleotides, but which are lacking the phosphoric acid moiety that nucleotides possess. By inhibiting the biosynthesis of these molecules, or their mobilization to form nucleic acid molecules, it is possible to inhibit RNA and DNA synthesis; by inhibiting this activity in a fashion targeted to cancerous cells, the ability of tumor cells to divide and replicate may be inhibited. Additionally, there are nucleotides which do not form nucleic acid molecules, but rather serve as energy stores (i.e., AMP) or as coenzymes (i.e., FAD and AND).

Several publications have described the use of these chemicals for these medical indications, by influencing purine and/or pyrimidine metabolism (e.g. Christopherson, R. I. and Lyons, S. D. (1990) "Potent inhibitors of de novo pyrimidine and purine biosynthesis as chemotherapeutic agents." *Med. Res. Reviews* 10: 505-548). Studies of enzymes involved in purine and pyrimidine metabolism have been focused on the development of new drugs which can be used, for example, as immunosuppressants or anti-proliferants (Smith, J. L., (1995) "Enzymes in nucleotide synthesis." *Curr. Opin. Struct. Biol.* 5: 752-757; (1995) *Biochem Soc. Transact.* 23: 877-902). However, purine and pyrimidine bases, nucleosides and nucleotides have other utilities: as intermediates in the biosynthesis of several fine chemicals (e.g., thiamine, S-adenosyl-methionine, folates, or riboflavin), as energy carriers for the cell (e.g., ATP or GTP), and for chemicals themselves, commonly used as flavor enhancers (e.g., IMP or GMP) or for several medicinal applications (see, for example, Kuninaka, A. (1996) Nucleotides and Related Compounds in Biotechnology vol. 6, Rehm et al., eds. VCH: Weinheim, p. 561-612). Also, enzymes involved in purine, pyrimidine, nucleoside, or nucleotide metabolism are increasingly serving as targets against which chemicals for crop protection, including fungicides, herbicides and insecticides, are developed.

The metabolism of these compounds in bacteria has been characterized (for reviews see, for example, Zalkin, H. and Dixon, J. E. (1992) "de novo purine nucleotide biosynthesis", in: Progress in Nucleic Acid Research and Molecular Biology, vol. 42, Academic Press:, p. 259-287; and Michal, G. (1999) "Nucleotides and Nucleosides", Chapter 8 in: Biochemical Pathways: An Atlas of Biochemistry and Molecular Biology, Wiley: New York). Purine metabolism has been the subject of intensive research, and is essential to the normal functioning of the cell. Impaired purine metabolism in higher animals can cause severe disease, such as gout. Purine nucleotides are synthesized from ribose-5-phosphate, in a series of steps through the intermediate compound inosine-5'-phosphate (IMP), resulting in the production of guanosine-5'-monophosphate (GMP) or adenosine-5'-monophosphate (AMP), from which the triphosphate forms utilized as nucleotides are readily formed. These compounds are also utilized as energy stores, so their degradation provides energy for many different biochemical processes in the cell. Pyrimidine biosynthesis proceeds by the formation of uridine-5'-monophosphate (UMP) from ribose-5-phosphate. UMP, in turn, is converted to cytidine-5'-triphosphate (CTP). The deoxy-forms of all of these nucleotides are produced in a one step reduction reaction from the diphosphate ribose form of the nucleotide to the diphosphate deoxyribose form of the nucleotide. Upon phosphorylation, these molecules are able to participate in DNA synthesis.

D. Trehalose Metabolism and Uses

Trehalose consists of two glucose molecules, bound in α,α-1,1 linkage. It is commonly used in the food industry as a sweetener, an additive for dried or frozen foods, and in beverages. However, it also has applications in the pharmaceutical, cosmetics and biotechnology industries (see, for example, Nishimoto et al., (1998) U.S. Pat. No. 5,759,610; Singer, M. A. and Lindquist, S. (1998) *Trends Biotech.* 16: 460-467; Paiva, C. L. A. and Panek, A. D. (1996) *Biotech. Ann. Rev.* 2: 293-314; and Shiosaka, M. (1997) J. Japan 172: 97-102). Trehalose is produced by enzymes from many microorganisms and is naturally released into the surrounding medium, from which it can be collected using methods known in the art.

II. The Phosphoenolpyruvate:Sugar Phosphotransferase System

The ability of cells to grow and divide rapidly in culture is to a great degree dependent on the extent to which the cells are able to take up and utilize high energy molecules, such as glucose and other sugars. Different transporter proteins exist to transport different carbon sources into the cell. There are transport proteins for sugars, such as glucose, fructose, mannose, galactose, ribose, sorbose, ribulose, lactose, maltose, sucrose, or raffinose, and also transport proteins for starch or cellulose degradation products. Other transport systems serve to import alcohols (e.g., methanol or ethanol), alkanes, fatty acids and organic acids like acetic acid or lactic acid. In bacteria, sugars may be transported into the cell across the cellular membrane by a variety of mechanisms. Aside from the symport of sugars with protons, one of the most commonly utilized processes for sugar uptake is the bacterial phosphoenolpyruvate: sugar phosphotransferase system (PTS). This system not only catalyzes the translocation (with concomitant phosphorylation) of sugars and hexitols, but it also regulates cellular metabolism in response to the availability of carbohydrates. Such PTS systems are ubiquitous in bacteria but do not occur in archaebacteria or eukaryotes.

Functionally, the PTS system consists of two cytoplasmic proteins, Enzyme I and HPr, and a variable number of sugar-specific integral and peripheral membrane transport complexes (each termed 'Enzyme II' with a sugar-specific subscript, e.g., 'Enzyme II$^{Glu}$' for the Enzyme II complex which binds glucose). Enzymes II specific for mono-, di-, or oligosaccharides, like glucose, fructose, mannose, galactose, ribose, sorbose, ribulose, lactose, maltose, sucrose, raffinose, and others are known. Enzyme I transfers phosphoryl groups from phosphoenolpyruvate (PEP) to the phosphoryl carrier protein, HPr. HPr then transfers the phosphoryl groups to the different Enzyme II transport complexes. While the amino acid sequences of Enzyme I and HPr are quite similar in all bacteria, the sequences for PTS transporters can be grouped into structurally unrelated families. Further, the number and homology between these genes vary from bacteria to bacteria. The *E. coli* genome encodes 38 different PTS proteins, 33 of which are subunits belonging to 22 different transporters. The *M. genitalium* genome contains one gene each for Enzyme I and HPr, and only two genes for PTS transporters. The genomes of *T. palladium* and *C. trachomatis* contain genes for Enzyme I- and HPr-like proteins but no PTS transporters.

All PTS transporters consist of three functional units, IIA, IIB, and IIC, which occur either as protein subunits in a complex (e.g., IIA$^{Glc}$IICB$^{Glc}$) or as domains of a single polypeptide chain (e.g., IICBA$^{GlcNAc}$). IIA and IIB sequentially transfer phosphoryl groups from HPr to the transported sugars. IIC contains the sugar binding site, and spans the inner membrane six or eight times. Sugar translocation is coupled to the transient phosphorylation of the IIB domain. Enzyme I, HPr, and IIA are phosphorylated at histidine residues, while IIB subunits are phosphorylated at either cysteine or histidine residues, depending on the particular transporter involved. Phosphorylation of the sugar being imported has the advantage of blocking the diffusion of the sugar back through the cellular membrane to the extracellular medium, since the charged phosphate group cannot readily traverse the hydrophobic core of the membrane.

Some PTS proteins play a role in intracellular signal transduction in addition to their function in the active transport of sugars. These subunits regulate their targets either allosterically, or by phosphorylation. Their regulatory activity varies with the degree of their phosphorylation (i.e., the ratio of the non-phosphorylated to the phosphorylated form), which in turn varies with the ratio of sugar-dependent dephosphorylation and phosphoenolpyruvate-dependent rephosphorylation. Examples of such intracellular regulation by PTS proteins in *E. coli* include the inhibition of glycerol kinase by dephosphorylated IIA$^{Glc}$, and the activation of adenylate cyclase by the phosphorylated version of this protein. Also, the HPr and the IIB domains of some transporters in these microorganisms regulate gene expression by reversible phosphorylation of transcription antiterminators. In gram-positive bacteria, the activity of HPr is modulated by HPr-specific serine kinases and phosphatases. For example, HPr phosphorylated at serine-46 functions as a co-repressor of the transcriptional repressor CcpA. Lastly, it has been found that unphosphorylated Enzyme I inhibits the sensor kinase CheA of the bacterial chemotaxis machinery, providing a direct link between the sugar binding and transport systems of the bacterium and those systems governing movement of the bacterium (Sonenshein, A. L., et al., eds. *Bacillus subtilis* and other gram-positive bacteria. ASM: Washington, D.C.; Neidhardt, F. C., et al., eds. (1996) *Escherichia coli* and *Salmonella*. ASM Press: Washington, D.C.; Lengeler et al., (1999). Biology of Prokaryotes. Section II, pp. 68-87, Thieme Verlag: Stuttgart).

III. Elements and Methods of the Invention

The present invention is based, at least in part, on the discovery of novel molecules, referred to herein as PTS nucleic acid and protein molecules, which participate in the uptake of high-energy carbon molecules (e.g., glucose, sucrose, and fructose) into *C. glutamicum*, and may also participate in one or more intracellular signal transduction pathways in these microorganisms. In one embodiment, the PTS molecules function to import high-energy carbon molecules into the cell, where the energy produced by their degradation may be utilized to power less energetically favorable biochemical reactions, and their degradation products may serve as intermediates and precursors for a number of other metabolic pathways. In another embodiment, the PTS molecules may participate in one or more intracellular signal transduction pathways, wherein the presence of a modified form of a PTS molecule (e.g., a phosphorylated PTS protein) may participate in a signal transduction cascade which regulates one or more cellular processes. In a preferred embodiment, the activity of the PTS molecules of the present invention has an impact on the production of a desired fine chemical by this organism. In a particularly preferred embodiment, the PTS molecules of the invention are modulated in activity, such that the yield, production or efficiency of production of one or more fine chemicals from *C. glutamicum* is also modulated.

The language, "PTS protein" or "PTS polypeptide" includes proteins which participate in the uptake of one or more high-energy carbon compounds (e.g., mono-, di, or oligosaccharides, such as fructose, mannose, sucrose, glucose, raffinose, galactose, ribose, lactose, maltose, and ribulose) from the extracellular medium to the interior of the cell. Such PTS proteins may also participate in one or more intracellular signal transduction pathways, such as, but not limited to, those governing the uptake of different sugars into the cell. Examples of PTS proteins include those encoded by the PTS genes set forth in Table 1 and Appendix A. For general references pertaining to the PTS system, see: Stryer, L. (1988) Biochemistry. Chapter 37: "Membrane Transport", W. H. Freeman: New York, p. 959-961; Darnell, J. et al. (1990) Molecular Cell Biology Scientific American Books: New York, p. 552-553, and Michal, G., ed. (1999) Biochemical Pathways: An Atlas of Biochemistry and Molecular Biology, Chapter 15 "Special Bacterial Metabolism". The terms "PTS gene" or "PTS nucleic acid sequence" include nucleic acid sequences encoding a PTS protein, which consist of a coding region and also corresponding untranslated 5' and 3' sequence regions. Examples of PTS genes include those set forth in Table 1. The terms "production" or "productivity" are art-recognized and include the concentration of the fermentation product (for example, the desired fine chemical) formed within a given time and a given fermentation volume (e.g., kg product per hour per liter). The term "efficiency of production" includes the time required for a particular level of production to be achieved (for example, how long it takes for the cell to attain a particular rate of output of a fine chemical). The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The terms "degradation" or a "degradation pathway" are art-recognized and include the breakdown of a compound, preferably an organic compound, by a cell to degradation products (generally speaking, smaller or less complex molecules) in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise be unable to pass.

In another embodiment, the PTS molecules of the invention are capable of modulating the production of a desired molecule, such as a fine chemical, in a microorganism such as *C. glutamicum*. Using recombinant genetic techniques, one or more of the PTS proteins of the invention may be manipulated such that its function is modulated. For example, a protein involved in the PTS-mediated import of glucose may be altered such that it is optimized in activity, and the PTS system for the importation of glucose may thus be able to translocate increased amounts of glucose into the cell. Since glucose molecules are utilized not only for energy to drive energetically unfavorable biochemical reactions, such as fine chemical biosyntheses, but also as precursors and intermediates in a number of fine chemical biosynthetic pathways (e.g., serine is synthesized from 3-phosphoglycerate). In each case, the overall yield or rate of production of one of these desired fine chemicals may be increased, either by increasing the energy available for such production to occur, or by increasing the availability of compounds necessary for such production to take place.

Further, many PTS proteins are known to play key roles in intracellular signal transduction pathways which regulate cellular metabolism and sugar uptake in keeping with the availability of carbon sources. For example, it is known that an increased intracellular level of fructose 1,6-bisphosphate (a compound produced during glycolysis) results in the phosphorylation of a serine residue on HPr which prevents this protein from serving as a phosphoryl donor in any PTS sugar transport process, thereby blocking further sugar uptake. By mutagenizing HPr such that this serine residue cannot be phosphorylated, one may constitutively activate HPr and thereby increase sugar transport into the cell, which in turn will ensure greater intracellular energy stores and intermediate/precursor molecules for the biosynthesis of one or more desired fine chemicals.

The isolated nucleic acid sequences of the invention are contained within the genome of a *Corynebacterium glutamicum* strain available through the American Type Culture Collection, given designation ATCC 13032. The nucleotide sequence of the isolated *C. glutamicum* PTS DNAs and the predicted amino acid sequences of the *C. glutamicum* PTS proteins are shown in Appendices A and B, respectively. Computational analyses were performed which classified and/or identified these nucleotide sequences as sequences which encode metabolic pathway proteins.

The present invention also pertains to proteins which have an amino acid sequence which is substantially homologous to an amino acid sequence of Appendix B. As used herein, a protein which has an amino acid sequence which is substantially homologous to a selected amino acid sequence is least about 50% homologous to the selected amino acid sequence, e.g., the entire selected amino acid sequence. A protein which has an amino acid sequence which is substantially homologous to a selected amino acid sequence can also be least about 50-60%, preferably at least about 60-70%, and more preferably at least about 70-80%, 80-90%, or 90-95%, and most preferably at least about 96%, 97%, 98%, 99% or more homologous to the selected amino acid sequence.

The PTS protein or a biologically active portion or fragment thereof of the invention can participate in the transport of high-energy carbon-containing molecules such as glucose into *C. glutamicum*, or can participate in intracellular signal transduction in this microorganism, or may have one or more of the activities set forth in Table 1.

Various aspects of the invention are described in further detail in the following subsections:

A. Isolated Nucleic Acid Molecules

One aspect of the invention pertains to isolated nucleic acid molecules that encode PTS polypeptides or biologically active portions thereof, as well as nucleic acid fragments sufficient for use as hybridization probes or primers for the identification or amplification of PTS-encoding nucleic acid (e.g., PTS DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 100 nucleotides of sequence upstream from the 5' end of the coding region and at least about 20 nucleotides of sequence downstream from the 3' end of the coding region of the gene. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PTS nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g, a *C. glutamicum* cell). Moreover, an "isolated" nucleic acid molecule, such as a DNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of Appendix A, or a portion thereof, can be isolated using standard molecular biology techniques and the sequence information provided herein. For example, a *C. glutamicum* PTS DNA can be isolated from a *C. glutamicum* library using all or portion of one of the sequences of Appendix A as a hybridization probe and standard hybridization techniques (e.g., as described in Sambrook, J., Fritsh, E. F., and Maniatis, T. *Molecular Cloning: A Laboratory Manual* 2nd, ed., Cold Spring Harbor Laboratory, Cold Spring Harbor Laboratory Press, Cold Spring Harbor, N.Y., 1989). Moreover, a nucleic acid molecule encompassing all or a portion of one of the sequences of Appendix A can be isolated by the polymerase chain reaction using oligonucleotide primers designed based upon this sequence (e.g., a nucleic acid molecule encompassing all or a portion of one of the sequences of Appendix A can be isolated by the polymerase chain reaction using oligonucleotide primers designed based upon this same sequence of Appendix A). For example, mRNA can be isolated from normal endothelial cells (e.g., by the guanidinium-thiocyanate extraction procedure of Chirgwin et al. (1979) *Biochemistry* 18: 5294-5299) and DNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in Appendix A. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PTS nucleotide sequence can be prepared by standard synthetic techniques, e.g., using an automated DNA synthesizer.

In a preferred embodiment, an isolated nucleic acid molecule of the invention comprises one of the nucleotide sequences shown in Appendix A. The sequences of Appendix A correspond to the *Corynebacterium glutamicum* PTS DNAs of the invention. This DNA comprises sequences encoding PTS proteins (i.e., the "coding region", indicated in each sequence in Appendix A), as well as 5' untranslated sequences and 3' untranslated sequences, also indicated in Appendix A. Alternatively, the nucleic acid molecule can comprise only the coding region of any of the sequences in Appendix A.

For the purposes of this application, it will be understood that each of the sequences set forth in Appendix A has an identifying RXA, RXN, RXS, or RXC number having the designation "RXA", "RXN", "RXS", or "RXC" followed by 5 digits (i.e., RXA01503, RXN01299, RXS00315, or RXC00953). Each of these sequences comprises up to three parts: a 5' upstream region, a coding region, and a downstream region. Each of these three regions is identified by the same RXA, RXN, RXS, or RXC designation to eliminate confusion. The recitation "one of the sequences in Appendix A", then, refers to any of the sequences in Appendix A, which may be distinguished by their differing RXA, RXN, RXS, or RXC designations. The coding region of each of these sequences is translated into a corresponding amino acid sequence, which is set forth in Appendix B. The sequences of Appendix B are identified by the same RXA, RXN, RXS, or RXC designations as Appendix A, such that they can be readily correlated. For example, the amino acid sequences in Appendix B designated RXA01503, RXN01299, RXS00315, and RXC00953 are translations of the coding regions of the nucleotide sequence of nucleic acid molecules RXA01503, RXN01299, RXS00315, and RXC00953, respectively, in Appendix A. Each of the RXA, RXN, RXS, and RXC nucleotide and amino acid sequences of the invention has also been assigned a SEQ ID NO, as indicated in Table 1. For example, as set forth in Table 1, the nucleotide sequence of RXN01299 is SEQ ID NO: 7, and the corresponding amino acid sequence is SEQ ID NO:8.

Several of the genes of the invention are "F-designated genes". An F-designated gene includes those genes set forth in Table 1 which have an 'F' in front of the RXA, RXN, RXS, or RXC designation. For example, SEQ ID NO:3, designated, as indicated on Table 1, as "F RXA00315", is an F-designated gene, as are SEQ ID NOs: 9, 11, and 13 (designated on Table 1 as "F RXA01299", "F RXA01883", and "F RXA01889", respectively).

In one embodiment, the nucleic acid molecules of the present invention are not intended to include C. glutamicum those compiled in Table 2. In the case of the dapD gene, a sequence for this gene was published in Wehrmann, A., et al. (1998) J. Bacteriol. 180(12): 3159-3165. However, the sequence obtained by the inventors of the present application is significantly longer than the published version. It is believed that the published version relied on an incorrect start codon, and thus represents only a fragment of the actual coding region.

In another preferred embodiment, an isolated nucleic acid molecule of the invention comprises a nucleic acid molecule which is a complement of one of the nucleotide sequences shown in Appendix A, or a portion thereof. A nucleic acid molecule which is complementary to one of the nucleotide sequences shown in Appendix A is one which is sufficiently complementary to one of the nucleotide sequences shown in Appendix A such that it can hybridize to one of the nucleotide sequences shown in Appendix A, thereby forming a stable duplex.

In still another preferred embodiment, an isolated nucleic acid molecule of the invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to a nucleotide sequence shown in Appendix A, or a portion thereof. Ranges and identity values intermediate to the above-recited ranges, (e.g., 70-90% identical or 80-95% identical) are also intended to be encompassed by the present invention. For example, ranges of identity values using a combination of any of the above values recited as upper and/or lower limits are intended to be included. In an additional preferred embodiment, an isolated nucleic acid molecule of the invention comprises a nucleotide sequence which hybridizes, e.g., hybridizes under stringent conditions, to one of the nucleotide sequences shown in Appendix A, or a portion thereof.

Moreover, the nucleic acid molecule of the invention can comprise only a portion of the coding region of one of the sequences in Appendix A, for example a fragment which can be used as a probe or primer or a fragment encoding a biologically active portion of a PTS protein. The nucleotide sequences determined from the cloning of the PTS genes from C. glutamicum allows for the generation of probes and primers designed for use in identifying and/or cloning PTS homologues in other cell types and organisms, as well as PTS homologues from other Corynebacteria or related species. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in Appendix A, an anti-sense sequence of one of the sequences set forth in Appendix A, or naturally occurring mutants thereof. Primers based on a nucleotide sequence of Appendix A can be used in PCR reactions to clone PTS homologues. Probes based on the PTS nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells which misexpress a PTS protein, such as by measuring a level of a PTS-encoding nucleic acid in a sample of cells e.g., detecting PTS mRNA levels or determining whether a genomic PTS gene has been mutated or deleted.

In one embodiment, the nucleic acid molecule of the invention encodes a protein or portion thereof which includes an amino acid sequence which is sufficiently homologous to an amino acid sequence of Appendix B such that the protein or portion thereof maintains the ability to participate in the transport of high-energy carbon molecules (such as glucose) into C. glutamicum, and may also participate in one or more intracellular signal transduction pathways. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of Appendix B) amino acid residues to an amino acid sequence of Appendix B such that the protein or portion thereof is capable of transporting high-energy carbon-containing molecules such as glucose into C. glutamicum, and may also participate in intracellular signal transduction in this microorganism. Protein members of such metabolic pathways, as described herein, function to transport high-energy carbon-containing molecules such as glucose into C. glutamicum, and may also participate in intracellular signal transduction in this microorganism. Examples of such activities are also described herein. Thus, "the function of a PTS protein" contributes to the overall functioning and/or regulation of one or more phosphoenolpyruvate-based sugar transport pathway, and/or contributes, either directly or indirectly, to the yield, production, and/or efficiency of production of one or more fine chemicals. Examples of PTS protein activities are set forth in Table 1.

In another embodiment, the protein is at least about 50-60%, preferably at least about 60-70%, and more preferably at least about 70-80%, 80-90%, 90-95%, and most preferably at least about 96%, 97%, 98%, 99% or more homologous to an entire amino acid sequence of Appendix B.

Portions of proteins encoded by the PTS nucleic acid molecules of the invention are preferably biologically active portions of one of the PTS proteins. As used herein, the term "biologically active portion of a PTS protein" is intended to include a portion, e.g., a domain/motif, of a PTS protein that is capable of transporting high-energy carbon-containing molecules such as glucose into C. glutamicum, or of participating in intracellular signal transduction in this microorganism, or has an activity as set forth in Table 1. To determine whether a PTS protein or a biologically active portion thereof can participate in the transportation of high-energy carbon-containing molecules such as glucose into C. glutamicum, or can participate in intracellular signal transduction in this microorganism, an assay of enzymatic activity may be performed. Such assay methods are well known to those of ordinary skill in the art, as detailed in Example 8 of the Exemplification.

Additional nucleic acid fragments encoding biologically active portions of a PTS protein can be prepared by isolating a portion of one of the sequences in Appendix B, expressing the encoded portion of the PTS protein or peptide (e.g., by recombinant expression in vitro) and assessing the activity of the encoded portion of the PTS protein or peptide.

The invention further encompasses nucleic acid molecules that differ from one of the nucleotide sequences shown in Appendix A (and portions thereof) due to degeneracy of the genetic code and thus encode the same PTS protein as that encoded by the nucleotide sequences shown in Appendix A. In another embodiment, an isolated nucleic acid molecule of the invention has a nucleotide sequence encoding a protein having an amino acid sequence shown in Appendix B. In a still further embodiment, the nucleic acid molecule of the invention encodes a full length *C. glutamicum* protein which is substantially homologous to an amino acid sequence of Appendix B (encoded by an open reading frame shown in Appendix A).

It will be understood by one of ordinary skill in the art that in one embodiment the sequences of the invention are not meant to include the sequences of the prior art, such as those Genbank sequences set forth in Tables 2 or 4 which were available prior to the present invention. In one embodiment, the invention includes nucleotide and amino acid sequences having a percent identity to a nucleotide or amino acid sequence of the invention which is greater than that of a sequence of the prior art (e.g., a Genbank sequence (or the protein encoded by such a sequence) set forth in Tables 2 or 4). For example, the invention includes a nucleotide sequence which is greater than and/or at least 44% identical to the nucleotide sequence designated RXA01503 (SEQ ID NO:5), a nucleotide sequence which is greater than and/or at least 41% identical to the nucleotide sequence designated RXA00951 (SEQ ID NO:15), and a nucleotide sequence which is greater than and/or at least 38% identical to the nucleotide sequence designated RXA01300 (SEQ ID NO:21). One of ordinary skill in the art would be able to calculate the lower threshold of percent identity for any given sequence of the invention by examining the GAP-calculated percent identity scores set forth in Table 4 for each of the three top hits for the given sequence, and by subtracting the highest GAP-calculated percent identity from 100 percent. One of ordinary skill in the art will also appreciate that nucleic acid and amino acid sequences having percent identities greater than the lower threshold so calculated (e.g., at least 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical) are also encompassed by the invention.

In addition to the *C. glutamicum* PTS nucleotide sequences shown in Appendix A, it will be appreciated by those of ordinary skill in the art that DNA sequence polymorphisms that lead to changes in the amino acid sequences of PTS proteins may exist within a population (e.g., the *C. glutamicum* population). Such genetic polymorphism in the PTS gene may exist among individuals within a population due to natural variation. As used herein, the terms "gene" and "recombinant gene" refer to nucleic acid molecules comprising an open reading frame encoding a PTS protein, preferably a *C. glutamicum* PTS protein. Such natural variations can typically result in 1-5% variance in the nucleotide sequence of the PTS gene. Any and all such nucleotide variations and resulting amino acid polymorphisms in PTS that are the result of natural variation and that do not alter the functional activity of PTS proteins are intended to be within the scope of the invention.

Nucleic acid molecules corresponding to natural variants and non-*C. glutamicum* homologues of the *C. glutamicum* PTS DNA of the invention can be isolated based on their homology to the *C. glutamicum* PTS nucleic acid disclosed herein using the *C. glutamicum* DNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of Appendix A. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those of ordinary skill in the art and can be found in Ausubel et al., *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of Appendix A corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *C. glutamicum* PTS protein.

In addition to naturally-occurring variants of the PTS sequence that may exist in the population, one of ordinary skill in the art will further appreciate that changes can be introduced by mutation into a nucleotide sequence of Appendix A, thereby leading to changes in the amino acid sequence of the encoded PTS protein, without altering the functional ability of the PTS protein. For example, nucleotide substitutions leading to amino acid substitutions at "non-essential" amino acid residues can be made in a sequence of Appendix A. A "non-essential" amino acid residue is a residue that can be altered from the wild-type sequence of one of the PTS proteins (Appendix B) without altering the activity of said PTS protein, whereas an "essential" amino acid residue is required for PTS protein activity. Other amino acid residues, however, (e.g., those that are not conserved or only semi-conserved in the domain having PTS activity) may not be essential for activity and thus are likely to be amenable to alteration without altering PTS activity.

Accordingly, another aspect of the invention pertains to nucleic acid molecules encoding PTS proteins that contain changes in amino acid residues that are not essential for PTS activity. Such PTS proteins differ in amino acid sequence from a sequence contained in Appendix B yet retain at least one of the PTS activities described herein. In one embodiment, the isolated nucleic acid molecule comprises a nucleotide sequence encoding a protein, wherein the protein comprises an amino acid sequence at least about 50% homologous to an amino acid sequence of Appendix B and is capable of transporting high-energy carbon-containing molecules such as glucose into *C. glutamicum*, or of participating in intracellular signal transduction in this microorganism, or has one or more activities set forth in Table 1. Preferably, the protein encoded by the nucleic acid molecule is at least about 50-60% homologous to one of the sequences in Appendix B, more preferably at least about 60-70% homologous to one of the sequences in Appendix B, even more preferably at least about 70-80%, 80-90%, 90-95% homologous to one of the sequences in Appendix B, and most preferably at least about 96%, 97%, 98%, or 99% homologous to one of the sequences in Appendix B.

To determine the percent homology of two amino acid sequences (e.g., one of the sequences of Appendix B and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of Appendix B) is occupied by the same amino acid residue or nucleotide as the corresponding position in the other sequence (e.g., a mutant form of the sequence selected from Appendix B), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding a PTS protein homologous to a protein sequence of Appendix B can be created by introducing one or more nucleotide substitutions, additions or deletions into a nucleotide sequence of Appendix A such that one or more amino acid substitutions, additions or deletions are introduced into the encoded protein. Mutations can be introduced into one of the sequences of Appendix A by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PTS protein is preferably replaced with another amino acid residue from the same side chain family. Alternatively, in another embodiment, mutations can be introduced randomly along all or part of a PTS coding sequence, such as by saturation mutagenesis, and the resultant mutants can be screened for a PTS activity described herein to identify mutants that retain PTS activity. Following mutagenesis of one of the sequences of Appendix A, the encoded protein can be expressed recombinantly and the activity of the protein can be determined using, for example, assays described herein (see Example 8 of the Exemplification).

In addition to the nucleic acid molecules encoding PTS proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded DNA molecule or complementary to an mRNA sequence. Accordingly, an antisense nucleic acid can hydrogen bond to a sense nucleic acid. The antisense nucleic acid can be complementary to an entire PTS coding strand, or to only a portion thereof. In one embodiment, an antisense nucleic acid molecule is antisense to a "coding region" of the coding strand of a nucleotide sequence encoding a PTS protein. The term "coding region" refers to the region of the nucleotide sequence comprising codons which are translated into amino acid residues (e.g., the entire coding region of SEQ ID NO. 5 (RXA01503) comprises nucleotides 1 to 249). In another embodiment, the antisense nucleic acid molecule is antisense to a "noncoding region" of the coding strand of a nucleotide sequence encoding PTS. The term "noncoding region" refers to 5' and 3' sequences which flank the coding region that are not translated into amino acids (i.e., also referred to as 5' and 3' untranslated regions).

Given the coding strand sequences encoding PTS disclosed herein (e.g., the sequences set forth in Appendix A), antisense nucleic acids of the invention can be designed according to the rules of Watson and Crick base pairing. The antisense nucleic acid molecule can be complementary to the entire coding region of PTS mRNA, but more preferably is an oligonucleotide which is antisense to only a portion of the coding or noncoding region of PTS mRNA. For example, the antisense oligonucleotide can be complementary to the region surrounding the translation start site of PTS mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PTS protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave PTS mRNA transcripts to thereby inhibit translation of PTS mRNA. A ribozyme having specificity for a PTS-encoding nucleic acid can be designed based upon the nucleotide sequence of a PTS DNA disclosed herein (i.e., SEQ ID NO:5 (RXA01503 in Appendix A)). For example, a derivative of a *Tetrahymena* L-19 IVS RNA can be constructed in which the nucleotide sequence of the active site is complementary to the nucleotide sequence to be cleaved in a PTS-encoding mRNA. See, e.g., Cech et al. U.S. Pat. No. 4,987,071 and Cech et al. U.S. Pat. No. 5,116,742. Alternatively, PTS mRNA can be used to select a catalytic RNA having a specific ribonuclease activity from a pool of RNA molecules. See, e.g., Bartel, D. and Szostak, J. W. (1993) *Science* 261:1411-1418.

Alternatively, PTS gene expression can be inhibited by targeting nucleotide sequences complementary to the regulatory region of a PTS nucleotide sequence (e.g., a PTS promoter and/or enhancers) to form triple helical structures that prevent transcription of a PTS gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

B. Recombinant Expression Vectors and Host Cells

Another aspect of the invention pertains to vectors, preferably expression vectors, containing a nucleic acid encoding a PTS protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-tet-, lpp-, lac-, lpp-lac-, lacI$^q$-, T7-, T5-, T3-, gal-, trc-, ara-, SP6-, arny, SPO2, λ-$P_R$- or λ $P_L$, which are used preferably in bacteria. Additional regulatory sequences are, for example, promoters from yeasts and fungi, such as ADC1, MFα, AC, P-60, CYC1, GAPDH, TEF, rp28, ADH, promoters from plants such as CaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PTS proteins, mutant forms of PTS proteins, fusion proteins, etc.).

The recombinant expression vectors of the invention can be designed for expression of PTS proteins in prokaryotic or eukaryotic cells. For example, PTS genes can be expressed in bacterial cells such as *C. glutamicum*, insect cells (using baculovirus expression vectors), yeast and other fungal cells (see Romanos, M. A. et al. (1992) "Foreign gene expression in yeast: a review", *Yeast* 8: 423-488; van den Hondel, C. A. M. J. J. et al. (1991) "Heterologous gene expression in filamentous fungi" in: More Gene Manipulations in Fungi, J. W. Bennet & L. L. Lasure, eds., p. 396-428: Academic Press: San Diego; and van den Hondel, C. A. M. J. J. & Punt, P. J. (1991)

"Gene transfer systems and vector development for filamentous fungi, in: Applied Molecular Genetics of Fungi, Peberdy, J. F. et al., eds., p. 1-28, Cambridge University Press: Cambridge), algae and multicellular plant cells (see Schmidt, R. and Willmitzer, L. (1988) High efficiency *Agrobacterium tumefactiens*—mediated transformation of *Arabidopsis thaliana* leaf and cotyledon explants" *Plant Cell Rep.*: 583-586), or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PTS protein is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PTS protein unfused to GST can be recovered by cleavage of the fusion protein with thrombin.

Examples of suitable inducible non-fusion *E. coli* expression vectors include pTrc (Amann et al., (1988) *Gene* 69:301-315) pLG338, pACYC184, pBR322, pUC18, pUC19, pKC30, pRep4, pHS1, pHS2, pPLc236, pMBL24, pLG200, pUR290, pIN-III113-B1, λgt11, pBdCl, and pET 11d (Studier et al., *Gene Expression Technology: Methods in Enzymology* 185, Academic Press, San Diego, Calif. (1990) 60-89 ; and Pouwels et al., eds. (1985) Cloning Vectors. Elsevier: New York IBSN 0 444 904018). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming Streptomyces, while plasmids pUB110, pC194, or pBD214 are suited for transformation of *Bacillus* species. Several plasmids of use in the transfer of genetic information into *Corynebacterium* include pHM1519, pBL1, pSA77, or pAJ667 (Pouwels et al., eds. (1985) Cloning Vectors. Elsevier: New York IBSN 0 444 904018).

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) *Nucleic Acids Res.* 20:2111-2118). Such alteration of nucleic acid sequences of the invention can be carried out by standard DNA synthesis techniques.

In another embodiment, the PTS protein expression vector is a yeast expression vector. Examples of vectors for expression in yeast *S. cerivisae* include pYepSec1 (Baldari, et al., (1987) *Embo J.* 6:229-234), 2 µ, pAG-1, Yep6, Yep13, pEMBLYe23, pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge, and Pouwels et al., eds. (1985) Cloning Vectors. Elsevier: New York (IBSN 0 444 904018).

Alternatively, the PTS proteins of the invention can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In another embodiment, the PTS proteins of the invention may be expressed in unicellular plant cells (such as algae) or in plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", *Plant Mol. Biol.* 20: 1195-1197; and Bevan, M. W. (1984) "Binary *Agrobacterium* vectors for plant transformation", *Nucl. Acid. Res.* 12: 8711-8721, and include pLGV23, pGHlac+, pBIN19, pAK2004, and pDH51 (Pouwels et al., eds. (1985) Cloning Vectors. Elsevier: New York IBSN 0 444 904018).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PTS mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PTS protein can be expressed in bacterial cells such as *C. glutamicum*, insect cells, yeast or mammalian cells (such as Chinese hamster ovary cells (CHO) or COS cells). Other suitable host cells are known to one of ordinary skill in the art. Microorganisms related to *Corynebacterium glutamicum* which may be conveniently used as host cells for the nucleic acid and protein molecules of the invention are set forth in Table 3.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PTS protein or can be introduced on a separate vector. Cells stably transfected with the introduced nucleic acid can be identified by drug selection (e.g., cells that have incorporated the selectable marker gene will survive, while the other cells die).

To create a homologous recombinant microorganism, a vector is prepared which contains at least a portion of a PTS gene into which a deletion, addition or substitution has been introduced to thereby alter, e.g., functionally disrupt, the PTS gene. Preferably, this PTS gene is a *Corynebacterium glutamicum* PTS gene, but it can be a homologue from a related bacterium or even from a mammalian, yeast, or insect source. In a preferred embodiment, the vector is designed such that, upon homologous recombination, the endogenous PTS gene is functionally disrupted (i.e., no longer encodes a functional protein; also referred to as a "knock out" vector). Alternatively, the vector can be designed such that, upon homologous recombination, the endogenous PTS gene is mutated or otherwise altered but still encodes functional protein (e.g., the upstream regulatory region can be altered to thereby alter the expression of the endogenous PTS protein). In the homologous recombination vector, the altered portion of the PTS gene is flanked at its 5' and 3' ends by additional nucleic acid of the PTS gene to allow for homologous recombination to occur between the exogenous PTS gene carried by the vector and an endogenous PTS gene in a microorganism. The additional flanking PTS nucleic acid is of sufficient length for successful homologous recombination with the endogenous gene. Typically, several kilobases of flanking DNA (both at the 5' and 3' ends) are included in the vector (see e.g., Thomas, K. R., and Capecchi, M. R. (1987) Cell 51: 503 for a description of homologous recombination vectors). The vector is introduced into a microorganism (e.g., by electroporation) and cells in which the introduced PTS gene has homologously recombined with the endogenous PTS gene are selected, using art-known techniques.

In another embodiment, recombinant microorganisms can be produced which contain selected systems which allow for regulated expression of the introduced gene. For example, inclusion of a PTS gene on a vector placing it under control of the lac operon permits expression of the PTS gene only in the presence of IPTG. Such regulatory systems are well known in the art.

In another embodiment, an endogenous PTS gene in a host cell is disrupted (e.g., by homologous recombination or other genetic means known in the art) such that expression of its protein product does not occur. In another embodiment, an endogenous or introduced PTS gene in a host cell has been altered by one or more point mutations, deletions, or inversions, but still encodes a functional PTS protein. In still another embodiment, one or more of the regulatory regions (e.g., a promoter, repressor, or inducer) of a PTS gene in a microorganism has been altered (e.g., by deletion, truncation, inversion, or point mutation) such that the expression of the PTS gene is modulated. One of ordinary skill in the art will appreciate that host cells containing more than one of the described PTS gene and protein modifications may be readily produced using the methods of the invention, and are meant to be included in the present invention.

A host cell of the invention, such as a prokaryotic or eukaryotic host cell in culture, can be used to produce (i.e., express) a PTS protein. Accordingly, the invention further provides methods for producing PTS proteins using the host cells of the invention. In one embodiment, the method comprises culturing the host cell of invention (into which a recombinant expression vector encoding a PTS protein has been introduced, or into which genome has been introduced a gene encoding a wild-type or altered PTS protein) in a suitable medium until PTS protein is produced. In another embodiment, the method further comprises isolating PTS proteins from the medium or the host cell.

C. Isolated PTS Proteins

Another aspect of the invention pertains to isolated PTS proteins, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of PTS protein in which the protein is separated from cellular components of the cells in which it is naturally or recombinantly produced. In one embodiment, the language "substantially free of cellular material" includes preparations of PTS protein having less than about 30% (by dry weight) of non-PTS protein (also referred to herein as a "contaminating protein"), more preferably less than about 20% of non-PTS protein, still more preferably less than about 10% of non-PTS protein, and most preferably less than about 5% non-PTS protein. When the PTS protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PTS protein in which the protein is separated from chemical precursors or other chemicals which are involved in the synthesis of the protein. In one embodiment, the language "substantially free of chemical precursors or other chemicals" includes preparations of PTS protein having less than about 30% (by dry weight) of chemical precursors or non-PTS chemicals, more preferably less than about 20% chemical precursors or non-PTS chemicals, still more preferably less than about 10% chemical precursors or non-PTS chemicals, and most preferably less than about 5% chemical precursors or non-PTS chemicals. In preferred embodiments, isolated proteins or biologically active portions thereof lack contaminating proteins from the same organism from which the PTS protein is derived. Typically, such proteins are produced by recombinant expression of, for example, a *C. glutamicum* PTS protein in a microorganism such as *C. glutamicum*.

An isolated PTS protein or a portion thereof of the invention can participate in the transport of high-energy carbon-containing molecules such as glucose into *C. glutamicum*, and may also participate in intracellular signal transduction in this microorganism, or has one or more of the activities set forth in Table 1. In preferred embodiments, the protein or portion thereof comprises an amino acid sequence which is sufficiently homologous to an amino acid sequence of Appendix B such that the protein or portion thereof maintains the ability to transport high-energy carbon-containing molecules such as glucose into *C. glutamicum*, or to participate in intracellular signal transduction in this microorganism. The portion of the protein is preferably a biologically active portion as described herein. In another preferred embodiment, a PTS protein of the invention has an amino acid sequence shown in Appendix B. In yet another preferred embodiment, the PTS protein has an amino acid sequence which is encoded by a nucleotide sequence which hybridizes, e.g., hybridizes under stringent conditions, to a nucleotide sequence of Appendix A. In still another preferred embodiment, the PTS protein has an amino acid sequence which is encoded by a nucleotide sequence that is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to one of the nucleic acid sequences of Appendix A, or a portion thereof. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. The preferred PTS proteins of the present invention also preferably possess at least one of the PTS activities described herein. For example, a preferred PTS protein of the present invention includes an amino acid sequence encoded by a nucleotide sequence which hybridizes, e.g., hybridizes under stringent conditions, to a nucleotide sequence of Appendix A, and which can participate in the transport of high-energy carbon-containing molecules such as glucose into *C. glutamicum*, and may also participate in intracellular signal transduction in this microorganism, or which has one or more of the activities set forth in Table 1.

In other embodiments, the PTS protein is substantially homologous to an amino acid sequence of Appendix B and retains the functional activity of the protein of one of the sequences of Appendix B yet differs in amino acid sequence due to natural variation or mutagenesis, as described in detail in subsection I above. Accordingly, in another embodiment, the PTS protein is a protein which comprises an amino acid sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more homologous to an entire amino acid sequence of Appendix B and which has at least one of the PTS activities described herein. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. In another embodiment, the invention pertains to a full length *C.*

*glutamicum* protein which is substantially homologous to an entire amino acid sequence of Appendix B.

Biologically active portions of a PTS protein include peptides comprising amino acid sequences derived from the amino acid sequence of a PTS protein, e.g., the an amino acid sequence shown in Appendix B or the amino acid sequence of a protein homologous to a PTS protein, which include fewer amino acids than a full length PTS protein or the full length protein which is homologous to a PTS protein, and exhibit at least one activity of a PTS protein. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a PTS protein. Moreover, other biologically active portions, in which other regions of the protein are deleted, can be prepared by recombinant techniques and evaluated for one or more of the activities described herein. Preferably, the biologically active portions of a PTS protein include one or more selected domains/motifs or portions thereof having biological activity.

PTS proteins are preferably produced by recombinant DNA techniques. For example, a nucleic acid molecule encoding the protein is cloned into an expression vector (as described above), the expression vector is introduced into a host cell (as described above) and the PTS protein is expressed in the host cell. The PTS protein can then be isolated from the cells by an appropriate purification scheme using standard protein purification techniques. Alternative to recombinant expression, a PTS protein, polypeptide, or peptide can be synthesized chemically using standard peptide synthesis techniques. Moreover, native PTS protein can be isolated from cells (e.g., endothelial cells), for example using an anti-PTS antibody, which can be produced by standard techniques utilizing a PTS protein or fragment thereof of this invention.

The invention also provides PTS chimeric or fusion proteins. As used herein, a PTS "chimeric protein" or "fusion protein" comprises a PTS polypeptide operatively linked to a non-PTS polypeptide. An "PTS polypeptide" refers to a polypeptide having an amino acid sequence corresponding to PTS, whereas a "non-PTS polypeptide" refers to a polypeptide having an amino acid sequence corresponding to a protein which is not substantially homologous to the PTS protein, e.g., a protein which is different from the PTS protein and which is derived from the same or a different organism. Within the fusion protein, the term "operatively linked" is intended to indicate that the PTS polypeptide and the non-PTS polypeptide are fused in-frame to each other. The non-PTS polypeptide can be fused to the N-terminus or C-terminus of the PTS polypeptide. For example, in one embodiment the fusion protein is a GST-PTS fusion protein in which the PTS sequences are fused to the C-terminus of the GST sequences. Such fusion proteins can facilitate the purification of recombinant PTS proteins. In another embodiment, the fusion protein is a PTS protein containing a heterologous signal sequence at its N-terminus. In certain host cells (e.g., mammalian host cells), expression and/or secretion of a PTS protein can be increased through use of a heterologous signal sequence.

Preferably, a PTS chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PTS-encoding nucleic acid can be cloned into such an expression vector such that the fusion moiety is linked in-frame to the PTS protein.

Homologues of the PTS protein can be generated by mutagenesis, e.g., discrete point mutation or truncation of the PTS protein. As used herein, the term "homologue" refers to a variant form of the PTS protein which acts as an agonist or antagonist of the activity of the PTS protein. An agonist of the PTS protein can retain substantially the same, or a subset, of the biological activities of the PTS protein. An antagonist of the PTS protein can inhibit one or more of the activities of the naturally occurring form of the PTS protein, by, for example, competitively binding to a downstream or upstream member of the PTS system which includes the PTS protein. Thus, the *C. glutamicum* PTS protein and homologues thereof of the present invention may modulate the activity of one or more sugar transport pathways or intracellular signal transduction pathways in which PTS proteins play a role in this microorganism.

In an alternative embodiment, homologues of the PTS protein can be identified by screening combinatorial libraries of mutants, e.g., truncation mutants, of the PTS protein for PTS protein agonist or antagonist activity. In one embodiment, a variegated library of PTS variants is generated by combinatorial mutagenesis at the nucleic acid level and is encoded by a variegated gene library. A variegated library of PTS variants can be produced by, for example, enzymatically ligating a mixture of synthetic oligonucleotides into gene sequences such that a degenerate set of potential PTS sequences is expressible as individual polypeptides, or alternatively, as a set of larger fusion proteins (e.g., for phage display) containing the set of PTS sequences therein. There are a variety of methods which can be used to produce libraries of potential PTS homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PTS sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the PTS protein coding can be used to generate a variegated population of PTS fragments for screening and subsequent selection of homologues of a PTS protein. In one embodiment, a library of coding sequence fragments can be generated by treating a double stranded PCR fragment of a PTS coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PTS protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PTS homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PTS homologues (Arkin and Yourvan (1992) *PNAS* 89:7811-7815; Delgrave et al. (1993) *Protein Engineering* 6(3):327-331).

In another embodiment, cell based assays can be exploited to analyze a variegated PTS library, using methods well known in the art.

D. Uses and Methods of the Invention

The nucleic acid molecules, proteins, protein homologues, fusion proteins, primers, vectors, and host cells described herein can be used in one or more of the following methods: identification of *C. glutamicum* and related organisms; mapping of genomes of organisms related to *C. glutamicum*; identification and localization of *C. glutamicum* sequences of interest; evolutionary studies; determination of PTS protein regions required for function; modulation of a PTS protein activity; modulation of the activity of a PTS pathway; and modulation of cellular production of a desired compound, such as a fine chemical.

The PTS nucleic acid molecules of the invention have a variety of uses. First, they may be used to identify an organism as being *Corynebacterium glutamicum* or a close relative thereof. Also, they may be used to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present.

Although *Corynebacterium glutamicum* itself is nonpathogenic, it is related to pathogenic species, such as *Corynebacterium diphtheriae*. *Corynebacterium diphtheriae* is the causative agent of diphtheria, a rapidly developing, acute, febrile infection which involves both local and systemic pathology. In this disease, a local lesion develops in the upper respiratory tract and involves necrotic injury to epithelial cells; the bacilli secrete toxin which is disseminated through this lesion to distal susceptible tissues of the body. Degenerative changes brought about by the inhibition of protein synthesis in these tissues, which include heart, muscle, peripheral nerves, adrenals, kidneys, liver and spleen, result in the systemic pathology of the disease. Diphtheria continues to have high incidence in many parts of the world, including Africa, Asia, Eastern Europe and the independent states of the former Soviet Union. An ongoing epidemic of diphtheria in the latter two regions has resulted in at least 5,000 deaths since 1990.

In one embodiment, the invention provides a method of identifying the presence or activity of *Cornyebacterium diphtheriae* in a subject. This method includes detection of one or more of the nucleic acid or amino acid sequences of the invention (e.g., the sequences set forth in Appendix A or Appendix B) in a subject, thereby detecting the presence or activity of *Corynebacterium diphtheriae* in the subject. *C. glutamicum* and *C. diphtheriae* are related bacteria, and many of the nucleic acid and protein molecules in *C. glutamicum* are homologous to *C. diphtheriae* nucleic acid and protein molecules, and can therefore be used to detect *C. diphtheriae* in a subject.

The nucleic acid and protein molecules of the invention may also serve as markers for specific regions of the genome. This has utility not only in the mapping of the genome, but also for functional studies of *C. glutamicum* proteins. For example, to identify the region of the genome to which a particular *C. glutamicum* DNA-binding protein binds, the *C. glutamicum* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *C. glutamicum*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related bacteria, such as *Brevibacterium lactofermentum*.

The PTS nucleic acid molecules of the invention are also useful for evolutionary and protein structural studies. The sugar uptake system in which the molecules of the invention participate are utilized by a wide variety of bacteria; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the PTS nucleic acid molecules of the invention may result in the production of PTS proteins having functional differences from the wild-type PTS proteins. These proteins may be improved in efficiency or activity, may be present in greater numbers in the cell than is usual, or may be decreased in efficiency or activity.

The invention provides methods for screening molecules which modulate the activity of a PTS protein, either by interacting with the protein itself or a substrate or binding partner of the PTS protein, or by modulating the transcription or translation of a PTS nucleic acid molecule of the invention. In such methods, a microorganism expressing one or more PTS proteins of the invention is contacted with one or more test compounds, and the effect of each test compound on the activity or level of expression of the PTS protein is assessed.

The PTS molecules of the invention may be modified such that the yield, production, and/or efficiency of production of one or more fine chemicals is improved. For example, by modifying a PTS protein involved in the uptake of glucose such that it is optimized in activity, the quantity of glucose uptake or the rate at which glucose is translocated into the cell may be increased. The breakdown of glucose and other sugars within the cell provides energy that may be used to drive energetically unfavorable biochemical reactions, such as those involved in the biosynthesis of fine chemicals. This breakdown also provides intermediate and precursor molecules necessary for the biosynthesis of certain fine chemicals, such as amino acids, vitamins and cofactors. By increasing the amount of intracellular high-energy carbon molecules through modification of the PTS molecules of the invention, one may therefore increase both the energy available to perform metabolic pathways necessary for the production of one or more fine chemicals, and also the intracellular pools of metabolites necessary for such production. Conversely, by decreasing the importation of a sugar whose breakdown products include a compound which is used solely in metabolic pathways which compete with pathways utilized for the production of a desired fine chemical for enzymes, cofactors, or intermediates, one may downregulate this pathway and thus perhaps increase production through the desired biosynthetic pathway.

Further, the PTS molecules of the invention may be involved in one or more intracellular signal transduction pathways which may affect the yields and/or rate of production of one or more fine chemical from *C. glutamicum*. For example, proteins necessary for the import of one or more sugars from the extracellular medium (e.g., HPr, Enzyme I, or a member of an Enzyme II complex) are frequently posttranslationally modified upon the presence of a sufficient quantity of the sugar in the cell, such that they are no longer able to import that sugar. An example of this occurs in *E. coli*, where high intracellular levels of fructose 1,6-bisphosphate result in the phosphorylation of HPr at serine-46, upon which this molecule is no longer able to participate in the transport of any sugar. While this intracellular level of sugar at which the transport system is shut off may be sufficient to sustain the normal functioning of the cell, it may be limiting for the overproduction of the desired fine chemical. Thus, it may be desirable to modify the PTS proteins of the invention such that they are no longer responsive to such negative regulation, thereby permitting greater intracellular concentrations of one or more sugars to be achieved, and, by extension, more efficient production or greater yields of one or more fine chemicals from organisms containing such mutant PTS proteins.

This aforementioned list of mutagenesis strategies for PTS proteins to result in increased yields of a desired compound is not meant to be limiting; variations on these mutagenesis strategies will be readily apparent to one of ordinary skill in the art. By these mechanisms, the nucleic acid and protein molecules of the invention may be utilized to generate *C. glutamicum* or related strains of bacteria expressing mutated PTS nucleic acid and protein molecules such that the yield, production, and/or efficiency of production of a desired compound is improved. This desired compound may be any natural product of *C. glutamicum*, which includes the final products of biosynthesis pathways and intermediates of naturally-occurring metabolic pathways, as well as molecules which do not naturally occur in the metabolism of *C. glutamicum*, but which are produced by a *C. glutamicum* strain of the invention.

This invention is further illustrated by the following examples which should not be construed as limiting. The contents of all references, patent applications, patents, published patent applications, Tables, Appendices, and the sequence listing cited throughout this application are hereby incorporated by reference.

Exemplification

EXAMPLE 1

Preparation of Total Genomic DNA of *Corynebacterium glutamicum* ATCC 13032

A culture of *Corynebacterium glutamicum* (ATCC 13032) was grown overnight at 30° C. with vigorous shaking in BHI medium (Difco). The cells were harvested by centrifugation, the supernatant was discarded and the cells were resuspended in 5 ml buffer-I (5% of the original volume of the culture—all indicated volumes have been calculated for 100 ml of culture volume). Composition of buffer-I: 140.34 g/l sucrose, 2.46 g/l $MgSO_4 \times 7H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4 \times 7H_2O$, 0.2 g/l $CaCl_2$, 0.5 g/l yeast extract (Difco), 10 ml/l trace-elements-mix (200 mg/l $FeSO_4 \times H_2O$, 10 mg/l $ZnSO_4 \times 7 H_2O$, 3 mg/l $MnCl_2 \times 4 H_2O$, 30 mg/l $H_3BO_3$ 20 mg/l $CoCl_2 \times 6 H_2O$, 1 mg/l $NiCl_2 \times 6 H_2O$, 3 mg/l $Na_2MoO_4 \times 2 H_2O$, 500 mg/l complexing agent (EDTA or critic acid), 100 ml/l vitamins-mix (0.2 mg/l biotin, 0.2 mg/l folic acid, 20 mg/l p-amino benzoic acid, 20 mg/l riboflavin, 40 mg/l ca-panthothenate, 140 mg/l nicotinic acid, 40 mg/l pyridoxole hydrochloride, 200 mg/l myo-inositol). Lysozyme was added to the suspension to a final concentration of 2.5 mg/ml. After an approximately 4 h incubation at 37° C., the cell wall was degraded and the resulting protoplasts are harvested by centrifugation. The pellet was washed once with 5 ml buffer-I and once with 5 ml TE-buffer (10 mM Tris-HCl, 1 mM EDTA, pH 8). The pellet was resuspended in 4 ml TE-buffer and 0.5 ml SDS solution (10%) and 0.5 ml NaCl solution (5 M) are added. After adding of proteinase K to a final concentration of 200 µg/ml, the suspension is incubated for ca.18 h at 37° C. The DNA was purified by extraction with phenol, phenol-chloroform-isoamylalcohol and chloroform-isoamylalcohol using standard procedures. Then, the DNA was precipitated by adding 1/50 volume of 3 M sodium acetate and 2 volumes of ethanol, followed by a 30 min incubation at −20° C. and a 30 min centrifugation at 12,000 rpm in a high speed centrifuge using a SS34 rotor (Sorvall). The DNA was dissolved in 1 ml TE-buffer containing 20 µg/ml RNaseA and dialysed at 4° C. against 1000 ml TE-buffer for at least 3 hours. During this time, the buffer was exchanged 3 times. To aliquots of 0.4 ml of the dialysed DNA solution, 0.4 ml of 2 M LiCl and 0.8 ml of ethanol are added. After a 30 min incubation at −20° C., the DNA was collected by centrifugation (13,000 rpm, Biofuge Fresco, Heraeus, Hanau, Germany). The DNA pellet was dissolved in TE-buffer. DNA prepared by this procedure could be used for all purposes, including southern blotting or construction of genomic libraries.

EXAMPLE 2

Construction of Genomic Libraries in *Escherichia coli* of *Corynebacterium glutamicum* ATCC13032

Using DNA prepared as described in Example 1, cosmid and plasmid libraries were constructed according to known and well established methods (see e.g., Sambrook, J. et al. (1989) "Molecular Cloning: A Laboratory Manual", Cold Spring Harbor Laboratory Press, or Ausubel, F. M. et al. (1994) "Current Protocols in Molecular Biology", John Wiley & Sons.)

Any plasmid or cosmid could be used. Of particular use were the plasmids pBR322 (Sutcliffe, J. G. (1979) *Proc. Natl. Acad. Sci. USA*, 75:3737-3741); pACYC177 (Change & Cohen (1978) *J. Bacteriol* 134:1141-1156), plasmids of the pBS series (pBSSK+, pBSSK− and others; Stratagene, LaJolla, USA), or cosmids as SuperCos1 (Stratagene, LaJolla, USA) or Lorist6 (Gibson, T. J., Rosenthal A. and Waterson, R. H. (1987) *Gene* 53:283-286. Gene libraries specifically for use in *C. glutamicum* may be constructed using plasmid pSL109 (Lee, H.-S. and A. J. Sinskey (1994) *J. Microbiol. Biotechnol.* 4: 256-263).

EXAMPLE 3

DNA Sequencing and Computational Functional Analysis

Genomic libraries as described in Example 2 were used for DNA sequencing according to standard methods, in particular by the chain termination method using ABI377 sequencing machines (see e.g., Fleischman, R. D. et al. (1995) "Whole-genome Random Sequencing and Assembly of Haemophilus Influenzae Rd., *Science*, 269:496-512). Sequencing primers with the following nucleotide sequences were used: 5'-GGAAACAGTATGACCATG-3' or 5'-GTAAAAC-GACGGCCAGT-3'.

EXAMPLE 4

In vivo Mutagenesis

In vivo mutagenesis of *Corynebacterium glutamicum* can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington.) Such strains are well known to one of ordinary skill in the art. The use of such strains is illustrated, for example, in Greener, A. and Callahan, M. (1994) *Strategies* 7: 32-34.

EXAMPLE 5

DNA Transfer Between *Escherichia coli* and *Corynebacterium glutamicum*

Several *Corynebacterium* and *Brevibacterium* species contain endogenous plasmids (as e.g., pHM1519 or pBL1) which replicate autonomously (for review see, e.g., Martin, J. F. et al. (1987) *Biotechnology*, 5:137-146). Shuttle vectors for *Escherichia coli* and *Corynebacterium glutamicum* can be readily constructed by using standard vectors for *E. coli* (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons) to which a origin or replication for and a suitable marker from *Corynebacterium glutamicum* is added. Such origins of replication are preferably taken from endogenous plasmids isolated from *Corynebacterium* and *Brevibacterium* species. Of particular use as transformation markers for these species are genes for kanamycin resistance (such as those derived from the Tn5 or Tn903 transposons) or chloramphenicol (Winnacker, E. L. (1987) "From Genes to Clones—Introduction to Gene Technology, VCH, Weinheim). There are numerous examples in the literature of the construction of a wide variety of shuttle vectors which replicate in both *E. coli* and *C. glutamicum*, and which can be used for several purposes, including gene overexpression (for reference, see e.g., Yoshihama, M. et al. (1985) *J. Bacteriol.* 162:591-597, Martin J. F. et al. (1987) *Biotechnology*, 5:137-146 and Eikmanns, B. J. et al. (1991) *Gene*, 102:93-98).

Using standard methods, it is possible to clone a gene of interest into one of the shuttle vectors described above and to introduce such a hybrid vectors into strains of *Corynebacterium glutamicum*. Transformation of *C. glutamicum* can be achieved by protoplast transformation (Kastsumata, R. et al. (1984) *J. Bacteriol.* 159306-311), electroporation (Liebl, E. et al. (1989) *FEMS Microbiol. Letters*, 53:399-303) and in cases where special vectors are used, also by conjugation (as described e.g. in Schäfer, A et al. (1990) *J. Bacteriol.* 172: 1663-1666). It is also possible to transfer the shuttle vectors for *C. glutamicum* to *E. coli* by preparing plasmid DNA from *C. glutamicum* (using standard methods well-known in the art) and transforming it into *E. coli*. This transformation step can be performed using standard methods, but it is advantageous to use an Mcr-deficient *E. coli* strain, such as NM522 (Gough & Murray (1983) *J. Mol. Biol.* 166:1-19).

Genes may be overexpressed in *C. glutamicum* strains using plasmids which comprise pCG1 (U.S. Pat. No. 4,617, 267) or fragments thereof, and optionally the gene for kanamycin resistance from TN903 (Grindley, N. D. and Joyce, C. M. (1980) *Proc. Natl. Acad. Sci. USA* 77(12): 7176-7180). In addition, genes may be overexpressed in *C. glutamicum* strains using plasmid pSL109 (Lee, H.-S. and A. J. Sinskey (1994) *J. Microbiol. Biotechnol.* 4: 256-263).

Aside from the use of replicative plasmids, gene overexpression can also be achieved by integration into the genome. Genomic integration in *C. glutamicum* or other *Corynebacterium* or *Brevibacterium* species may be accomplished by well-known methods, such as homologous recombination with genomic region(s), restriction endonuclease mediated integration (REMI) (see, e.g., DE Patent 19823834), or through the use of transposons. It is also possible to modulate the activity of a gene of interest by modifying the regulatory regions (e.g., a promoter, a repressor, and/or an enhancer) by sequence modification, insertion, or deletion using site-directed methods (such as homologous recombination) or methods based on random events (such as transposon mutagenesis or REMI). Nucleic acid sequences which function as transcriptional terminators may also be inserted 3' to the coding region of one or more genes of the invention; such terminators are well-known in the art and are described, for example, in Winnacker, E. L. (1987) From Genes to Clones— Introduction to Gene Technology. VCH: Weinheim.

EXAMPLE 6

Assessment of the Expression of the Mutant Protein

Observations of the activity of a mutated protein in a transformed host cell rely on the fact that the mutant protein is expressed in a similar fashion and in a similar quantity to that of the wild-type protein. A useful method to ascertain the level of transcription of the mutant gene (an indicator of the amount of mRNA available for translation to the gene product) is to perform a Northern blot (for reference see, for example, Ausubel et al. (1988) Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information is evidence of the degree of transcription of the mutant gene. Total cellular RNA can be prepared from *Corynebacterium glutamicum* by several methods, all well-known in the art, such as that described in Bormann, E. R. et al. (1992) *Mol. Microbiol.* 6: 317-326.

To assess the presence or relative quantity of protein translated from this mRNA, standard techniques, such as a Western blot, may be employed (see, for example, Ausubel et al. (1988) Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label which may be readily detected. The presence and quantity of label observed indicates the presence and quantity of the desired mutant protein present in the cell.

EXAMPLE 7

Growth of Genetically Modified *Corynebacterium glutamicum*—Media and Culture Conditions Genetically modified *Corynebacteria* are cultured in synthetic or natural growth media. A number of different growth media for *Corynebacteria* are both well-known and readily available (Lieb et al. (1989) *Appl. Microbiol. Biotechnol.*, 32:205-210; von der Osten et al. (1998) *Biotechnology Letters*, 11:11 -16; Patent DE 4,120,867; Liebl (1992) "The Genus *Corynebacterium*, in: The Procaryotes, Volume II, Balows, A. et al., eds. Springer-Verlag). These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribulose, lactose, maltose, sucrose, raffinose, starch or cellulose serve as very good carbon sources. It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

Inorganic salt compounds which may be included in the media include the chloride-, phosphorous- or sulfate- salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components are sterilized, either by heat (20 minutes at 1.5 bar and 121° C.) or by sterile filtration. The components can either be sterilized together or, if necessary, separately. All media components can be present at the beginning of growth, or they can optionally be added continuously or batchwise.

Culture conditions are defined separately for each experiment. The temperature should be in a range between 15° C. and 45° C. The temperature can be kept constant or can be altered during the experiment. The pH of the medium should be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an $OD_{600}$ of 0.5-1.5 using cells grown on agar plates, such as CM plates (10 g/l glucose, 2,5 g/l NaCl, 2 g/l urea, 10 g/l polypeptone, 5 g/l yeast extract, 5 g/l meat extract, 22 g/l NaCl, 2 g/l urea, 10 g/l polypeptone, 5 g/l yeast extract, 5 g/l meat extract, 22 g/l agar, pH 6.8 with 2M NaOH) that had been incubated at 30° C. Inoculation of the media is accomplished by either introduction of a saline suspension of *C. glutamicum* cells from CM plates or addition of a liquid preculture of this bacterium.

EXAMPLE 8

In vitro Analysis of the Function of Mutant Proteins

The determination of activities and kinetic parameters of enzymes is well established in the art. Experiments to determine the activity of any given altered enzyme must be tailored to the specific activity of the wild-type enzyme, which is well within the ability of one of ordinary skill in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, "Enzymes". VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as beta-galactosidase, green fluorescent protein, and several others.

The determination of activity of membrane-transport proteins can be performed according to techniques such as those described in Gennis, R. B. (1989) "Pores, Channels and Transporters", in Biomembranes, Molecular Structure and Function, Springer: Heidelberg, p. 85-137; 199-234; and 270-322.

EXAMPLE 9

Analysis of Impact of Mutant Protein on the Production of the Desired Product

The effect of the genetic modification in *C. glutamicum* on production of a desired compound (such as an amino acid) can be assessed by growing the modified microorganism under suitable conditions (such as those described above) and analyzing the medium and/or the cellular component for increased production of the desired product (i.e., an amino acid). Such analysis techniques are well known to one of ordinary skill in the art, and include spectroscopy, thin layer chromatography, staining methods of various kinds, enzymatic and microbiological methods, and analytical chromatography such as high performance liquid chromatography (see, for example, Ullman, Encyclopedia of Industrial Chemistry, vol. A2, p. 89-90 and p. 443-613, VCH: Weinheim (1985); Fallon, A. et al., (1987) "Applications of HPLC in Biochemistry" in: Laboratory Techniques in Biochemistry and Molecular Biology, vol. 17; Rehm et al. (1993) Biotechnology, vol. 3, Chapter III: "Product recovery and purification", page 469-714, VCH: Weinheim; Belter, P. A. et al. (1988) Bioseparations: downstream processing for biotechnology, John Wiley and Sons; Kennedy, J. F. and Cabral, J. M. S. (1992) Recovery processes for biological materials, John Wiley and Sons; Shaeiwitz, J. A. and Henry, J. D. (1988) Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications.)

In addition to the measurement of the final product of fermentation, it is also possible to analyze other components of the metabolic pathways utilized for the production of the desired compound, such as intermediates and side-products, to determine the overall productivity of the organism, yield, and/or efficiency of production of the compound. Analysis methods include measurements of nutrient levels in the medium (e.g., sugars, hydrocarbons, nitrogen sources, phosphate, and other ions), measurements of biomass composition and growth, analysis of the production of common metabolites of biosynthetic pathways, and measurement of gasses produced during fermentation. Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein.

EXAMPLE 10

Purification of the Desired Product from *C. glutamicum* Culture

Recovery of the desired product from the *C. glutamicum* cells or supernatant of the above-described culture can be performed by various methods well known in the art. If the desired product is not secreted from the cells, the cells can be harvested from the culture by low-speed centrifugation, the cells can be lysed by standard techniques, such as mechanical force or sonication. The cellular debris is removed by centrifugation, and the supernatant fraction containing the soluble proteins is retained for further purification of the desired compound. If the product is secreted from the *C. glutamicum* cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One of ordinary skill in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986).

The identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al. (1994) *Appl. Environ. Microbiol.* 60: 133-140; Malakhova et al. (1996)

*Biotekhnologiya* 11: 27-32; and Schmidt et al. (1998) *Bioprocess Engineer.* 19: 67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

EXAMPLE 11

Analysis of the Gene Sequences of the Invention

The comparison of sequences and determination of percent homology between two sequences are art-known techniques, and can be accomplished using a mathematical algorithm, such as the algorithm of Karlin and Altschul (1990) *Proc. Natl. Acad. Sci.* USA 87:2264-68, modified as in Karlin and Altschul (1993) *Proc. Natl. Acad. Sci.* USA 90:5873-77. Such an algorithm is incorporated into the NBLAST and XBLAST programs (version 2.0) of Altschul, et al. (1990) *J. Mol. Biol.* 215:403-10. BLAST nucleotide searches can be performed with the NBLAST program, score =100, wordlength=12 to obtain nucleotide sequences homologous to PTS nucleic acid molecules of the invention. BLAST protein searches can be performed with the XBLAST program, score=50, wordlength=3 to obtain amino acid sequences homologous to PTS protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, one of ordinary skill in the art will know how to optimize the parameters of the program (e.g., XBLAST and NBLAST) for the specific sequence being analyzed.

Another example of a mathematical algorithm utilized for the comparison of sequences is the algorithm of Meyers and Miller ((1988) *Comput. Appl. Biosci.* 4: 11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art, and include ADVANCE and ADAM. described in Torelli and Robotti (1994) *Comput. Appl. Biosci.* 10:3-5; and FASTA, described in Pearson and Lipman (1988) *P.N.A.S.* 85:2444-8.

The percent homology between two amino acid sequences can also be accomplished using the GAP program in the GCG software package (available at http://www.gcg.com), using either a Blosum 62 matrix or a PAM250 matrix, and a gap weight of 12, 10, 8, 6, or 4 and a length weight of 2, 3, or 4. The percent homology between two nucleic acid sequences can be accomplished using the GAP program in the GCG software package, using standard parameters, such as a gap weight of 50 and a length weight of 3.

A comparative analysis of the gene sequences of the invention with those present in Genbank has been performed using techniques known in the art (see, e.g., Bexevanis and Ouellette, eds. (1998) Bioinformatics: A Practical Guide to the Analysis of Genes and Proteins. John Wiley and Sons: New York). The gene sequences of the invention were compared to genes present in Genbank in a three-step process. In a first step, a BLASTN analysis (e.g., a local alignment analysis) was performed for each of the sequences of the invention against the nucleotide sequences present in Genbank, and the top 500 hits were retained for further analysis. A subsequent FASTA search (e.g., a combined local and global alignment analysis, in which limited regions of the sequences are aligned) was performed on these 500 hits. Each gene sequence of the invention was subsequently globally aligned to each of the top three FASTA hits, using the GAP program in the GCG software package (using standard parameters). In order to obtain correct results, the length of the sequences extracted from Genbank were adjusted to the length of the query sequences by methods well-known in the art. The results of this analysis are set forth in Table 4. The resulting data is identical to that which would have been obtained had a GAP (global) analysis alone been performed on each of the genes of the invention in comparison with each of the references in Genbank, but required significantly reduced computational time as compared to such a database-wide GAP (global) analysis. Sequences of the invention for which no alignments above the cutoff values were obtained are indicated on Table 4 by the absence of alignment information. It will further be understood by one of ordinary skill in the art that the GAP alignment homology percentages set forth in Table 4 under the heading "% homology (GAP)" are listed in the European numerical format, wherein a ',' represents a decimal point. For example, a value of "40,345" in this column represents "40.345%".

EXAMPLE 12

Construction and Operation of DNA Microarrays

The sequences of the invention may additionally be used in the construction and application of DNA microarrays (the design, methodology, and uses of DNA arrays are well known in the art, and are described, for example, in Schena, M. et al. (1995) *Science* 270: 467-470; Wodicka, L. et al. (1997) *Nature Biotechnology* 15: 1.359-1367; DeSaizieu, A. et al. (1998) *Nature Biotechnology* 16: 45-48; and DeRisi, J. L. et al. (1997) *Science* 278: 680-686).

DNA microarrays are solid or flexible supports consisting of nitrocellulose, nylon, glass, silicone, or other materials. Nucleic acid molecules may be attached to the surface in an ordered manner. After appropriate labeling, other nucleic acids or nucleic acid mixtures can be hybridized to the immobilized nucleic acid molecules, and the label may be used to monitor and measure the individual signal intensities of the hybridized molecules at defined regions. This methodology allows the simultaneous quantification of the relative or absolute amount of all or selected nucleic acids in the applied nucleic acid sample or mixture. DNA microarrays, therefore, permit an analysis of the expression of multiple (as many as 6800 or more) nucleic acids in parallel (see, e.g., Schena, M. (1996) *BioEssays* 18(5): 427-431).

The sequences of the invention may be used to design oligonucleotide primers which are able to amplify defined regions of one or more *C. glutamicum* genes by a nucleic acid amplification reaction such as the polymerase chain reaction. The choice and design of the 5' or 3' oligonucleotide primers or of appropriate linkers allows the covalent attachment of the resulting PCR products to the surface of a support medium described above (and also described, for example, Schena, M. et al. (1995) *Science* 270: 467-470).

Nucleic acid microarrays may also be constructed by in situ oligonucleotide synthesis as described by Wodicka, L. et al. (1997) *Nature Biotechnology* 15: 1359-1367. By photolithographic methods, precisely defined regions of the matrix are exposed to light. Protective groups which are photolabile are thereby activated and undergo nucleotide addition, whereas regions that are masked from light do not undergo any modification. Subsequent cycles of protection and light activation permit the synthesis of different oligonucleotides at defined positions. Small, defined regions of the genes of the invention may be synthesized on microarrays by solid phase oligonucleotide synthesis.

The nucleic acid molecules of the invention present in a sample or mixture of nucleotides may be hybridized to the microarrays. These nucleic acid molecules can be labeled according to standard methods. In brief, nucleic acid molecules (e.g., mRNA molecules or DNA molecules) are labeled by the incorporation of isotopically or fluorescently labeled nucleotides, e.g., during reverse transcription or DNA synthesis. Hybridization of labeled nucleic acids to microarrays is described (e.g., in Schena, M. et al. (1995) supra; Wodicka, L. et al. (1997), supra; and DeSaizieu A. et al. (1998), supra). The detection and quantification of the hybridized molecule are tailored to the specific incorporated label. Radioactive labels can be detected, for example, as described in Schena, M. et al. (1995) supra) and fluorescent labels may be detected, for example, by the method of Shalon et al. (1996) *Genome Research* 6: 639-645).

The application of the sequences of the invention to DNA microarray technology, as described above, permits comparative analyses of different strains of *C. glutamicum* or other *Corynebacteria*. For example, studies of inter-strain variations based on individual transcript profiles and the identification of genes that are important for specific and/or desired strain properties such as pathogenicity, productivity and stress tolerance are facilitated by nucleic acid array methodologies. Also, comparisons of the profile of expression of genes of the invention during the course of a fermentation reaction are possible using nucleic acid array technology.

EXAMPLE 13

Analysis of the Dynamics of Cellular Protein Populations (Proteomics)

The genes, compositions, and methods of the invention may be applied to study the interactions and dynamics of populations of proteins, termed 'proteomics'. Protein populations of interest include, but are not limited to, the total protein population of *C. glutamicum* (e.g., in comparison with the protein populations of other organisms), those proteins which are active under specific environmental or metabolic conditions (e.g., during fermentation, at high or low temperature, or at high or low pH), or those proteins which are active during specific phases of growth and development.

Protein populations can be analyzed by various well-known techniques, such as gel electrophoresis. Cellular proteins may be obtained, for example, by lysis or extraction, and may be separated from one another using a variety of electrophoretic techniques. Sodium dodecyl sulfate polyacrylamide gel electrophoresis (SDS-PAGE) separates proteins largely on the basis of their molecular weight. Isoelectric focusing polyacrylamide gel electrophoresis (IEF-PAGE) separates proteins by their isoelectric point (which reflects not only the amino acid sequence but also posttranslational modifications of the protein). Another, more preferred method of protein analysis is the consecutive combination of both IEF-PAGE and SDS-PAGE, known as 2-D-gel electrophoresis (described, for example, in Hermann et al. (1998) *Electrophoresis* 19: 3217-3221; Fountoulakis et al. (1998) *Electrophoresis* 19: 1193-1202; Langen et al. (1997) *Electrophoresis* 18: 1184-1192; Antelmann et al. (1997) *Electrophoresis* 18: 1451-1463). Other separation techniques may also be utilized for protein separation, such as capillary gel electrophoresis; such techniques are well known in the art.

Proteins separated by these methodologies can be visualized by standard techniques, such as by staining or labeling. Suitable stains are known in the art, and include Coomassie Brilliant Blue, silver stain, or fluorescent dyes such as Sypro Ruby (Molecular Probes). The inclusion of radioactively labeled amino acids or other protein precursors (e.g., $^{35}$S-methionine, $^{35}$S-cysteine, $^{14}$C-labelled amino acids $^{15}$N-amino acids, $^{15}$NO$_3$ or $^{15}$NH$_4^+$ or $^{13}$C-labelled amino acids) in the medium of *C. glutamicum* permits the labeling of proteins from these cells prior to their separation. Similarly, fluorescent labels may be employed. These labeled proteins can be extracted, isolated and separated according to the previously described techniques.

Proteins visualized by these techniques can be further analyzed by measuring the amount of dye or label used. The amount of a given protein can be determined quantitatively using, for example, optical methods and can be compared to the amount of other proteins in the same gel or in other gels. Comparisons of proteins on gels can be made, for example, by optical comparison, by spectroscopy, by image scanning and analysis of gels, or through the use of photographic films and screens. Such techniques are well-known in the art.

To determine the identity of any given protein, direct sequencing or other standard techniques may be employed. For example, N- and/or C-terminal amino acid sequencing (such as Edman degradation) may be used, as may mass spectrometry (in particular MALDI or ESI techniques (see, e.g., Langen et al. (1997) *Electrophoresis* 18: 1184-1192)). The protein sequences provided herein can be used for the identification of *C. glutamicum* proteins by these techniques.

The information obtained by these methods can be used to compare patterns of protein presence, activity, or modification between different samples from various biological conditions (e.g., different organisms, time points of fermentation, media conditions, or different biotopes, among others). Data obtained from such experiments alone, or in combination with other techniques, can be used for various applications, such as to compare the behavior of various organisms in a given (e.g., metabolic) situation, to increase the productivity of strains which produce fine chemicals or to increase the efficiency of the production of fine chemicals.

Equivalents

Those of ordinary skill in the art will recognize, or will be able to ascertain using no more than routine experimentation, many equivalents to the specific embodiments of the invention described herein. Such equivalents are intended to be encompassed by the following claims.

TABLE 1

Genes Included in the Invention
PHOSPHOENOLPYRUVATE: SUGAR PHOSPHOTRANSFERASE SYSTEM

| Nucleotide SEQ ID NO | Amino Acid SEQ ID NO | Identification Code | Contig. | NT Start | NT Stop | Function |
|---|---|---|---|---|---|---|
| 1 | 2 | RXS00315 | | | | PTS SYSTEM, SUCROSE-SPECIFIC IIABC COMPONENT (EIIABC-SCR) (SUCROSE-PERMEASE IIABC COMPONENT (PHOSPHOTRANSFERASE ENZYME II, ABC COMPONENT) (EC 2.7.1.69) |
| 3 | 4 | F RXA00315 | GR00053 | 6537 | 5452 | PTS SYSTEM, BETA-GLUCOSIDES-SPECIFIC IIABC COMPONENT (EIIABC-BGL) (BETA-GLUCOSIDES-PERMEASE IIABC COMPONENT) (PHOSPHOTRANSFERASE ENZYME II, ABC COMPONENT) (EC 2.7.1.69) |
| 5 | 6 | RXA01503 | GR00424 | 10392 | 10640 | PTS SYSTEM, BETA-GLUCOSIDES-SPECIFIC IIABC COMPONENT (EIIABC-BGL) (BETA-GLUCOSIDES-PERMEASE IIABC COMPONENT) (PHOSPHOTRANSFERASE ENZYME II, ABC COMPONENT) (EC 2.7.1.69) |
| 7 | 8 | RXN01299 | VV0068 | 11954 | 9891 | PTS SYSTEM, FRUCTOSE-SPECIFIC IIBC COMPONENT (EC 2.7.1.69) |
| 9 | 10 | F RXA01299 | GR00375 | 6 | 446 | PTS SYSTEM, FRUCTOSE-SPECIFIC IIBC COMPONENT (EC 2.7.1.69) |
| 11 | 12 | F RXA01883 | GR00538 | 2154 | 2633 | PTS SYSTEM, FRUCTOSE-SPECIFIC IIBC COMPONENT (EC 2.7.1.69) |
| 13 | 14 | F RXA01889 | GR00540 | 77 | 631 | PTS SYSTEM, FRUCTOSE-SPECIFIC IIBC COMPONENT (EC 2.7.1.69) |
| 15 | 16 | RXA00951 | GR00261 | 564 | 172 | PTS SYSTEM, MANNITOL (CRYPTIC)-SPECIFIC IIA COMPONENT (EIIA-(C)MTL) (MANNITOL (CRYPTIC)-PERMEASE IIA COMPONENT) (PHOSPHOTRANSFERASE ENZYME II, A COMPONENT) (EC 2.7.1.69) |
| 17 | 18 | RXN01244 | VV0068 | 14141 | 15844 | PHOSPHOENOLPYRUVATE-PROTEIN PHOSPHOTRANSFERASE (EC 2.7.3.9) |
| 19 | 20 | F RXA01244 | GR00359 | 4837 | 3329 | PHOSPHOENOLPYRUVATE-PROTEIN PHOSPHOTRANSFERASE (EC 2.7.3.9) |
| 21 | 22 | RXA01300 | GR00375 | 637 | 903 | PHOSPHOCARRIER PROTEIN HPR |
| 23 | 24 | RXN03002 | VV0236 | 1437 | 1844 | PTS SYSTEM, MANNITOL (CRYPTIC)-SPECIFIC IIA COMPONENT (EIIA-(C)MTL) (MANNITOL (CRYPTIC)-PERMEASE IIA COMPONENT) (PHOSPHOTRANSFERASE ENZYME II, A COMPONENT) (EC 2.7.1.69) |
| 25 | 26 | RXC00953 | VV0260 | 1834 | 1082 | Membrane Spanning Protein involved in PTS system |
| 27 | 28 | RXC03001 | | | | Membrane Spanning Protein involved in PTS system |
| 29 | 30 | RXN01943 | VV0120 | 4326 | 6374 | PTS SYSTEM, GLUCOSE-SPECIFIC IIABC COMPONENT (EC 2.7.1.69) |
| 31 | 32 | F RXA02191 | GR00642 | 3395 | 4633 | PHOSPHOENOLPYRUVATE SUGAR PHOSPHOTRANSFERASE |
| 33 | 34 | F RXA01943 | GR00557 | 3944 | 3540 | crr gene; phosphotransferase system glucose-specific enzyme III |

TABLE 2

GENES IDENTIFIED FROM GENBANK

| GenBank™ Accession No. | Gene Name | Gene Function | Reference |
|---|---|---|---|
| A09073 | ppg | Phosphoenol pyruvate carboxylase | Bachmann, B. et al. "DNA fragment coding for phosphoenolpyruvat corboxylase, recombinant DNA carrying said fragment, strains carrying the recombinant DNA and method for producing L-aminino acids using said strains," Patent: EP 0358940-A 3 Mar. 21, 1990 |
| A45579, A45581, A45583, A45585, A45587 | | Threonine dehydratase | Moeckel, B. et al. "Production of L-isoleucine by means of recombinant micro-organisms with deregulated threonine dehydratase," Patent: WO 9519442-A 5 Jul. 20, 1995 |
| AB003132 | murC; ftsQ; ftsZ | | Kobayashi, M. et al. "Cloning, sequencing, and characterization of the ftsZ gene from coryneform bacteria," Biochem. Biophys. Res. Commun., 236(2): 383-388 (1997) |
| AB015023 | murC; ftsQ | | Wachi, M. et al. "A murC gene from Coryneform bacteria," Appl. Microbiol. Biotechnol., 51(2): 223-228 (1999) |
| AB018530 | dtsR | | Kimura, E. et al. "Molecular cloning of a novel gene, dtsR, which rescues the detergent sensitivity of a mutant derived from *Brevibacterium lactofermentum*," Biosci. Biotechnol. Biochem., 60(10): 1565-1570 (1996) |
| AB018531 | dtsR1; dtsR2 | D-glutamate racemase | |
| AB020624 | murI | transketolase | |
| AB023377 | tkt | Glutamine 2-oxoglutarate aminotransferase large and small subunits | |
| AB024708 | gltB; gltD | aconitase | |
| AB025424 | acn | Replication protein | |
| AB027714 | rep | Replication protein; aminoglycoside adenyltransferase | |
| AB027715 | rep; aad | N-acetylglutamate-5-semialdehyde dehydrogenase | |
| AF005242 | argC | Glutamine synthetase | |
| AF005655 | glnA | cyclase | |
| AF030405 | hisF | Argininosuccinate synthetase | |
| AF030520 | argG | Ornithine carbamoyltransferase | |
| AF031518 | argF | 3-dehydroquinate dehydratase | |
| AF036932 | aroD | Pyruvate carboxylase | |
| AF038548 | pyc | Dipeptide-binding protein; adenine phosphoribosyltransferase; GTP pyrophosphokinase | Wehmeier, L. et al. "The role of the *Corynebacterium glutamicum* rel gene in (p)ppGpp metabolism," Microbiology, 144: 1853-1862 (1998) |
| AF038651 | dciAE; apt; rel | Arginine repressor | |
| AF041436 | argR | Inositol monophosphate phosphatase | |
| AF045998 | impA | Argininosuccinate lyase | |
| AF048764 | argH | N-acetylglutamylphosphate reductase; ornithine acetyltransferase; N-acetylglutamate kinase; acetylornithine transminase; ornithine carbamoyltransferase; arginine repressor; argininosuccinate synthase; argininosuccinate lyase | |
| AF049897 | argC; argJ; argB; argD; argF; argR; argG; argH | Enoyl-acyl carrier protein reductase | |
| AF050109 | inhA | ATP phosphoribosyltransferase | |
| AF050166 | hisG | | |

TABLE 2-continued

GENES IDENTIFIED FROM GENBANK

| GenBank™ Accession No. | Gene Name | Gene Function | Reference |
|---|---|---|---|
| AF051846 | hisA | Phosphoribosylformimino-5-amino-1-phosphoribosyl-4-imidazolecarboxamide isomerase | |
| AF052652 | metA | Homoserine O-acetyltransferase | Park, S. et al. "Isolation and analysis of metA, a methionine biosynthetic gene encoding homoserine acetyltransferase in *Corynebacterium glutamicum*," Mol. Cells., 8(3): 286-294 (1998) |
| AF053071 | aroB | Dehydroquinate synthetase | |
| AF060558 | hisH | Glutamine amidotransferase | |
| AF086704 | hisE | Phosphoribosyl-ATP-pyrophosphohydrolase | |
| AF114233 | aroA | 5-enolpyruvylshikimate 3-phosphate synthase | |
| AF116184 | panD | L-aspartate-alpha-decarboxylase precursor | Dusch, N. et al. "Expression of the *Corynebacterium glutamicum* panD gene encoding L-aspartate-alpha-decarboxylase leads to pantothenate overproduction in *Escherichia coli*," Appl. Environ. Microbiol., 65(4) 1530-1539 (1999) |
| AF124518 | aroD; aroE | 3-dehydroquinase; shikimate dehydrogenase | |
| AF124600 | aroC; aroK; aroB; pepQ | Chorismate synthase; shikimate kinase; 3-dehydroquinate synthase; putative cytoplasmic peptidase | |
| AF145897 | inhA | | |
| AF145898 | inhA | | |
| AJ001436 | ectP | Transport of ectoine, glycine betaine, proline | Peter, H. et al. "*Corynebacterium glutamicum* is equipped with four secondary carriers for compatible solutes: Identification, sequencing, and characterization of the proline/ectoine uptake system, ProP, and the ectoine/proline/glycine betaine carrier, EctP," J. Bacteriol., 180(22): 6005-6012 (1998) |
| AJ004934 | dapD | Tetrahydrodipicolinate succinylase (incomplete) | Wehrmann, A. et al. "Different modes of diaminopimelate synthesis and their role in cell wall integrity: A study with *Corynebacterium glutamicum*," J. Bacteriol., 180(12): 3159-3165 (1998) |
| AJ007732 | ppc; secG; amt; ocd; soxA | Phosphoenolpyruvate-carboxylase; ?; high affinity ammonium uptake protein; putative ornithine-cyclodecarboxylase; sarcosine oxidase | |
| AJ010319 | ftsY, glnB, glnD; srp; amtP | Involved in cell division; PII protein; uridylyltransferase (uridylyl-removing enzmye); signal recognition particle; low affinity ammonium uptake protein | Jakoby, M. et al. "Nitrogen regulation in *Corynebacterium glutamicum*; Isolation of genes involved in biochemical characterization of corresponding proteins," FEMS Microbiol, 173(2): 303-310 (1999) |
| AJ132968 | cat | Chloramphenicol acetyl transferase | |
| AJ224946 | mqo | L-malate: quinone oxidoreductase | Molenaar, D. et al. "Biochemical and genetic characterization of the membrane-associated malate dehydrogenase (acceptor) from *Corynebacterium glutamicum*," Eur. J. Biochem., 254(2): 395-403 (1998) |
| AJ238250 | ndh | NADH dehydrogenase | |
| AJ238703 | porA | Porin | Lichtinger, T. et al. "Biochemical and biophysical characterization of the cell wall porin of *Corynebacterium glutamicum*: The channel is formed by a low molecular mass polypeptide," Biochemistry, 37(43): 15024-15032 (1998) |
| D17429 | | Transposable element IS31831 | Vertes, A. A. et al. "Isolation and characterization of IS31831, a transposable element from *Corynebacterium glutamicum*," Mol. Microbiol., 11(4): 739-746 (1994) |
| D84102 | odhA | 2-oxoglutarate dehydrogenase | Usuda, Y. et al. "Molecular cloning of the *Corynebacterium glutamicum* (*Brevibacterium lactofermentum* AJ12036) odhA gene encoding a novel type of 2-oxoglutarate dehydrogenase," Microbiology, 142: 3347-3354 (1996) |

TABLE 2-continued

GENES IDENTIFIED FROM GENBANK

| GenBank™ Accession No. | Gene Name | Gene Function | Reference |
|---|---|---|---|
| E01358 | hdh; hk | Homoserine dehydrogenase; homoserine kinase | Katsumata, R. et al. "Production of L-threonine and L-isoleucine," Patent: JP 1987232392-A 1 Oct. 12, 1987 |
| E01359 | | Upstream of the start codon of homoserine kinase gene | Katsumata, R. et al. "Production of L-threonine and L-isoleucine," Patent: JP 1987232392-A 2 Oct. 12, 1987 |
| E01375 | | Tryptophan operon | |
| E01376 | trpL; trpE | Leader peptide; anthranilate synthase | Matsui, K. et al. "Tryptophan operon, peptide and protein coded thereby, utilization of tryptophan operon gene expression and production of tryptophan," Patent: JP 1987244382-A 1 Oct. 24, 1987 |
| E01377 | | Promoter and operator regions of tryptophan operon | Matsui, K. et al. "Tryptophan operon, peptide and protein coded thereby, utilization of tryptophan operon gene expression and production of tryptophan," Patent: JP 1987244382-A 1 Oct. 24, 1987 |
| E03937 | | Biotin-synthase | Hatakeyama, K. et al. "DNA fragment containing gene capable of coding biotin synthetase and its utilization," Patent: JP 1992278088-A 1 Oct. 2, 1992 |
| E04040 | | Diamino pelargonic acid aminotransferase | Kohama, K. et al. "Gene coding diaminopelargonic acid aminotransferase and desthiobiotin synthetase and its utilization," Patent: JP 1992330284-A 1 Nov. 18, 1992 |
| E04041 | | Desthiobiotinsynthetase | Kohama, K. et al. "Gene coding diaminopelargonic acid aminotransferase and desthiobiotin synthetase and its utilization," Patent: JP 1992330284-A 1 Nov. 18, 1992 |
| E04307 | | Flavum aspartase | Kurusu, Y. et al. "Gene DNA coding aspartase and utilization thereof," Patent: JP 1993030977-A 1 Feb. 9, 1993 |
| E04376 | | Isocitric acid lyase | Katsumata, R. et al. "Gene manifestation controlling DNA," Patent: JP 1993056782-A 3 Mar. 9, 1993 |
| E04377 | | Isocitric acid lyase N-terminal fragment | Katsumata, R. et al. "Gene manifestation controlling DNA," Patent: JP 1993056782-A 3 Mar. 9, 1993 |
| E04484 | | Prephenate dehydratase | Sotouchi, N. et al. "Production of L-phenylalanine by fermentation," Patent: JP 1993076352-A 2 Mar. 30, 1993 |
| E05108 | | Aspartokinase | Fugono, N. et al. "Gene DNA coding Aspartokinase and its use," Patent: JP 1993184366-A 1 Jul. 27, 1993 |
| E05112 | | Dihydro-dipicolinate synthetase | Hatakeyama, K. et al. "Gene DNA coding dihydrodipicolinic acid synthetase and its use," Patent: JP 1993184371-A 1 Jul. 27, 1993 |
| E05776 | | Diaminopimelic acid dehydrogenase | Kobayashi, M. et al. "Gene DNA coding Diaminopimelic acid dehydrogenase and its use," Patent: JP 1993284970-A 1 Nov. 2, 1993 |
| E05779 | | Threonine synthase | Kohama, K. et al. "Gene DNA coding threonine synthase and its use," Patent: JP 1993284972-A 1 Nov. 2, 1993 |
| E06110 | | Prephenate dehydratase | Kikuchi, T. et al. "Production of L-phenylalanine by fermentation method," Patent: JP 1993344881-A 1 Dec. 27, 1993 |
| E06111 | | Mutated Prephenate dehydratase | Kikuchi, T. et al. "Production of L-phenylalanine by fermentation method," Patent: JP 1993344881-A 1 Dec. 27, 1993 |
| E06146 | | Acetohydroxy acid synthetase | Inui, M. et al. "Gene capable of coding Acetohydroxy acid synthetase and its use," Patent: JP 1993344893-A 1 Dec. 27, 1993 |
| E06825 | | Aspartokinase | Sugimoto, M. et al. "Mutant aspartokinase gene," patent: JP 1994062866-A 1 Mar. 8, 1994 |
| E06826 | | Mutated aspartokinase alpha subunit | Sugimoto, M. et al. "Mutant aspartokinase gene," patent: JP 1994062866-A 1 Mar. 8, 1994 |
| E06827 | | Mutated aspartokinase alpha subunit | Sugimoto, M. et al. "Mutant aspartokinase gene," patent: JP 1994062866-A 1 Mar. 8, 1994 |

TABLE 2-continued

GENES IDENTIFIED FROM GENBANK

| GenBank™ Accession No. | Gene Name | Gene Function | Reference |
|---|---|---|---|
| E07701 | secY | | Honno, N. et al. "Gene DNA participating in integration of membraneous protein to membrane," Patent: JP 1994169780-A 1 Jun. 21, 1994 |
| E08177 | | Aspartokinase | Sato, Y. et al. "Genetic DNA capable of coding Aspartokinase released from feedback inhibition and its utilization," Patent: JP 1994261766-A 1 Sep. 20, 1994 |
| E08178, E08179, E08180, E08181, E08182 | | Feedback inhibition-released Aspartokinase | Sato, Y. et al. "Genetic DNA capable of coding Aspartokinase released from feedback inhibition and its utilization," Patent: JP 1994261766-A 1 Sep. 20, 1994 |
| E08232 | | Acetohydroxy-acid isomeroreductase | Inui, M. et al. "Gene DNA coding acetohydroxy acid isomeroreductase," Patent: JP 1994277067-A 1 Oct. 4, 1994 |
| E08234 | secE | | Asai, Y. et al. "Gene DNA coding for translocation machinery of protein," Patent: JP 1994277073-A 1 Oct. 4, 1994 |
| E08643 | | FT aminotransferase and desthiobiotin synthetase promoter region | Hatakeyama, K. et al. "DNA fragment having promoter function in coryneform bacterium," Patent: JP 1995031476-A 1 Feb. 3, 1995 |
| E08646 | | Biotin synthetase | Hatakeyama, K. et al. "DNA fragment having promoter function in coryneform bacterium," Patent: JP 1995031476-A 1 Feb. 3, 1995 |
| E08649 | | Aspartase | Kohama, K. et al "DNA fragment having promoter function in coryneform bacterium," Patent: JP 1995031478-A 1 Feb. 3, 1995 |
| E08900 | | Dihydrodipicolinate reductase | Madori, M. et al. "DNA fragment containing gene coding Dihydrodipicolinate acid reductase and utilization thereof," Patent: JP 1995075578-A 1 Mar. 20, 1995 |
| E08901 | | Diaminopimelic acid decarboxylase | Madori, M. et al. "DNA fragment containing gene coding Diaminopimelic acid decarboxylase and utilization thereof," Patent: JP 1995075579-A 1 Mar. 20, 1995 |
| E12594 | | Serine hydroxymethyltransferase | Hatakeyama, K. et al. "Production of L-tryptophan," Patent: JP 1997028391-A 1 Feb. 4, 1997 |
| E12760, E12759, E12758 | | transposase | Moriya, M. et al. "Amplification of gene using artificial transposon," Patent: JP 1997070291-A Mar. 18, 1997 |
| E12764 | | Arginyl-tRNA synthetase; diaminopimelic acid decarboxylase | Moriya, M. et al. "Amplification of gene using artificial transposon," Patent: JP 1997070291-A Mar. 18, 1997 |
| E12767 | | Dihydrodipicolinic acid synthetase | Moriya, M. et al. "Amplification of gene using artificial transposon," Patent: JP 1997070291-A Mar. 18, 1997 |
| E12770 | | aspartokinase | Moriya, M. et al. "Amplification of gene using artificial transposon," Patent: JP 1997070291-A Mar. 18, 1997 |
| E12773 | | Dihydrodipicolinic acid reductase | Moriya, M. et al. "Amplification of gene using artificial transposon," Patent: JP 1997070291-A Mar. 18, 1997 |
| E13655 | | Glucose-6-phosphate dehydrogenase | Hatakeyama, K. et al. "Glucose-6-phosphate dehydrogenase and DNA capable of coding the same," Patent: JP 1997224661-A 1 Sep. 2, 1997 |
| L01508 | IlvA | Threonine dehydratase | Moeckel, B. et al. "Functional and structural analysis of the threonine dehydratase of Corynebacterium glutamicum," J. Bacteriol., 174: 8065-8072 (1992) |
| L07603 | EC 4.2.1.15 | 3-deoxy-D-arabinoheptulosonate-7-phosphate synthase | Chen, C. et al. "The cloning and nucleotide sequence of Corynebacterium glutamicum 3-deoxy-D-arabinoheptulosonate-7-phosphate synthase gene," FEMS Microbiol. Lett., 107: 223-230 (1993) |
| L09232 | IlvB; ilvN; ilvC | Acetohydroxy acid synthase large subunit; Acetohydroxy acid synthase small subunit; Acetohydroxy acid isomeroreductase | Keilhauer, C. et al. "Isoleucine synthesis in Corynebacterium glutamicum: molecular analysis of the ilvB-ilvN-ilvC operon," J. Bacteriol., 175(17): 5595-5603 (1993) |

TABLE 2-continued

GENES IDENTIFIED FROM GENBANK

| GenBank™ Accession No. | Gene Name | Gene Function | Reference |
|---|---|---|---|
| L18874 | PtsM | Phosphoenolpyruvate sugar phosphotransferase | Fouet, A et al. "*Bacillus subtilis* sucrose-specific enzyme II of the phosphotransferase system: expression in *Escherichia coli* and homology to enzymes II from enteric bacteria," PNAS USA, 84(24): 8773-8777 (1987); Lee, J. K. et al. "Nucleotide sequence of the gene encoding the *Corynebacterium glutamicum* mannose enzyme II and analyses of the deduced protein sequence," FEMS Microbiol. Lett., 119(1-2): 137-145 (1994) |
| L27123 | aceB | Malate synthase | Lee, H-S. et al. "Molecular characterization of aceB, a gene encoding malate synthase in *Corynebacterium glutamicum*," J. Microbiol. Biotechnol., 4(4): 256-263 (1994) |
| L27126 | | Pyruvate kinase | Jetten, M. S. et al. "Structural and functional analysis of pyruvate kinase from *Corynebacterium glutamicum*," Appl. Environ. Microbiol., 60(7): 2501-2507 (1994) |
| L28760 | aceA | Isocitrate lyase | |
| L35906 | dtxr | Diphtheria toxin repressor | Oguiza, J. A. et al. "Molecular cloning, DNA sequence analysis, and characterization of the *Corynebacterium diphtheriae* dtxR from *Brevibacterium lactofermentum*," J. Bacteriol., 177(2): 465-467 (1995) |
| M13774 | | Prephenate dehydratase | Follettie, M. T. et al. "Molecular cloning and nucleotide sequence of the *Corynebacterium glutamicum* pheA gene," J. Bacteriol., 167: 695-702 (1986) |
| M16175 | 5S rRNA | | Park, Y-H. et al. "Phylogenetic analysis of the coryneform bacteria by 5S rRNA sequences," J. Bacteriol., 169: 1801-1806 (1987) |
| M16663 | trpE | Anthranilate synthase, 5' end | Sano, K. et al. "Structure and function of the trp operon control regions of *Brevibacterium lactofermentum*, a glutamic-acid-producing bacterium," Gene, 52: 191-200 (1987) |
| M16664 | trpA | Tryptophan synthase, 3' end | Sano, K. et al. "Structure and function of the trp operon control regions of *Brevibacterium lactofermentum*, a glutamic-acid-producing bacterium," Gene, 52: 191-200 (1987) |
| M25819 | | Phosphoenolpyruvate carboxylase | O'Regan, M. et al. "Cloning and nucleotide sequence of the Phosphoenolpyruvate carboxylase-coding gene of *Corynebacterium glutamicum* ATCC13032," Gene, 77(2): 237-251 (1989) |
| M85106 | | 23S rRNA gene insertion sequence | Roller, C. et al. "Gram-positive bacteria with a high DNA G + C content are characterized by a common insertion within their 23S rRNA genes," J. Gen. Microbiol., 138: 1167-1175 (1992) |
| M85107, M85108 | | 23S rRNA gene insertion sequence | Roller, C. et al. "Gram-positive bacteria with a high DNA G + C content are characterized by a common insertion within their 23S rRNA genes," J. Gen. Microbiol., 138: 1167-1175 (1992) |
| M89931 | aecD; brnQ; yhbw | Beta C-S lyase; branched-chain amino acid uptake carrier; hypothetical protein yhbw | Rossol, I. et al. "The *Corynebacterium glutamicum* aecD gene encodes a C-S lyase with alpha, beta-elimination activity that degrades aminoethylcysteine," J. Bacteriol., 174(9): 2968-2977 (1992); Tauch, A. et al. "Isoleucine uptake in *Corynebacterium glutamicum* ATCC 13032 is directed by the brnQ gene product," Arch. Microbiol., 169(4): 303-312 (1998) |
| S59299 | trp | Leader gene (promoter) | Herry, D. M. et al. "Cloning of the trp gene cluster from a tryptophan-hyperproducing strain of *Corynebacterium glutamicum*: identification of a mutation in the trp leader sequence," Appl. Environ. Microbiol., 59(3): 791-799 (1993) |
| U11545 | trpD | Anthranilate phosphoribosyltransferase | O'Gara, J. P. and Dunican, L. K. (1994) Complete nucleotide sequence of the *Corynebacterium glutamicum* ATCC 21850 trpD gene." Thesis, Microbiology Department, University College Galway, Ireland. |

TABLE 2-continued

GENES IDENTIFIED FROM GENBANK

| GenBank ™ Accession No. | Gene Name | Gene Function | Reference |
|---|---|---|---|
| U13922 | cgIIM; cgIIR; cIgIIR | Putative type II 5-cytosoine methyltransferase; putative type II restriction endonuclease; putative type I or type III restriction endonuclease | Schafer, A. et al. "Cloning and characterization of a DNA region encoding a stress-sensitive restriction system from *Corynebacterium glutamicum* ATCC 13032 and analysis of its role in intergeneric conjugation with *Escherichia coli*," J. Bacteriol., 176(23): 7309-7319 (1994); Schafer, A. et al. "The *Corynebacterium glutamicum* cgIIM gene encoding a 5-cytosine in an McrBC-deficient *Escherichia coli* strain," Gene, 203(2): 95-101 (1997) |
| U14965 | recA | | |
| U31224 | ppx | | Ankri, S. et al. "Mutations in the *Corynebacterium glutamicum* proline biosynthetic pathway: A natural bypass of the proA step," J. Bacteriol., 178(15): 4412-4419 (1996) |
| U31225 | proC | L-proline: NADP + 5-oxidoreductase | Ankri, S. et al. "Mutations in the *Corynebacterium glutamicum* proline biosynthetic pathway: A natural bypass of the proA step," J. Bacteriol., 178(15): 4412-4419 (1996) |
| U31230 | obg; proB; unkdh | ?; gamma glutamyl kinase; similar to D-isomer specific 2-hydroxy acid dehydrogenases | Ankri, S. et al. "Mutations in the *Corynebacterium glutamicum* proline biosynthetic pathway: A natural bypass of the proA step," J. Bacteriol., 178(15): 4412-4419 (1996) |
| U31281 | bioB | Biotin synthase | Serebriiskii, I. G., "Two new members of the bio B superfamily: Cloning, sequencing and expression of bio B genes of *Methylobacillus flagellatum* and *Corynebacterium glutamicum*," Gene, 175: 15-22 (1996) |
| U35023 | thtR; accBC | Thiosulfate sulfurtransferase; acyl CoA carboxylase | Jager, W. et al. "A *Corynebacterium glutamicum* gene encoding a two-domain protein similar to biotin carboxylases and biotin-carboxyl-carrier proteins," Arch. Microbiol., 166(2); 76-82 (1996) |
| U43535 | cmr | Multidrug resistance protein | Jager, W. et al. "A *Corynebacterium glutamicum* gene conferring multidrug resistance in the heterologous host *Escherichia coli*," J. Bacteriol., 179(7): 2449-2451 (1997) |
| U43536 | clpB | Heat shock ATP-binding protein | |
| U53587 | aphA-3 | 3'5"-aminoglycoside phosphotransferase | |
| U89648 | | *Corynebacterium glutamicum* unidentified sequence involved in histidine biosynthesis, partial sequence | |
| X04960 | trpA; trpB; trpC; trpD; trpE; trpG; trpL | Tryptophan operon | Matsui, K. et al. "Complete nucleotide and deduced amino acid sequences of the *Brevibacterium lactofermentum* tryptophan operon," Nucleic Acids Res., 14(24): 10113-10114 (1986) |
| X07563 | lysA | DAP decarboxylase (meso-diaminopimelate decarboxylase, EC 4.1.1.20) | Yeh, P. et al. "Nucleic sequence of the lysA gene of *Corynebacterium glutamicum* and possible mechanisms for modulation of its expression," Mol. Gen. Genet., 212(1): 112-119 (1988) |
| X14234 | EC 4.1.1.31 | Phosphoenolpyruvate carboxylase | Eikmanns, B. J. et al. "The Phosphoenolpyruvate carboxylase gene of *Corynebacterium glutamicum*: Molecular cloning, nucleotide sequence, and expression," Mol. Gen. Genet., 218(2): 330-339 (1989); Lepiniec, L. et al. "Sorghum Phosphoenolpyruvate carboxylase gene family: structure, function and molecular evolution," Plant. Mol. Biol., 21 (3): 487-502 (1993) |
| X17313 | fda | Fructose-bisphosphate aldolase | Von der Osten, C. H. et al. "Molecular cloning, nucleotide sequence and fine-structural analysis of the *Corynebacterium glutamicum* fda gene: structural comparison of *C. glutamicum* fructose-1,6-biphosphate aldolase to class I and class II aldolases," Mol. Microbiol., |
| X53993 | dapA | L-2,3-dihydrodipicolinate synthetase (EC 4.2.1.52) | Bonnassie, S. et al. "Nucleic sequence of the dapA gene from *Corynebacterium glutamicum*," Nucleic Acids Res., 18(21): 6421 (1990) |

TABLE 2-continued

GENES IDENTIFIED FROM GENBANK

| GenBank™ Accession No. | Gene Name | Gene Function | Reference |
|---|---|---|---|
| X54223 | | AttB-related site | Cianciotto, N. et al. "DNA sequence homology between att B-related sites of *Corynebacterium diphtheriae*, *Corynebacterium ulcerans*, *Corynebacterium glutamicum*, and the attP site of lambdacorynephage," FEMS. Microbiol. Lett., 66: 299-302 (1990) |
| X54740 | argS; lysA | Arginyl-tRNA synthetase; Diaminopimelate decarboxylase | Marcel, T. et al. "Nucleotide sequence and organization of the upstream region of the *Corynebacterium glutamicum* lysA gene," Mol. Microbiol. 4(11): 1819-1830 (1990) |
| X55994 | trpL; trpE | Putative leader peptide; anthranilate synthase component 1 | Heery, D. M. et al. "Nucleotide sequence of the *Corynebacterium glutamicum* trpE gene," Nucleic Acids Res., 18(23): 7138 (1990) |
| X56037 | thrC | Threonine synthase | Han, K. S. et al. "The molecular structure of the *Corynebacterium glutamicum* threonine synthase gene," Mol. Microbiol. 4(10): 1693-1702 (1990) |
| X56075 | attB-related site | Attachment site | Cianciotto, N. et al. "DNA sequence homology between att B-related sites of *Corynebacterium diphtheriae*, *Corynebacterium ulcerans*, *Corynebacterium glutamicum*, and the attP site of lambdacorynephage," FEMS. Microbiol, Lett., 66: 299-302 (1990) |
| X57226 | lysC-alpha; lysC-beta; asd | Aspartokinase-alpha subunit; Aspartokinase-beta subunit; aspartate beta semialdehyde dehydrogenase | Kalinowski, J. et al. "Genetic and biochemical analysis of the Aspartokinase from *Corynebacterium glutamicum*," Mol. Microbiol., 5(5): 1197-1204 (1991); Kalinowski, J. et al. "Aspartokinase genes lysC alpha and lysC beta overlap and are adjacent to the aspartate beta-semialdehyde dehydrogenase gene asd in *Corynebacterium glutamicum*," Mol. Gen. Genet., 224(3): 317-324 (1990) |
| X59403 | gap; pgk; tpi | Glyceraldehyde-3-phosphate; phosphoglycerate kinase; triosephosphate isomerase | Eikmanns, B. J. "Identification, sequence analysis, and expression of a *Corynebacterium glutamicum* gene cluster encoding the three glycolytic enzymes glyceraldehyde-3-phosphate dehydrogenase, 3-phosphoglycerate kinase, and triosephosphate isomeras," J. Bacteriol., 174(19): 6076-6086 (1992) |
| X59404 | gdh | Glutamate dehydrogenase | Bormann, E. R. et al. "Molecular analysis of the *Corynebacterium glutamicum* gdh gene encoding glutamate dehydrogenase," Mol. Microbiol., 6(3): 317-326 (1992) |
| X60312 | lysI | L-lysine permease | Seep-Feldhaus, A. H. et al. "Molecular analysis of the *Corynebacterium glutamicum* lysI gene involved in lysine uptake," Mol. Microbiol., 5(12): 2995-3005 (1991) |
| X66078 | cop1 | Ps1 protein | Joliff, G. et al. "Cloning and nucleotide sequence of the csp1 gene encoding PS1, one of the two major secreted proteins of *Corynebacterium glutamicum*: The deduced N-terminal region of PS1 is similar to the Mycobacterium antigen 85 complex," Mol. Microbiol., 6(16): 2349-2362 (1992) |
| X66112 | glt | Citrate synthase | Eikmanns, B. J. et al. "Cloning sequence, expression and transcriptional analysis of the *Corynebacterium glutamicum* gltA gene encoding citrate synthase," Microbiol., 140: 1817-1828 (1994) |
| X67737 | dapB | Dihydrodipicolinate reductase | |
| X69103 | csp2 | Surface layer protein PS2 | Peyret, J. L. et al. "Characterization of the cspB gene encoding PS2, an ordered surface-layer protein in *Corynebacterium glutamicum*," Mol. Microbiol., 9(1): 97-109 (1993) |
| X69104 | | IS3 related insertion element | Bonamy, C. et al. "Identification of IS1206, a *Corynebacterium glutamicum* IS3-related insertion sequence and phylogenetic analysis," Mol. Microbiol., 14(3): 571-581 (1994) |

TABLE 2-continued

GENES IDENTIFIED FROM GENBANK

| GenBank™ Accession No. | Gene Name | Gene Function | Reference |
|---|---|---|---|
| X70959 | leuA | Isopropylmalate synthase | Patek, M. et al. "Leucine synthesis in *Corynebacterium glutamicum*: enzyme activities, structure of leuA, and effect of leuA inactivation on lysine synthesis," Appl. Environ. Microbiol., 60(1): 133-140 (1994) |
| X71489 | icd | Isocitrate dehydrogenase (NADP+) | Eikmanns, B. J. et al. "Cloning sequence analysis, expression, and inactivation of the *Corynebacterium glutamicum* icd gene encoding isocitrate dehydrogenase and biochemical characterization of the enzyme," J. Bacteriol., 177(3): 774-782 (1995) |
| X72855 X75083, X70584 | GDHA mtrA | Glutamate dehydrogenase (NADP+) 5-methyltryptophan resistance | Heery, D. M. et al. "A sequence from a tryptophan-hyperproducing strain of *Corynebacterium glutamicum* encoding resistance to 5-methyltryptophan," Biochem. Biophys. Res. Commun., 201(3): 1255-1262 (1994) |
| X75085 | recA | | Fitzpatrick, R. et al. "Construction and characterization of recA mutant strains of *Corynebacterium glutamicum* and *Brevibacterium lactofermentum*," Appl. Microbiol. Biotechnol., 42(4): 575-580 (1994) |
| X75504 | aceA; thiX | Partial Isocitrate lyase; ? | Reinscheid, D. J. et al. "Characterization of the isocitrate lyase gene from *Corynebacterium glutamicum* and biochemical analysis of the enzyme," J. Bacteriol., 176(12): 3474-3483 (1994) |
| X76875 | | ATPase beta-subunit | Ludwig, W. et al. "Phylogenetic relationships of bacteria based on comparative sequence analysis of elongation factor Tu and ATP-synthase beta-subunit genes," Antonie Van Leeuwenhoek, 64: 285-305 (1993) |
| X77034 | tuf | Elongation factor Tu | Ludwig, W. et al. "Phylogenetic relationships of bacteria based on comparative sequence analysis of elongation factor Tu and ATP-synthase beta-subunit genes," Antonie Van Leeuwenhoek, 64: 285-305 (1993) |
| X77384 | recA | | Billman-Jacobe, H. "Nucleotide sequence of a recA gene from *Corynebacterium glutamicum*," DNA Seq., 4(6): 403-404 (1994) |
| X78491 | aceB | Malate synthase | Reinscheid, D. J. et al. "Malate synthase from *Corynebacterium glutamicum* pta-ack operon encoding phosphotransacetylase: sequence analysis," Microbiology, 140: 3099-3108 (1994) |
| X80629 | 16S rDNA | 16S ribosomal RNA | Rainey, F. A. et al. "Phylogenetic analysis of the genera *Rhodococcus* and *Nocardia* and evidence for the evolutionary origin of the genus *Nocardia* from within the radiation of *Rhodococcus* species," Microbiol., 141: 523-528 (1995) |
| X81191 | gluA; gluB; gluC; gluD | Glutamate uptake system | Kronemeyer, W. et al. "Structure of the gluABCD cluster encoding the glutamate uptake system of *Corynebacterium glutamicum*," J. Bacteriol., 177(5): 1152-1158 (1995) |
| X81379 | dapE | Succinyldiaminopimelate desuccinylase | Wehrmann, A. et al. "Analysis of different DNA fragments of *Corynebacterium glutamicum* complementing dapE of *Escherichia coli*," Microbiology, 40: 3349-56 (1994) |
| X82061 | 16S rDNA | 16S ribosomal RNA | Ruimy, R. et al. "Phylogeny of the genus *Corynebacterium* deduced from analyses of small-subunit ribosomal DNA sequences," Int. J. Syst. Bacteriol., 45(4): 740-746 (1995) |
| X82928 | asd; lysC | Aspartate-semialdehyde dehydrogenase; ? | Serebrijski, I. et al. "Multicopy suppression by asd gene and osmotic stress-dependent complementation by heterologous proA in proA mutants," J. Bacteriol., 177(24): 7255-7260 (1995) |
| X82929 | proA | Gamma-glutamyl phosphate reductase | Serebrijski, I. et al. "Multicopy suppression by asd gene and osmotic stress-dependent complementation by heterologous proA in proA mutants," J. Bacteriol., 177(24): 7255-7260 (1995) |

TABLE 2-continued

GENES IDENTIFIED FROM GENBANK

| GenBank™ Accession No. | Gene Name | Gene Function | Reference |
|---|---|---|---|
| X84257 | 16S rDNA | 16S ribosomal RNA | Pascual, C. et al. "Phylogenetic analysis of the genus *Corynebacterium* based on 16S rRNA gene sequences," Int. J. Syst. Bacteriol., 45(4): 724-728 (1995) |
| X85965 | aroP; dapE | Aromatic amino acid permease; ? | Wehrmann, A. et al. "Functional analysis of sequences adjacent to dapE of *Corynebacterium glutamicum* proline reveals the presence of aroP, which encodes the aromatic amino acid transporter," J. Bacteriol, 177(20): 5991-5993 (1995) |
| X86157 | argB; argC; argD; argF; argJ | Acetylglutamate kinase; N-acetyl-gamma-glutamyl-phosphate reductase; acetylornithine aminotransferase; ornithine carbamoyltransferase; glutamate N-acetyltransferase | Sakanyan, V. et al. "Genes and enzymes of the acetyl cycle of arginine biosynthesis in *Corynebacterium glutamicum*: enzyme evolution in the early steps of the arginine pathway," Microbiology, 142: 99-108 (1996) |
| X89084 | pta; ackA | Phosphate acetyltransferase; acetate kinase | Reinscheid, D. J. et al. "Cloning, sequence analysis, expression and inactivation of the *Corynebacterium glutamicum* pta-ack operon encoding phosphotransacetylase and acetate kinase," Microbiology, 145: 503-513 (1999) |
| X89850 | attB | Attachment site | Le Marrec, C. et al. "Genetic characterization of site-specific integration functions of phi AAU2 infecting "*Arthrobacter aureus* C70," J. Bacteriol., 178(7): 1996-2004 (1996) |
| X90356 | | Promoter fragment F1 | Patek, M. et al. "Promoters from *Corynebacterium glutamicum*: cloning, molecular analysis and search for a consensus motif", Microbiology, 142: 1297-1309 (1996) |
| X90357 | | Promoter fragment F2 | Patek, M. et al. "Promoters from *Corynebacterium glutamicum*: cloning, molecular analysis and search for a consensus motif", Microbiology, 142: 1297-1309 (1996) |
| X90358 | | Promoter fragment F10 | Patek, M. et al. "Promoters from *Corynebacterium glutamicum*: cloning, molecular analysis and search for a consensus motif", Microbiology, 142: 1297-1309 (1996) |
| X90359 | | Promoter fragment F13 | Patek, M. et al. "Promoters from *Corynebacterium glutamicum*: cloning, molecular analysis and search for a consensus motif", Microbiology, 142: 1297-1309 (1996) |
| X90360 | | Promoter fragment F22 | Patek, M. et al. "Promoters from *Corynebacterium glutamicum*: cloning, molecular analysis and search for a consensus motif", Microbiology, 142: 1297-1309 (1996) |
| X90361 | | Promoter fragment F34 | Patek, M. et al. "Promoters from *Corynebacterium glutamicum*: cloning, molecular analysis and search for a consensus motif", Microbiology, 142: 1297-1309 (1996) |
| X90362 | | Promoter fragment F37 | Patek, M. et al. "Promoters from *Corynebacterium glutamicum*: cloning, molecular analysis and search for a consensus motif", Microbiology, 142: 1297-1309 (1996) |
| X90363 | | Promoter fragment F45 | Patek, M. et al. "Promoters from *Corynebacterium glutamicum*: cloning, molecular analysis and search for a consensus motif", Microbiology, 142: 1297-1309 (1996) |
| X90364 | | Promoter fragment F64 | Patek, M. et al. "Promoters from *Corynebacterium glutamicum*: cloning, molecular analysis and search for a consensus motif", Microbiology, 142: 1297-1309 (1996) |
| X90365 | | Promoter fragment F75 | Patek, M. et al. "Promoters from *Corynebacterium glutamicum*: cloning, molecular analysis and search for a consensus motif", Microbiology, 142: 1297-1309 (1996) |

TABLE 2-continued

GENES IDENTIFIED FROM GENBANK

| GenBank™ Accession No. | Gene Name | Gene Function | Reference |
|---|---|---|---|
| X90366 | | Promoter fragment PF101 | Patek, M. et al. "Promoters from *Corynebacterium glutamicum*: cloning, molecular analysis and search for a consensus motif," Microbiology, 142: 1297-1309 (1996) |
| X90367 | | Promoter fragment PF104 | Patek, M. et al. "Promoters from *Corynebacterium glutamicum*: cloning, molecular analysis and search for a consensus motif," Microbiology, 142: 1297-1309 (1996) |
| X90368 | | Promoter fragment PF109 | Patek, M. et al. "Promoters from *Corynebacterium glutamicum*: cloning, molecular analysis and search for a consensus motif," Microbiology, 142: 1297-1309 (1996) |
| X93513 | amt | Ammonium transport system | Siewe, R. M. et al. "Functional and genetic characterization of the (methyl) ammonium uptake carrier of *Corynebacterium glutamicum*," J. Biol. Chem., 271(10): 5398-5403 (1996) |
| X93514 | betP | Glycine betaine transport system | Peter, H. et al. "Isolation, characterization, and expression of the *Corynebacterium glutamicum* betP gene, encoding the transport system for the compatible solute glycine betaine," J. Bacteriol., 178(17): 5229-5234 (1996) |
| X95649 | orf4 | | Patek, M. et al. "Identification and transcriptional analysis of the dapB-ORF2-dapA-ORF4 operon of *Corynebacterium glutamicum*, encoding two enzymes involved in L-lysine synthesis," Biotechnol. Lett., 19: 1113-1117 (1997) |
| X96471 | lysE; lysG | Lysine exporter protein; Lysine export regulator protein | Vrljic, M. et al. "A new type of transporter with a new type of cellular function: L-lysine export from *Corynebacterium glutamicum*," Mol. Microbiol., 22(5): 815-826 (1996) |
| X96580 | panB; panC; xylB | 3-methyl-2-oxobutanoate hydroxymethyltransferase; pantoate-beta-alanine ligase; xylulokinase | Sahm, H. et al. "D-pantothenate synthesis in *Corynebacterium glutamicum* and use of panBC and genes encoding L-valine synthesis for D-pantothenate overproduction," Appl. Environ. Microbiol., 65(5): 1973-1979 (1999) |
| X96962 X99289 | | Insertion sequence IS1207 and transposase Elongation factor P | Ramos, A. et al. "Cloning, sequencing and expression of the gene encoding elongation factor P in the amino-acid producer *Brevibacterium lactofermentum* (*Corynebacterium glutamicum* ATCC 13869)," Gene, 198: 217-222 (1997) |
| Y00140 | thrB | Homoserine kinase | Mateos, L. M. et al. "Nucleotide sequence of the homoserine kinase (thrB) gene of the *Brevibacterium lactofermentum*," Nucleic Acids Res., 15(9): 3922 (1987) |
| Y00151 | ddh | Meso-diaminopimelate D-dehydrogenase (EC 1.4.1.16) | Ishino, S. et al. "Nucleotide sequence of the meso-diaminopimelate D-dehydrogenase gene from *Corynebacterium glutamicum*," Nucleic Acids Res., 15(9): 3917 (1987) |
| Y00476 | thrA | Homoserine dehydrogenase | Mateos, L. M. et al. "Nucleotide sequence of the homoserine dehydrogenase (thrA) gene of the *Brevibacterium lactofermentum*," Nucleic Acids Res., 15(24): 10598 (1987) |
| Y00546 | hom; thrB | Homoserine dehydrogenase; homoserine kinase | Peoples, O. P. et al. "Nucleotide sequence and fine structural analysis of the *Corynebacterium glutamicum* hom-thrB operon," Mol. Microbiol., 2(1): 63-72 (1988) |
| Y08964 | murC; ftsQ/divD; ftsZ | UPD-N-acetylmuramate-alanine ligase; division initiation protein or cell division protein; cell division protein | Honrubia, M. P. et al. "Identification, characterization, and chromosomal organization of the ftsZ gene from *Brevibacterium lactofermentum*," Mol. Gen. Genet., 259(1): 97-104 (1998) |
| Y09163 | putP | High affinity proline transport system | Peter, H. et al. "Isolation of the putP gene of *Corynebacterium glutamicum* proline and characterization of a low-affinity uptake system for compatible solutes," Arch. Microbiol., 168(2): 143-151 (1997) |

TABLE 2-continued

GENES IDENTIFIED FROM GENBANK

| GenBank™ Accession No. | Gene Name | Gene Function | Reference |
|---|---|---|---|
| Y09548 | pyc | Pyruvate carboxylase | Peters-Wendisch, P. G. et al. "Pyruvate carboxylase from *Corynebacterium glutamicum*: characterization, expression and inactivation of the pyc gene," Microbiology, 144: 915-927 (1998) |
| Y09578 | leuB | 3-isopropylmalate dehydrogenase | Patek, M. et al. "Analysis of the leuB gene from *Corynebacterium glutamicum*," Appl. Microbiol. Biotechnol. 50(1): 42-47 (1998) |
| Y12472 | | Attachment site bacteriophage Phi-16 | Moreau, S. et al. "Site-specific integration of corynephage Phi-16: The construction of an integration vector," Microbiol., 145: 539-548 (1999) |
| Y12537 | proP | Proline/ectoine uptake system protein | Peter, H. et al. "*Corynebacterium glutamicum* is equipped with four secondary carriers for compatible solutes: Identification, sequencing, and characterization of the proline/ectoine uptake system, ProP, and the ectoine/proline/glycine betaine carrier, EctP", J. Bacteriol.. 180(22): 6005-6012 (1998) |
| Y13221 | glnA | Glutamine synthetase I | Jakoby, M. et al. "Isolation of *Corynebacterium glutamicum* glnA gene encoding glutamine synthetase I," FEMS Microbiol. Lett., 154(1): 81-88 (1997) |
| Y16642 | lpd | Dihydrolipoamide dehydrogenase | |
| Y18059 | | Attachment site Corynephage 304L | Moreau, S. et al. "Analysis of the integration functions of φ 304L: An integrase module among corynephages," Virology, 255(1): 150-159 (1999) |
| Z21501 | argS; lysA | Arginyl-tRNA synthetase; diaminopimelate decarboxylase (partial) | Oguiza, J. A. et al. "A gene encoding arginyl-tRNA synthetase is located in the upstream region of the lysA gene in *Brevibacterium lactofermentum*: Regulation of argS-lysA cluster expression by arginine," J. Bacteriol., 175(22): 7356-7362 (1993) |
| Z21502 | dapA; dapB | Dihydrodipicolinate synthase; dihydrodipicolinate reductase | Pisabarro, A. et al. "A cluster of three genes (dapA, orf2, and dapB) of *Brevibacterium lactofermentum* encodes dihydrodipicolinate reductase, and a third polypeptide of unknown function," J. Bacteriol., 175(9): 2743-2749 (1993) |
| Z29563 | thrC | Threonine synthase | Malumbres, M. et al. "Analysis and expression of the thrC gene of the encoded threonine synthase," Appl. Environ. Microbiol., 60(7) 2209-2219 (1994) |
| Z46753 Z49822 | 16S rDNA sigA | Gene for 16S ribosomal RNA SigA sigma factor | Oguiza, J. A. et al "Multiple sigma factor genes in *Brevibacterium lactofermentum*: Characterization of sigA and sigB," J. Bacteriol., 178(2): 550-553 (1996) |
| Z49823 | galE; dtxR | Catalytic activity UDP-galactose 4-epimerase; diphtheria toxin regulatory protein | Oguiza, J. A. et al "The galE gene encoding the UDP-galactose 4-epimerase of *Brevibacterium lactofermentum* is coupled transcriptionally to the dmdR gene," Gene, 177: 103-107 (1996) |
| Z49824 | orf1; sigB | ?; SigB sigma factor | Oguiza, J. A. et al "Multiple sigma factor genes in *Brevibacterium lactofermentum*: Characterization of sigA and sigB," J. Bacteriol., 178(2): 550-553 (1996) |
| Z66534 | | Transposase | Correia, A. et al. "Cloning and characterization of an IS-like element present in the genome of *Brevibacterium lactofermentum* ATCC 13869," Gene, 170(1): 91-94 (1996) |

¹A sequence for this gene was published in the indicated reference. However, the sequence obtained by the inventors of the present application is significantly longer than the published version. It is believed that the published version relied on an incorrect start codon, and thus represents only a fragment of the actual coding region.

TABLE 3

Corynebacterium and Brevibacterium Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| Brevibacterium | ammoniagenes | 21054 | | | | | | | |
| Brevibacterium | ammoniagenes | 19350 | | | | | | | |
| Brevibacterium | ammoniagenes | 19351 | | | | | | | |
| Brevibacterium | ammoniagenes | 19352 | | | | | | | |
| Brevibacterium | ammoniagenes | 19353 | | | | | | | |
| Brevibacterium | ammoniagenes | 19354 | | | | | | | |
| Brevibacterium | ammoniagenes | 19355 | | | | | | | |
| Brevibacterium | ammoniagenes | 19356 | | | | | | | |
| Brevibacterium | ammoniagenes | 21055 | | | | | | | |
| Brevibacterium | ammoniagenes | 21077 | | | | | | | |
| Brevibacterium | ammoniagenes | 21553 | | | | | | | |
| Brevibacterium | ammoniagenes | 21580 | | | | | | | |
| Brevibacterium | ammoniagenes | 39101 | | | | | | | |
| Brevibacterium | butanicum | 21196 | | | | | | | |
| Brevibacterium | divaricatum | 21792 | P928 | | | | | | |
| Brevibacterium | flavum | 21474 | | | | | | | |
| Brevibacterium | flavum | 21129 | | | | | | | |
| Brevibacterium | flavum | 21518 | | | | | | | |
| Brevibacterium | flavum | | | B11474 | | | | | |
| Brevibacterium | flavum | | | B11472 | | | | | |
| Brevibacterium | flavum | 21127 | | | | | | | |
| Brevibacterium | flavum | 21128 | | | | | | | |
| Brevibacterium | flavum | 21427 | | | | | | | |
| Brevibacterium | flavum | 21475 | | | | | | | |
| Brevibacterium | flavum | 21517 | | | | | | | |
| Brevibacterium | flavum | 21528 | | | | | | | |
| Brevibacterium | flavum | 21529 | | | | | | | |
| Brevibacterium | flavum | | | B11477 | | | | | |
| Brevibacterium | flavum | | | B11478 | | | | | |
| Brevibacterium | flavum | 21127 | | | | | | | |
| Brevibacterium | flavum | | | B11474 | | | | | |
| Brevibacterium | healii | 15527 | | | | | | | |
| Brevibacterium | ketoglutamicum | 21004 | | | | | | | |
| Brevibacterium | ketoglutamicum | 21089 | | | | | | | |
| Brevibacterium | ketosoreductum | 21914 | | | | | | | |
| Brevibacterium | lactofermentum | | | | 70 | | | | |
| Brevibacterium | lactofermentum | | | | 74 | | | | |
| Brevibacterium | lactofermentum | | | | 77 | | | | |
| Brevibacterium | lactofermentum | 21798 | | | | | | | |
| Brevibacterium | lactofermentum | 21799 | | | | | | | |
| Brevibacterium | lactofermentum | 21800 | | | | | | | |
| Brevibacterium | lactofermentum | 21801 | | | | | | | |
| Brevibacterium | lactofermentum | | | B11470 | | | | | |
| Brevibacterium | lactofermentum | | | B11471 | | | | | |
| Brevibacterium | lactofermentum | 21086 | | | | | | | |
| Brevibacterium | lactofermentum | 21420 | | | | | | | |
| Brevibacterium | lactofermentum | 21086 | | | | | | | |
| Brevibacterium | lactofermentum | 31269 | | | | | | | |
| Brevibacterium | linens | 9174 | | | | | | | |
| Brevibacterium | linens | 19391 | | | | | | | |
| Brevibacterium | linens | 8377 | | | | | | | |
| Brevibacterium | paraffinolyticum | | | | | 11160 | | | |
| Brevibacterium | spec. | | | | | | 717.73 | | |
| Brevibacterium | spec. | | | | | | 717.73 | | |
| Brevibacterium | spec. | 14604 | | | | | | | |
| Brevibacterium | spec. | 21860 | | | | | | | |
| Brevibacterium | spec. | 21864 | | | | | | | |
| Brevibacterium | spec. | 21865 | | | | | | | |
| Brevibacterium | spec. | 21866 | | | | | | | |
| Brevibacterium | spec. | 19240 | | | | | | | |
| Corynebacterium | acetoacidophilum | 21476 | | | | | | | |
| Corynebacterium | acetoacidophilum | 13870 | | | | | | | |
| Corynebacterium | acetoglutamicum | | | B11473 | | | | | |
| Corynebacterium | acetoglutamicum | | | B11475 | | | | | |
| Corynebacterium | acetoglutamicum | 15806 | | | | | | | |
| Corynebacterium | acetoglutamicum | 21491 | | | | | | | |
| Corynebacterium | acetoglutamicum | 31270 | | | | | | | |
| Corynebacterium | acetophilum | | | B3671 | | | | | |
| Corynebacterium | ammoniagenes | 6872 | | | | | | | 2399 |
| Corynebacterium | ammoniagenes | 15511 | | | | | | | |
| Corynebacterium | fujiokense | 21496 | | | | | | | |
| Corynebacterium | glutamicum | 14067 | | | | | | | |
| Corynebacterium | glutamicum | 39137 | | | | | | | |
| Corynebacterium | glutamicum | 21254 | | | | | | | |
| Corynebacterium | glutamicum | 21255 | | | | | | | |

TABLE 3-continued

Corynebacterium and Brevibacterium Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| Corynebacterium | glutamicum | 31830 | | | | | | | |
| Corynebacterium | glutamicum | 13032 | | | | | | | |
| Corynebacterium | glutamicum | 14305 | | | | | | | |
| Corynebacterium | glutamicum | 15455 | | | | | | | |
| Corynebacterium | glutamicum | 13058 | | | | | | | |
| Corynebacterium | glutamicum | 13059 | | | | | | | |
| Corynebacterium | glutamicum | 13060 | | | | | | | |
| Corynebacterium | glutamicum | 21492 | | | | | | | |
| Corynebacterium | glutamicum | 21513 | | | | | | | |
| Corynebacterium | glutamicum | 21526 | | | | | | | |
| Corynebacterium | glutamicum | 21543 | | | | | | | |
| Corynebacterium | glutamicum | 13287 | | | | | | | |
| Corynebacterium | glutamicum | 21851 | | | | | | | |
| Corynebacterium | glutamicum | 21253 | | | | | | | |
| Corynebacterium | glutamicum | 21514 | | | | | | | |
| Corynebacterium | glutamicum | 21516 | | | | | | | |
| Corynebacterium | glutamicum | 21299 | | | | | | | |
| Corynebacterium | glutamicum | 21300 | | | | | | | |
| Corynebacterium | glutamicum | 39684 | | | | | | | |
| Corynebacterium | glutamicum | 21488 | | | | | | | |
| Corynebacterium | glutamicum | 21649 | | | | | | | |
| Corynebacterium | glutamicum | 21650 | | | | | | | |
| Corynebacterium | glutamicum | 19223 | | | | | | | |
| Corynebacterium | glutamicum | 13869 | | | | | | | |
| Corynebacterium | glutamicum | 21157 | | | | | | | |
| Corynebacterium | glutamicum | 21158 | | | | | | | |
| Corynebacterium | glutamicum | 21159 | | | | | | | |
| Corynebacterium | glutamicum | 21355 | | | | | | | |
| Corynebacterium | glutamicum | 31808 | | | | | | | |
| Corynebacterium | glutamicum | 21674 | | | | | | | |
| Corynebacterium | glutamicum | 21562 | | | | | | | |
| Corynebacterium | glutamicum | 21563 | | | | | | | |
| Corynebacterium | glutamicum | 21564 | | | | | | | |
| Corynebacterium | glutamicum | 21565 | | | | | | | |
| Corynebacterium | glutamicum | 21566 | | | | | | | |
| Corynebacterium | glutamicum | 21567 | | | | | | | |
| Corynebacterium | glutamicum | 21568 | | | | | | | |
| Corynebacterium | glutamicum | 21569 | | | | | | | |
| Corynebacterium | glutamicum | 21570 | | | | | | | |
| Corynebacterium | glutamicum | 21571 | | | | | | | |
| Corynebacterium | glutamicum | 21572 | | | | | | | |
| Corynebacterium | glutamicum | 21573 | | | | | | | |
| Corynebacterium | glutamicum | 21579 | | | | | | | |
| Corynebacterium | glutamicum | 19049 | | | | | | | |
| Corynebacterium | glutamicum | 19050 | | | | | | | |
| Corynebacterium | glutamicum | 19051 | | | | | | | |
| Corynebacterium | glutamicum | 19052 | | | | | | | |
| Corynebacterium | glutamicum | 19053 | | | | | | | |
| Corynebacterium | glutamicum | 19054 | | | | | | | |
| Corynebacterium | glutamicum | 19055 | | | | | | | |
| Corynebacterium | glutamicum | 19056 | | | | | | | |
| Corynebacterium | glutamicum | 19057 | | | | | | | |
| Corynebacterium | glutamicum | 19058 | | | | | | | |
| Corynebacterium | glutamicum | 19059 | | | | | | | |
| Corynebacterium | glutamicum | 19060 | | | | | | | |
| Corynebacterium | glutamicum | 19185 | | | | | | | |
| Corynebacterium | glutamicum | 13286 | | | | | | | |
| Corynebacterium | glutamicum | 21515 | | | | | | | |
| Corynebacterium | glutamicum | 21527 | | | | | | | |
| Corynebacterium | glutamicum | 21544 | | | | | | | |
| Corynebacterium | glutamicum | 21492 | | | | | | | |
| Corynebacterium | glutamicum | | | B8183 | | | | | |
| Corynebacterium | glutamicum | | | B8182 | | | | | |
| Corynebacterium | glutamicum | | | B12416 | | | | | |
| Corynebacterium | glutamicum | | | B12417 | | | | | |
| Corynebacterium | glutamicum | | | B12418 | | | | | |
| Corynebacterium | glutamicum | | | B11476 | | | | | |
| Corynebacterium | glutamicum | 21608 | | | | | | | |
| Corynebacterium | lilium | | P973 | | | | | | |
| Corynebacterium | nitrilophilus | 21419 | | | | | | 11594 | |
| Corynebacterium | spec. | | P4445 | | | | | | |
| Corynebacterium | spec. | | P4446 | | | | | | |
| Corynebacterium | spec. | 31088 | | | | | | | |
| Corynebacterium | spec. | 31089 | | | | | | | |
| Corynebacterium | spec. | 31090 | | | | | | | |

TABLE 3-continued

*Corynebacterium* and *Brevibacterium* Strains Which May be Used in the Practice of the Invention

| Genus | species | ATCC | FERM | NRRL | CECT | NCIMB | CBS | NCTC | DSMZ |
|---|---|---|---|---|---|---|---|---|---|
| *Corynebacterium* | spec. | 31090 | | | | | | | |
| *Corynebacterium* | spec. | 31090 | | | | | | | |
| *Corynebacterium* | spec. | 15954 | | | | | | | 20145 |
| *Corynebacterium* | spec. | 21857 | | | | | | | |
| *Corynebacterium* | spec. | 21862 | | | | | | | |
| *Corynebacterium* | spec. | 21863 | | | | | | | |

ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen und Zellkulturen, Braunschweig, Germany
For reference see Sugawara, H. et al. (1993) World directory of collections of cultures of microorganisms: Bacteria, fungi and yeasts (4$^{th}$ edn), World federation for culture collections world data center on microorganisms, Saimata, Japen.

ATCC: American Type Culture Collection, Rockville, Md., USA
FERM: Fermentation Research Institute, Chiba, Japan
NRRL: ARS Culture Collection, Northern Regional Research Laboratory, Peoria, Ill., USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen und Zellkulturen, Braunschweig, Germany For reference see Sugawara, H. et al. (1993) World directory of collections of cultures of microorganisms: Bacteria, fungi and yeasts (4$^{th}$ edn), World federation for culture collections world data center on microorganisms, Saimata, Japan.

TABLE 4

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00315 | 1527 | GB_BA1:AB007125 | 4078 | AB007125 | *Serratia marcescens* slaA gene for surface layer protein, complete cds, isolate 8000. | *Serratia marcescens* | 40,386 | 26 Mar. 1998 |
| | | GB_IN1:CELC47D2 | 17381 | U64861 | *Caenorhabditis elegans* cosmid C47D2. | *Caenorhabditis elegans* | 36,207 | 28 Jul. 1996 |
| | | GB_HTG2:AC006732 | 159453 | AC006732 | *Caenorhabditis elegans* clone Y32G9, *** SEQUENCING IN PROGRESS ***, 9 unordered pieces. | *Caenorhabditis elegans* | 36,436 | 23 Feb. 1999 |
| rxa01503 | 372 | GB_PR3:AC005019 | 188362 | AC005019 | *Homo sapiens* BAC clone GS250A16 from 7p21-p22, complete sequence. | *Homo sapiens* | 39,722 | 27 Aug. 1998 |
| | | GB_GSS12:AQ390040 | 680 | AQ390040 | RPCI11-157C9.TJ RPCI-11 *Homo sapiens* genomic clone RPCI-11-157C9, genomic survey sequence. | *Homo sapiens* | 43,137 | 21 May 1999 |
| | | GB_GSS5:AQ784231 | 542 | AQ784231 | HS_3087_B1_C10_T7C CIT Approved Human Genomic Sperm Library D *Homo sapiens* genomic clone Plate = 3087 Col = 19 Row = F, genomic survey sequence. | *Homo sapiens* | 37,643 | 3 Aug. 1999 |
| rxa01299 | 2187 | GB_EST38:AW047296 | 614 | AW047296 | UI-M-BH1-amh-e-03-0-UI.s1 NIH_BMAP_M_S2 *Mus musculus* cDNA clone UI-M-BH1-amh-e-03-0-UI 3', mRNA sequence. | *Mus musculus* | 41,475 | 18 Sep. 1999 |
| | | GB_RO:AB004056 | 1581 | AB004056 | *Rattus norvegicus* mRNA for BarH-class homeodomain transcription factor, complete cds. | *Rattus norvegicus* | 41,031 | 2 Sep. 1998 |
| | | GB_RO:AB004056 | 1581 | AB004056 | *Rattus norvegicus* mRNA for BarH-class homeodomain transcription factor, complete cds. | *Rattus norvegicus* | 40,717 | 2 Sep. 1998 |
| rxa00951 | 416 | GB_BA1:SC121 | 31717 | AL109747 | *Streptomyces coelicolor* cosmid J21. | *Streptomyces coelicolor* A3(2) | 34,913 | 5 Aug. 1999 |
| | | GB_VI:MCU68299 | 230278 | U68299 | Mouse cytomegalovirus 1 complete genomic sequence. | Mouse cytomegalovirus | 40,097 | 4 Dec. 1996 |
| | | GB_VI:U93872 | 133661 | U93872 | Kaposi's sarcoma-associated herpesvirus glycoprotein M, DNA replication protein, glycoprotein, DNA replication protein, FLICE inhibitory protein and v-cyclin genes, complete cds, and tegument protein gene, partial cds. | Kaposi's sarcoma-associated herpesvirus | 36,029 | 9 Jul. 1997 |
| rxa01244 | 1827 | GB_BA1:AFAPHBHI | 4501 | M69036 | *Alcaligenes eutrophus* protein H (phbH) and protein I (phbI) genes, complete cds. | *Ralstonia eutropha* | 45,624 | 26 Apr. 1993 |
| | | GB_PR3:HSJ836E13 | 78055 | AL050326 | Human DNA sequence from clone 836E13 on chromosome 20 Contains ESTs, STS and GSSs, complete sequence. | *Homo sapiens* | 37,303 | 23 Nov. 1999 |
| | | GB_EST24:AI170227 | 409 | AI170227 | EST216152 Normalized rat lung, Bento Soares *Rattus* sp. cDNA clone RLUCF56 3' end, mRNA sequence. | *Rattus* sp. | 39,098 | 20 Jan. 1999 |
| rxa01300 | 390 | GB_PR3:HUMDODDA | 26764 | L39874 | *Homo sapiens* deoxycytidylate deaminase gene, complete cds. | *Homo sapiens* | 37,644 | 11 Aug. 1995 |
| | | GB_PAT:I40899 | 26764 | I40899 | Sequence 1 from patent U.S Pat. No. 5622851. | Unknown. | 37,644 | 13 May 1997 |
| | | GB_PAT:I40900 | 1317 | I40900 | Sequence 2 from patent U.S Pat. No. 5622851. | Unknown. | 37,644 | 13 May 1997 |
| rxa00953 | 789 | GB_BA1:SC121 | 31717 | AL109747 | *Streptomyces coelicolor* cosmid J21. | *Streptomyces coelicolor* A3(2) | 39,398 | 5 Aug. 1999 |
| | | GB_BA1:BLTRP | 7725 | X04960 | *Brevibacterium lactofermentum* tryptophan operon. | *Corynebacterium glutamicum* | 39,610 | 10 Feb. 1999 |
| | | GB_PAT:E01375 | 7726 | E01375 | DNA sequence of tryptophan operon. | *Corynebacterium glutamicum* | 46,753 | 29 Sep. 1997 |
| rxa01943 | 2172 | GB_BA1:CORPTSMA | 2656 | L18874 | *Corynebacterium glutamicum* phosphoenolpyruvate sugar phosphotransferase (ptsM) mRNA, complete cds. | *Corynebacterium glutamicum* | 100,000 | 24 Nov. 1994 |
| | | GB_BA1:BRLPTSG | 3163 | L18875 | *Brevibacterium lactofermentum* phosphoenolpyruvate sugar phosphotransferase (ptsG) gene, complete cds. | *Brevibacterium lactofermentum* | 84,963 | 1 Oct. 1993 |
| | | GB_BA2:AF045481 | 2841 | AF045481 | *Corynebacterium ammoniagenes* glucose permease (ptsG) gene, complete cds. | *Corynebacterium ammoniagenes* | 53,558 | 29 Jul. 1998 |

What is claimed is:

1. An isolated nucleic acid molecule comprising the nucleotide sequence of SEQ ID NO:21, or a complement thereof.

2. An isolated nucleic acid molecule which encodes a polypeptide comprising the amino acid sequence of SEQ ID NO:22, or a complement thereof.

3. An isolated nucleic acid molecule comprising a nucleotide sequence which is at least 90% identical to the entire nucleotide sequence of SEQ ID NO:21, wherein the nucleic acid molecule encodes a polypeptide having a phosphocarrier protein HPr activity, or a complement thereof.

4. An isolated nucleic acid molecule comprising a nucleotide sequence which is at least 95% identical to the entire nucleotide sequence of SEQ ID NO:21, wherein the nucleic acid molecule encodes a polypeptide having a phosphocarrier protein HPr activity, or a complement thereof.

5. An isolated nucleic acid molecule which hybridizes to the complement of the nucleotide sequence of SEQ ID NO:21 in 6X sodium chloride/sodium citrate (SSC) at 45° C., followed by one or more washes in 0.2 X SSC, 0.1% SDS at 65° C., or a complement thereof, wherein the nucleic acid molecule encodes a polypeptide having a phosphocarrier protein HPr activity.

6. An isolated nucleic acid molecule comprising a nucleotide sequence which encodes a polypeptide which is at least 90% identical to the entire polypeptide sequence of SEQ ID NO:22, or a complement thereof, wherein the polypeptide has a phosphocarrier protein HPr activity.

7. An isolated nucleic acid molecule comprising a nucleotide sequence which encodes a polypeptide which is at least 95% identical to the entire polypeptide sequence of SEQ ID NO:22, or a complement thereof, wherein the polypeptide has a phosphocarrier protein HPr activity.

8. An isolated nucleic acid molecule comprising the nucleic acid molecule of any one of claims 1, 2, 3, 4, 5, 6 and 7 and a nucleotide sequence encoding a heterologous polypeptide.

9. A vector comprising the nucleic acid molecule of any one of claims 1, 2, 3, 4, 5, 6 and 7.

10. The vector of claim 9, which is an expression vector.

11. A host cell transfected with the expression vector of claim 4.

12. The host cell of claim 11, wherein said cell is a microorganism.

13. The host cell of claim 12, wherein said cell belongs to the genus *Corynebacterium* or *Brevibacterium*.

14. A method of producing a polypeptide comprising culturing the host cell of claim 11 in an appropriate culture medium to, thereby, produce the polypeptide.

15. A method for producing a fine chemical, comprising culturing the cell of claim 11 such that the fine chemical is produced.

16. The method of claim 15, wherein said method further comprises the step of recovering the fine chemical from said culture.

17. The method of claim 15, wherein said cell belongs to the genus *Corynebacterium* or *Brevibacterium*.

18. The method of claim 15, wherein said cell is selected from the group consisting of *Corynebacterium glutamicum, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens,* and *Brevibacterium paraffinolyticum*.

19. The method of claim 15, wherein expression of the nucleic acid molecule from said vector results in enhancement of production of said fine chemical.

20. The method of claim 15, wherein said fine chemical is selected from the group consisting of organic acids, proteinogenic and nonproteinogenic amino acids, purine and pyrimidine bases, nucleosides, nucleotides, lipids, saturated and unsaturated fatty acids, diols, carbohydrates, aromatic compounds, vitamins, cofactors, polyketides, and enzymes.

21. The method of claim 15, wherein said fine chemical is an amino acid selected from the group consisting of lysine, glutamate, glutamine, alanine, aspartate, glycine, serine, threonine, methionine, cysteine, valine, leucine, isoleucine, arginine, proline, histidine, tyrosine, phenylalanine, and tryptophan.

22. A method for diagnosing the presence or activity of *Corynebacterium glutamicum* in a subject, comprising detecting the presence of at least one of the nucleic acid molecules of any one of claims 1, 2, 3, 4, 5, 6 and 7, thereby diagnosing the presence or activity of *Corynebacterium glutamicum* in the subject.

* * * * *